a2) United States Patent
Denham et al.

(10) Patent No.: US 8,652,172 B2
(45) Date of Patent: Feb. 18, 2014

(54) FLEXIBLE ANCHORS FOR TISSUE FIXATION

(75) Inventors: Gregory J. Denham, Warsaw, IN (US); Daniel Norton, Indianapolis, IN (US); Chris Palese, South Whitley, IN (US); Kevin T. Stone, Winona Lake, IN (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 0 days.

(21) Appl. No.: 13/177,153

(22) Filed: Jul. 6, 2011

(65) Prior Publication Data
US 2011/0264141 A1 Oct. 27, 2011

Related U.S. Application Data

(63) Continuation-in-part of application No. 13/111,564, filed on May 19, 2011, now Pat. No. 8,574,235, and a continuation-in-part of application No. 13/098,927, filed on May 2, 2011, which is a continuation-in-part of application No. 12/196,398, filed on Aug. 22, 2008, now Pat. No. 7,959,650, application No. 13/177,153, which is a continuation-in-part of application No. 13/098,897, filed on May 2, 2011, now Pat. No. 8,562,645, and a continuation-in-part of application No. 12/976,328, filed on Dec. 22, 2010, now Pat. No. 8,273,106, which is a continuation of application No. 11/869,440, filed on Oct. 9, 2007, now Pat. No. 7,857,830, which is a continuation-in-part of application No. 11/347,661, filed on Feb. 3, 2006, now (Continued)

(51) Int. Cl.
*A61B 17/04* (2006.01)

(52) U.S. Cl.
USPC .......................................... 606/232; 606/228

(58) Field of Classification Search
USPC .......... 623/13.11–13.2; 606/70, 71, 280–299, 606/74, 228, 232, 233, 213, 151; 600/37, 600/29, 30
See application file for complete search history.

(56) References Cited

U.S. PATENT DOCUMENTS

| 65,499 A | 6/1867 | Miller |
| 126,366 A | 4/1872 | Wills |

(Continued)

FOREIGN PATENT DOCUMENTS

| AU | 4957264 | 3/1966 |
| AU | 440266 | 10/1967 |

(Continued)

OTHER PUBLICATIONS

"Arthroscopic Meniscal Repair using the Meniscal Cinch™", Surgical Technique brochure. (2008) Arthrex® 6 sheets.

(Continued)

*Primary Examiner* — Dianne Dornbusch
(74) *Attorney, Agent, or Firm* — Harness, Dickey

(57) ABSTRACT

An anchor for securing tissue to bone can include a flexible first tubular member, a flexible second tubular member, and a first suture member. The first tubular member can include a first wall defining a first passage between first and second ends. The second tubular member can include a second wall defining a second passage between first and second ends. The first suture member can couple the first tubular member and the second tubular member. The first suture member can pass through the first wall and the first passage and the second wall and the second passage. The first tubular member and the second tubular member can engage each other and deform to form an anchoring mass upon tensioning the first suture member. A method of preparing an anchor for securing tissue to bone and a method of securing a tissue to a bone are also provided.

27 Claims, 9 Drawing Sheets

Related U.S. Application Data

Pat. No. 7,749,250, application No. 13/177,153, which is a continuation-in-part of application No. 12/938,902, filed on Nov. 3, 2010, now Pat. No. 8,597,327, and a continuation-in-part of application No. 12/915,962, filed on Oct. 29, 2010, now Pat. No. 8,562,647, and a continuation-in-part of application No. 12/570,854, filed on Sep. 30, 2009, now Pat. No. 8,303,604, which is a continuation-in-part of application No. 12/014,399, filed on Jan. 15, 2008, now Pat. No. 7,909,851, application No. 13/177,153, which is a continuation-in-part of application No. 12/489,168, filed on Jun. 22, 2009, now Pat. No. 8,361,113, which is a continuation-in-part of application No. 12/474,802, filed on May 29, 2009, now Pat. No. 8,088,130, which is a continuation-in-part of application No. 12/196,410, filed on Aug. 22, 2008, now Pat. No. 8,118,836, application No. 13/177,153, which is a continuation-in-part of application No. 12/489,181, filed on Jun. 22, 2009, now Pat. No. 8,298,262, which is a continuation-in-part of application No. 12/014,399, filed on Jan. 15, 2008, now Pat. No. 7,909,851, and a continuation-in-part of application No. 12/014,340, filed on Jan. 15, 2008, now Pat. No. 7,905,904, and a continuation-in-part of application No. 11/935,681, filed on Nov. 6, 2007, now Pat. No. 7,905,903, application No. 13/177,153, which is a continuation-in-part of application No. 11/504,882, filed on Aug. 16, 2006, which is a continuation-in-part of application No. 11/408,282, filed on Apr. 20, 2006, now abandoned.

(56) References Cited

U.S. PATENT DOCUMENTS

| | | |
|---|---|---|
| 233,475 A | 10/1880 | Cook et al. |
| 261,501 A | 7/1882 | Vandermark |
| 268,407 A | 12/1882 | Hughes |
| 330,087 A | 11/1885 | Binns |
| 417,805 A | 12/1889 | Beaman |
| 487,304 A | 12/1892 | Todd |
| 762,710 A | 6/1901 | Hall |
| 837,767 A | 12/1906 | Aims |
| 838,203 A | 12/1906 | Neil |
| 1,059,631 A | 4/1913 | Popovics |
| 1,131,155 A | 3/1915 | Murphy |
| 1,153,450 A | 9/1915 | Schaff |
| 1,346,940 A | 7/1920 | Collins |
| 1,635,066 A | 7/1927 | Wells |
| 1,950,799 A | 3/1934 | Jones |
| 2,065,659 A | 12/1936 | Cullen |
| 2,108,206 A | 2/1938 | Meeker |
| 2,121,193 A | 6/1938 | Hanicke |
| 2,242,003 A | 5/1941 | Lorenzo |
| 2,267,925 A | 12/1941 | Johnston |
| 2,302,986 A | 11/1942 | Vollrath |
| 2,329,398 A | 9/1943 | Duffy |
| RE22,857 E | 3/1947 | Ogburn |
| 2,526,959 A | 10/1950 | Lorenzo |
| 2,528,456 A | 10/1950 | Stevenson |
| 2,562,419 A | 7/1951 | Ferris |
| 2,581,564 A | 1/1952 | Villegas |
| 2,600,395 A | 6/1952 | Domoj et al. |
| 2,610,631 A | 9/1952 | Calicchio |
| 2,665,597 A | 1/1954 | Hill |
| 2,669,774 A | 2/1954 | Mitchell |
| 2,698,986 A | 1/1955 | Brown |
| 2,760,488 A | 8/1956 | Pierce |
| 2,833,284 A | 5/1958 | Springer |
| 2,846,712 A | 8/1958 | Markman |
| 2,860,393 A | 11/1958 | Brock |
| 2,880,728 A | 4/1959 | Rights |
| 2,881,762 A | 4/1959 | Lowrie |
| 2,883,096 A | 4/1959 | Dawson |
| 2,913,042 A | 11/1959 | Taylor |
| 3,000,009 A | 9/1961 | Selstad |
| 3,003,155 A | 10/1961 | Mielzynski et al. |
| 3,013,559 A | 12/1961 | Thomas |
| 3,037,619 A | 6/1962 | Stevans |
| 3,039,460 A | 6/1962 | Chandler |
| 3,090,386 A | 5/1963 | Curtis |
| 3,103,666 A | 9/1963 | Bone |
| 3,123,077 A | 3/1964 | Alcamo |
| 3,125,095 A | 3/1964 | Kaufman et al. |
| 3,209,422 A | 10/1965 | Dritz |
| 3,234,938 A | 2/1966 | Robinson |
| 3,240,379 A | 3/1966 | Bremer et al. |
| 3,250,271 A | 5/1966 | Lippes |
| 3,399,432 A | 9/1968 | Merser |
| 3,409,014 A | 11/1968 | Shannon |
| RE26,501 E | 12/1968 | Kendrick et al. |
| 3,435,475 A | 4/1969 | Bisk |
| 3,467,089 A | 9/1969 | Hasson |
| 3,470,834 A | 10/1969 | Bone |
| 3,470,875 A | 10/1969 | Johnson |
| 3,500,820 A | 3/1970 | Almen |
| 3,507,274 A | 4/1970 | Soichet |
| 3,513,484 A | 5/1970 | Hausner |
| 3,515,132 A | 6/1970 | McKnight |
| 3,522,803 A | 8/1970 | Majzlin |
| 3,527,223 A | 9/1970 | Shein |
| 3,533,406 A | 10/1970 | Hutterer et al. |
| 3,541,591 A | 11/1970 | Hoegerman |
| 3,547,389 A | 12/1970 | Mitchell |
| 3,579,831 A | 5/1971 | Stevens et al. |
| 3,590,616 A | 7/1971 | Schussler |
| 3,608,095 A | 9/1971 | Barry |
| 3,618,447 A | 11/1971 | Goins |
| 3,628,530 A | 12/1971 | Schwartz |
| 3,643,649 A | 2/1972 | Amato |
| 3,648,705 A | 3/1972 | Lary |
| 3,656,483 A | 4/1972 | Rudel |
| 3,659,597 A | 5/1972 | Wolfers |
| 3,664,345 A | 5/1972 | Dabbs et al. |
| 3,665,560 A | 5/1972 | Bennett et al. |
| 3,675,639 A | 7/1972 | Cimber |
| 3,683,422 A | 8/1972 | Stemmer et al. |
| 3,692,022 A | 9/1972 | Ewing |
| 3,695,271 A | 10/1972 | Chodorow |
| 3,699,969 A | 10/1972 | Allen |
| 3,716,058 A | 2/1973 | Tanner, Jr. |
| 3,744,488 A | 7/1973 | Cox |
| 3,752,516 A | 8/1973 | Mumma |
| 3,757,629 A | 9/1973 | Schneider |
| 3,763,856 A | 10/1973 | Blomberg |
| 3,771,520 A | 11/1973 | Lerner |
| 3,777,748 A | 12/1973 | Abramson |
| 3,807,407 A | 4/1974 | Schweizer |
| 3,810,456 A | 5/1974 | Karman |
| 3,825,010 A | 7/1974 | McDonald |
| 3,840,017 A | 10/1974 | Violante et al. |
| 3,842,824 A | 10/1974 | Neufeld |
| 3,842,840 A | 10/1974 | Schweizer |
| 3,845,772 A | 11/1974 | Smith |
| 3,867,933 A | 2/1975 | Kitrilakis |
| 3,867,944 A | 2/1975 | Samuels |
| 3,871,368 A | 3/1975 | Johnson et al. |
| 3,871,379 A | 3/1975 | Clarke |
| 3,874,388 A | 4/1975 | King et al. |
| 3,875,648 A | 4/1975 | Bone |
| 3,877,570 A | 4/1975 | Barry |
| 3,880,156 A | 4/1975 | Hoff |
| 3,881,475 A | 5/1975 | Gordon et al. |
| 3,889,666 A | 6/1975 | Lerner |
| 3,892,240 A | 7/1975 | Park |
| 3,896,500 A | 7/1975 | Rambert et al. |
| 3,907,442 A | 9/1975 | Reid |
| 3,910,281 A | 10/1975 | Kletschka et al. |

(56) References Cited

U.S. PATENT DOCUMENTS

| | | | |
|---|---|---|---|
| 3,918,444 A | 11/1975 | Hoff et al. | |
| 3,918,455 A | 11/1975 | Coplan | |
| 3,927,666 A | 12/1975 | Hoff | |
| 3,931,667 A | 1/1976 | Merser et al. | |
| 3,933,153 A | 1/1976 | Csatary et al. | |
| 3,937,217 A | 2/1976 | Kosonen et al. | |
| 3,943,932 A | 3/1976 | Woo | |
| 3,946,446 A | 3/1976 | Schofield | |
| 3,946,728 A | 3/1976 | Bettex et al. | |
| 3,946,740 A | 3/1976 | Bassett | |
| 3,953,896 A | 5/1976 | Treace | |
| 3,954,103 A | 5/1976 | Garcia-Roel et al. | |
| 3,961,632 A | 6/1976 | Moossun | |
| 3,973,560 A | 8/1976 | Emmett et al. | |
| 3,976,079 A | 8/1976 | Samuels et al. | |
| 3,977,050 A | 8/1976 | Perez et al. | |
| 3,979,799 A | 9/1976 | Merser et al. | |
| 3,985,138 A | 10/1976 | Jarvik | |
| 3,990,619 A | 11/1976 | Russell | |
| 4,005,707 A | 2/1977 | Moulding, Jr. | |
| 4,006,747 A | 2/1977 | Kronenthal et al. | |
| 4,007,743 A | 2/1977 | Blake | |
| 4,013,071 A | 3/1977 | Rosenberg et al. | |
| 4,026,281 A | 5/1977 | Mayberry et al. | |
| 4,036,101 A | 7/1977 | Burnett | |
| 4,050,100 A * | 9/1977 | Barry | 623/15.11 |
| 4,054,954 A | 10/1977 | Nakayama et al. | |
| 4,085,466 A | 4/1978 | Goodfellow et al. | |
| 4,094,313 A | 6/1978 | Komamura et al. | |
| 4,099,750 A | 7/1978 | McGrew | |
| 4,103,690 A | 8/1978 | Harris | |
| RE29,819 E | 10/1978 | Bone | |
| 4,121,487 A | 10/1978 | Bone | |
| 4,143,656 A | 3/1979 | Holmes et al. | |
| 4,144,876 A | 3/1979 | DeLeo | |
| 4,149,277 A | 4/1979 | Bokros | |
| 4,157,714 A | 6/1979 | Foltz et al. | |
| 4,160,453 A | 7/1979 | Miller | |
| 4,164,225 A | 8/1979 | Johnson et al. | |
| 4,172,458 A | 10/1979 | Pereyra | |
| 4,175,555 A | 11/1979 | Herbert et al. | |
| 4,185,636 A | 1/1980 | Gabbay et al. | |
| 4,196,883 A | 4/1980 | Einhorn et al. | |
| 4,210,148 A | 7/1980 | Stivala | |
| 4,235,161 A | 11/1980 | Kunreuther | |
| 4,235,238 A | 11/1980 | Ogiu et al. | |
| 4,237,779 A | 12/1980 | Kunreuther | |
| 4,243,037 A | 1/1981 | Smith | |
| 4,249,525 A | 2/1981 | Krzeminski | |
| 4,263,913 A | 4/1981 | Malmin | |
| 4,265,246 A | 5/1981 | Barry | |
| 4,273,117 A | 6/1981 | Neuhauser et al. | |
| 4,275,717 A | 6/1981 | Bolesky | |
| 4,287,807 A | 9/1981 | Pacharis et al. | |
| 4,291,698 A | 9/1981 | Fuchs et al. | |
| 4,301,551 A | 11/1981 | Dore et al. | |
| 4,307,723 A | 12/1981 | Finney | |
| 4,312,337 A | 1/1982 | Donohue | |
| 4,316,469 A | 2/1982 | Kapitanov et al. | |
| 4,326,531 A | 4/1982 | Shimonaka et al. | |
| 4,345,601 A | 8/1982 | Fukuda | |
| 4,349,027 A | 9/1982 | DiFrancesco | |
| 4,388,921 A | 6/1983 | Sutter et al. | |
| 4,400,833 A | 8/1983 | Kurland | |
| 4,402,445 A | 9/1983 | Green | |
| 4,409,974 A | 10/1983 | Freedland | |
| 4,438,769 A | 3/1984 | Pratt et al. | |
| 4,441,489 A | 4/1984 | Evans et al. | |
| 4,454,875 A | 6/1984 | Pratt et al. | |
| 4,462,395 A | 7/1984 | Johnson | |
| 4,463,753 A | 8/1984 | Gustilo | |
| 4,473,102 A | 9/1984 | Ohman et al. | |
| 4,484,570 A | 11/1984 | Sutter et al. | |
| 4,489,446 A * | 12/1984 | Reed | 623/2.37 |
| 4,493,323 A | 1/1985 | Albright et al. | |
| 4,496,468 A | 1/1985 | House et al. | |
| 4,505,274 A | 3/1985 | Speelman | |
| 4,509,516 A | 4/1985 | Richmond | |
| 4,531,522 A | 7/1985 | Bedi et al. | |
| 4,532,926 A | 8/1985 | O'Holla | |
| 4,534,350 A | 8/1985 | Golden et al. | |
| 4,535,764 A | 8/1985 | Ebert | |
| 4,537,185 A | 8/1985 | Stednitz | |
| 4,549,545 A | 10/1985 | Levy | |
| 4,549,652 A | 10/1985 | Free | |
| 4,561,432 A | 12/1985 | Mazor | |
| 4,564,007 A | 1/1986 | Coombs et al. | |
| 4,570,623 A | 2/1986 | Ellison et al. | |
| 4,573,844 A | 3/1986 | Smith | |
| 4,576,608 A | 3/1986 | Homsy | |
| 4,584,722 A | 4/1986 | Levy et al. | |
| 4,590,928 A | 5/1986 | Hunt et al. | |
| 4,595,007 A | 6/1986 | Mericle | |
| 4,596,249 A | 6/1986 | Freda et al. | |
| 4,602,635 A | 7/1986 | Mulhollan et al. | |
| 4,602,636 A | 7/1986 | Noiles | |
| 4,604,997 A | 8/1986 | De Bastiani et al. | |
| 4,605,414 A | 8/1986 | Czajka | |
| 4,616,650 A | 10/1986 | Green et al. | |
| 4,621,640 A | 11/1986 | Mulhollan et al. | |
| 4,624,254 A | 11/1986 | McGarry et al. | |
| 4,632,100 A | 12/1986 | Somers et al. | |
| 4,635,637 A | 1/1987 | Schreiber | |
| 4,636,121 A | 1/1987 | Miller | |
| 4,641,652 A | 2/1987 | Hutterer et al. | |
| 4,649,916 A | 3/1987 | Frimberger | |
| 4,649,952 A | 3/1987 | Jobe | |
| 4,653,486 A | 3/1987 | Coker | |
| 4,653,487 A | 3/1987 | Maale | |
| 4,653,489 A | 3/1987 | Tronzo | |
| 4,655,777 A | 4/1987 | Dunn et al. | |
| 4,662,068 A | 5/1987 | Polonsky | |
| 4,667,662 A | 5/1987 | Titone et al. | |
| 4,667,675 A | 5/1987 | Davis | |
| 4,669,473 A | 6/1987 | Richards et al. | |
| 4,683,895 A | 8/1987 | Pohndorf | |
| 4,688,561 A | 8/1987 | Reese | |
| 4,690,169 A | 9/1987 | Jobe | |
| 4,696,300 A | 9/1987 | Anderson | |
| 4,705,040 A | 11/1987 | Mueller et al. | |
| 4,708,132 A | 11/1987 | Silvestrini | |
| 4,714,475 A | 12/1987 | Grundei et al. | |
| 4,716,893 A | 1/1988 | Fischer et al. | |
| 4,719,671 A | 1/1988 | Ito et al. | |
| 4,719,917 A | 1/1988 | Barrows et al. | |
| 4,723,540 A | 2/1988 | Gilmer, Jr. | |
| 4,724,839 A | 2/1988 | Bedi et al. | |
| 4,728,332 A | 3/1988 | Albrektsson | |
| 4,738,255 A | 4/1988 | Goble et al. | |
| 4,739,751 A | 4/1988 | Sapega et al. | |
| 4,741,330 A | 5/1988 | Hayhurst | |
| 4,741,336 A | 5/1988 | Failla et al. | |
| 4,744,353 A | 5/1988 | McFarland | |
| 4,744,793 A | 5/1988 | Parr et al. | |
| 4,750,492 A | 6/1988 | Jacobs | |
| 4,760,843 A | 8/1988 | Fischer et al. | |
| 4,760,844 A | 8/1988 | Kyle | |
| 4,760,848 A | 8/1988 | Hasson | |
| 4,770,663 A | 9/1988 | Hanslik et al. | |
| 4,772,261 A | 9/1988 | Von Hoff et al. | |
| 4,772,286 A | 9/1988 | Goble et al. | |
| 4,773,910 A | 9/1988 | Chen et al. | |
| 4,775,380 A | 10/1988 | Seedhom et al. | |
| 4,776,328 A | 10/1988 | Frey et al. | |
| 4,781,190 A | 11/1988 | Lee et al. | |
| 4,784,126 A | 11/1988 | Hourahane et al. | |
| 4,787,882 A | 11/1988 | Claren et al. | |
| 4,790,297 A | 12/1988 | Luque et al. | |
| 4,793,363 A | 12/1988 | Ausherman et al. | |
| 4,809,695 A | 3/1989 | Gwathmey et al. | |
| 4,813,406 A | 3/1989 | Ogle, II | |
| 4,823,794 A | 4/1989 | Pierce | |
| 4,828,562 A | 5/1989 | Kenna | |
| 4,832,026 A | 5/1989 | Jones | |

(56) References Cited

U.S. PATENT DOCUMENTS

| | | | |
|---|---|---|---|
| 4,834,098 A | 5/1989 | Jones |
| 4,838,282 A | 6/1989 | Strasser et al. |
| 4,841,960 A | 6/1989 | Garner |
| 4,851,005 A | 7/1989 | Hunt et al. |
| 4,858,608 A | 8/1989 | McQuilkin et al. |
| 4,860,513 A | 8/1989 | Whitman |
| 4,863,383 A | 9/1989 | Grafelmann et al. |
| 4,870,957 A | 10/1989 | Goble et al. |
| 4,873,976 A | 10/1989 | Schreiber |
| 4,887,601 A | 12/1989 | Richards |
| 4,890,615 A | 1/1990 | Caspari et al. |
| 4,893,619 A | 1/1990 | Dale et al. |
| 4,893,974 A | 1/1990 | Fischer et al. |
| 4,895,148 A | 1/1990 | Bays et al. |
| 4,896,668 A | 1/1990 | Popoff et al. |
| 4,898,156 A | 2/1990 | Gatturna et al. |
| 4,899,743 A | 2/1990 | Nicholson et al. |
| 4,901,721 A | 2/1990 | Hakki |
| 4,922,897 A | 5/1990 | Sapega et al. |
| 4,923,461 A | 5/1990 | Caspari et al. |
| 4,927,421 A | 5/1990 | Goble et al. |
| 4,946,377 A | 8/1990 | Kovach |
| 4,946,468 A | 8/1990 | Li |
| 4,950,270 A | 8/1990 | Bowman et al. |
| 4,950,285 A | 8/1990 | Wilk |
| 4,960,381 A | 10/1990 | Niznick |
| 4,961,741 A | 10/1990 | Hayhurst |
| 4,968,315 A | 11/1990 | Gatturna |
| 4,968,317 A | 11/1990 | Tormala et al. |
| 4,969,886 A | 11/1990 | Cziffer et al. |
| 4,974,488 A | 12/1990 | Spralja |
| 4,976,736 A | 12/1990 | White et al. |
| 4,978,350 A | 12/1990 | Wagenknecht et al. |
| 4,979,956 A | 12/1990 | Silvestrini |
| 4,983,176 A | 1/1991 | Cushman et al. |
| 4,988,351 A | 1/1991 | Paulos et al. |
| 4,994,074 A | 2/1991 | Bezwada et al. |
| 4,997,433 A | 3/1991 | Goble et al. |
| 5,002,550 A | 3/1991 | Li |
| 5,002,562 A | 3/1991 | Oberlander |
| 5,002,574 A | 3/1991 | May et al. |
| 5,007,921 A | 4/1991 | Brown |
| 5,030,224 A | 7/1991 | Wright et al. |
| 5,030,235 A | 7/1991 | Campbell, Jr. |
| 5,035,701 A | 7/1991 | Kabbara |
| 5,037,422 A | 8/1991 | Hayhurst et al. |
| 5,037,426 A | 8/1991 | Goble et al. |
| 5,041,129 A | 8/1991 | Hayhurst et al. |
| 5,046,513 A | 9/1991 | Gatturna et al. |
| 5,047,030 A | 9/1991 | Draenert |
| 5,053,046 A | 10/1991 | Janese |
| 5,053,047 A | 10/1991 | Yoon |
| 5,059,201 A | 10/1991 | Asnis |
| 5,059,206 A | 10/1991 | Winters |
| 5,061,277 A | 10/1991 | Carpentier et al. |
| 5,062,344 A | 11/1991 | Gerker |
| 5,062,843 A | 11/1991 | Mahony, III |
| 5,064,431 A * | 11/1991 | Gilbertson et al. .......... 623/2.37 |
| 5,071,420 A | 12/1991 | Paulos et al. |
| 5,074,874 A | 12/1991 | Yoon et al. |
| 5,078,731 A | 1/1992 | Hayhurst |
| 5,078,843 A | 1/1992 | Pratt |
| 5,084,050 A | 1/1992 | Draenert |
| 5,084,058 A | 1/1992 | Li |
| 5,085,661 A | 2/1992 | Moss |
| 5,087,263 A | 2/1992 | Li |
| 5,087,309 A | 2/1992 | Melton, Jr. |
| 5,089,012 A | 2/1992 | Prou |
| 5,092,866 A | 3/1992 | Breard et al. |
| 5,098,435 A | 3/1992 | Stednitz et al. |
| 5,100,415 A | 3/1992 | Hayhurst |
| 5,100,417 A | 3/1992 | Cerier et al. |
| 5,108,433 A | 4/1992 | May et al. |
| 5,116,337 A | 5/1992 | Johnson |
| 5,116,373 A | 5/1992 | Jakob et al. |
| 5,116,375 A | 5/1992 | Hofmann |
| 5,123,913 A | 6/1992 | Wilk et al. |
| 5,123,914 A | 6/1992 | Cope |
| 5,127,785 A | 7/1992 | Faucher et al. |
| 5,129,901 A | 7/1992 | Decoste |
| 5,129,902 A | 7/1992 | Goble et al. |
| 5,129,904 A | 7/1992 | Illi et al. |
| 5,129,906 A | 7/1992 | Ross et al. |
| 5,139,498 A | 8/1992 | Astudillo Ley |
| 5,139,499 A | 8/1992 | Small et al. |
| 5,139,520 A | 8/1992 | Rosenberg |
| 5,143,498 A | 9/1992 | Whitman |
| 5,147,362 A | 9/1992 | Goble |
| 5,149,329 A | 9/1992 | Richardson |
| 5,151,104 A | 9/1992 | Kenna |
| 5,152,790 A | 10/1992 | Rosenberg et al. |
| 5,154,189 A | 10/1992 | Oberlander |
| 5,156,616 A | 10/1992 | Meadows et al. |
| 5,163,960 A | 11/1992 | Bonutti |
| D331,626 S | 12/1992 | Hayhurst et al. |
| 5,169,400 A | 12/1992 | Muhling et al. |
| 5,176,682 A | 1/1993 | Chow |
| 5,178,629 A | 1/1993 | Kammerer |
| 5,183,458 A | 2/1993 | Marx |
| 5,192,282 A | 3/1993 | Draenert et al. |
| 5,197,987 A | 3/1993 | Koch et al. |
| 5,203,784 A | 4/1993 | Ross et al. |
| 5,203,787 A | 4/1993 | Noblitt et al. |
| 5,207,679 A | 5/1993 | Li |
| 5,209,753 A | 5/1993 | Biedermann et al. |
| 5,209,805 A | 5/1993 | Spraggins |
| 5,211,647 A | 5/1993 | Schmieding |
| 5,211,650 A | 5/1993 | Noda |
| 5,214,987 A | 6/1993 | Fenton, Sr. |
| 5,219,359 A | 6/1993 | McQuilkin et al. |
| 5,222,976 A | 6/1993 | Yoon |
| 5,224,946 A | 7/1993 | Hayhurst et al. |
| 5,230,699 A | 7/1993 | Grasinger |
| 5,232,436 A | 8/1993 | Janevski |
| 5,234,435 A | 8/1993 | Seagrave, Jr. |
| 5,235,238 A | 8/1993 | Nomura et al. |
| 5,236,445 A | 8/1993 | Hayhurst et al. |
| 5,236,461 A | 8/1993 | Forte |
| 5,242,447 A | 9/1993 | Borzone |
| 5,246,441 A | 9/1993 | Ross et al. |
| 5,249,899 A | 10/1993 | Wilson |
| 5,250,053 A | 10/1993 | Snyder |
| 5,258,015 A | 11/1993 | Li et al. |
| 5,258,016 A | 11/1993 | DiPoto et al. |
| 5,258,040 A | 11/1993 | Bruchman et al. |
| 5,261,908 A | 11/1993 | Campbell, Jr. |
| 5,268,001 A | 12/1993 | Nicholson et al. |
| 5,269,160 A | 12/1993 | Wood |
| 5,269,783 A | 12/1993 | Sander |
| 5,269,806 A | 12/1993 | Sardelis et al. |
| 5,269,809 A | 12/1993 | Hayhurst et al. |
| 5,279,311 A | 1/1994 | Snyder |
| 5,281,422 A | 1/1994 | Badylak et al. |
| 5,282,809 A | 2/1994 | Kammerer et al. |
| 5,282,832 A | 2/1994 | Toso et al. |
| 5,282,867 A | 2/1994 | Mikhail |
| 5,285,040 A | 2/1994 | Brandberg et al. |
| 5,290,217 A | 3/1994 | Campos |
| 5,290,243 A | 3/1994 | Chodorow et al. |
| 5,306,301 A | 4/1994 | Graf et al. |
| 5,312,410 A | 5/1994 | Miller et al. |
| 5,312,422 A | 5/1994 | Trott |
| 5,312,438 A | 5/1994 | Johnson |
| 5,314,429 A | 5/1994 | Goble |
| 5,318,566 A | 6/1994 | Miller |
| 5,318,575 A | 6/1994 | Chesterfield et al. |
| 5,318,577 A | 6/1994 | Li |
| 5,318,578 A | 6/1994 | Hasson |
| 5,320,115 A | 6/1994 | Kenna |
| 5,320,626 A | 6/1994 | Schmieding |
| 5,320,633 A | 6/1994 | Allen et al. |
| 5,324,308 A | 6/1994 | Pierce |
| 5,330,489 A | 7/1994 | Green et al. |
| 5,333,625 A | 8/1994 | Klein |

(56) References Cited

U.S. PATENT DOCUMENTS

| | | |
|---|---|---|
| 5,334,204 A | 8/1994 | Clewett et al. |
| 5,336,229 A | 8/1994 | Noda |
| 5,336,231 A | 8/1994 | Adair |
| 5,336,240 A | 8/1994 | Metzler et al. |
| 5,339,870 A | 8/1994 | Green et al. |
| 5,342,369 A | 8/1994 | Harryman, II |
| 5,346,462 A | 9/1994 | Barber |
| 5,350,380 A | 9/1994 | Goble et al. |
| RE34,762 E | 10/1994 | Goble et al. |
| 5,354,298 A | 10/1994 | Lee et al. |
| 5,356,412 A | 10/1994 | Golds et al. |
| 5,356,413 A | 10/1994 | Martins et al. |
| 5,356,417 A | 10/1994 | Golds |
| 5,358,511 A | 10/1994 | Gatturna et al. |
| 5,360,431 A | 11/1994 | Puno et al. |
| 5,362,294 A | 11/1994 | Seitzinger |
| 5,364,400 A | 11/1994 | Rego, Jr. et al. |
| 5,366,461 A | 11/1994 | Blasnik |
| 5,368,599 A | 11/1994 | Hirsch et al. |
| 5,370,661 A | 12/1994 | Branch |
| 5,370,662 A | 12/1994 | Stone et al. |
| 5,372,146 A | 12/1994 | Branch |
| 5,372,604 A | 12/1994 | Trott |
| 5,372,821 A | 12/1994 | Badylak et al. |
| 5,374,268 A | 12/1994 | Sander |
| 5,374,269 A | 12/1994 | Rosenberg |
| 5,379,492 A | 1/1995 | Glesser |
| 5,383,878 A | 1/1995 | Roger et al. |
| 5,383,904 A | 1/1995 | Totakura et al. |
| 5,385,567 A | 1/1995 | Goble |
| 5,391,171 A | 2/1995 | Schmieding |
| 5,391,176 A | 2/1995 | de la Torre |
| 5,391,182 A | 2/1995 | Chin |
| 5,393,302 A | 2/1995 | Clark et al. |
| RE34,871 E | 3/1995 | McGuire et al. |
| 5,397,356 A | 3/1995 | Goble et al. |
| 5,403,328 A | 4/1995 | Shallman |
| 5,403,329 A | 4/1995 | Hinchcliffe |
| 5,403,348 A | 4/1995 | Bonutti |
| 5,405,359 A | 4/1995 | Pierce |
| 5,411,550 A | 5/1995 | Herweck et al. |
| 5,417,691 A | 5/1995 | Hayhurst |
| 5,417,698 A | 5/1995 | Green et al. |
| 5,417,712 A | 5/1995 | Whittaker et al. |
| 5,423,819 A | 6/1995 | Small et al. |
| 5,423,821 A | 6/1995 | Pasque |
| 5,423,823 A | 6/1995 | Schmieding |
| 5,423,860 A | 6/1995 | Lizardi et al. |
| 5,425,733 A | 6/1995 | Schmieding |
| 5,425,766 A | 6/1995 | Bowald et al. |
| 5,433,751 A | 7/1995 | Christel et al. |
| 5,437,680 A | 8/1995 | Yoon |
| 5,437,685 A | 8/1995 | Blasnik |
| 5,439,684 A | 8/1995 | Prewett et al. |
| 5,441,508 A | 8/1995 | Gazielly et al. |
| 5,443,468 A | 8/1995 | Johnson |
| 5,443,482 A | 8/1995 | Stone et al. |
| 5,443,483 A | 8/1995 | Kirsch et al. |
| 5,443,509 A | 8/1995 | Boucher et al. |
| 5,445,833 A | 8/1995 | Badylak et al. |
| 5,447,512 A | 9/1995 | Wilson et al. |
| 5,449,361 A | 9/1995 | Preissman |
| 5,451,203 A | 9/1995 | Lamb |
| 5,454,811 A | 10/1995 | Huebner |
| 5,454,821 A | 10/1995 | Harm et al. |
| 5,456,685 A | 10/1995 | Huebner |
| 5,456,722 A | 10/1995 | McLeod et al. |
| 5,458,601 A | 10/1995 | Young, Jr. et al. |
| 5,458,604 A | 10/1995 | Schmieding |
| 5,462,542 A | 10/1995 | Alesi, Jr. |
| 5,462,560 A | 10/1995 | Stevens |
| 5,464,426 A | 11/1995 | Bonutti |
| 5,464,427 A | 11/1995 | Curtis et al. |
| 5,464,440 A | 11/1995 | Johansson et al. |
| 5,466,237 A | 11/1995 | Byrd, III et al. |
| 5,467,786 A | 11/1995 | Allen et al. |
| 5,470,334 A | 11/1995 | Ross et al. |
| 5,470,337 A | 11/1995 | Moss |
| 5,470,338 A | 11/1995 | Whitfield et al. |
| 5,472,452 A | 12/1995 | Trott |
| 5,474,565 A | 12/1995 | Trott |
| 5,474,568 A | 12/1995 | Scott |
| 5,474,572 A | 12/1995 | Hayhurst |
| 5,478,344 A | 12/1995 | Stone et al. |
| 5,478,345 A | 12/1995 | Stone et al. |
| 5,480,403 A | 1/1996 | Lee et al. |
| 5,480,406 A | 1/1996 | Nolan et al. |
| 5,484,442 A | 1/1996 | Melker et al. |
| 5,486,197 A | 1/1996 | Le et al. |
| 5,490,750 A | 2/1996 | Gundy |
| 5,496,331 A | 3/1996 | Xu et al. |
| 5,496,348 A | 3/1996 | Bonutti |
| 5,500,000 A | 3/1996 | Feagin et al. |
| 5,505,735 A | 4/1996 | Li |
| 5,505,736 A | 4/1996 | Reimels et al. |
| 5,507,754 A | 4/1996 | Green et al. |
| 5,520,691 A | 5/1996 | Branch |
| 5,520,694 A | 5/1996 | Dance et al. |
| 5,520,700 A | 5/1996 | Beyar et al. |
| 5,520,702 A | 5/1996 | Sauer et al. |
| 5,522,817 A | 6/1996 | Sander et al. |
| 5,522,820 A | 6/1996 | Caspari et al. |
| 5,522,843 A | 6/1996 | Zang |
| 5,522,844 A | 6/1996 | Johnson |
| 5,522,845 A | 6/1996 | Wenstrom, Jr. |
| 5,522,846 A | 6/1996 | Bonutti |
| 5,524,946 A | 6/1996 | Thompson |
| 5,527,321 A | 6/1996 | Hinchliffe |
| 5,527,342 A | 6/1996 | Pietrzak et al. |
| 5,527,343 A | 6/1996 | Bonutti |
| 5,531,759 A * | 7/1996 | Kensey et al. ................ 606/213 |
| 5,534,012 A | 7/1996 | Bonutti |
| 5,536,270 A | 7/1996 | Songer et al. |
| 5,540,698 A | 7/1996 | Preissman |
| 5,540,703 A | 7/1996 | Barker, Jr. et al. |
| 5,540,718 A | 7/1996 | Bartlett |
| 5,545,168 A | 8/1996 | Burke |
| 5,545,178 A | 8/1996 | Kensey et al. |
| 5,545,180 A | 8/1996 | Le et al. |
| 5,545,228 A | 8/1996 | Kambin |
| 5,549,613 A | 8/1996 | Goble et al. |
| 5,549,617 A | 8/1996 | Green et al. |
| 5,549,619 A | 8/1996 | Peters et al. |
| 5,549,630 A | 8/1996 | Bonutti |
| 5,549,631 A | 8/1996 | Bonutti |
| 5,562,668 A | 10/1996 | Johnson |
| 5,562,669 A | 10/1996 | McGuire |
| 5,562,683 A | 10/1996 | Chan |
| 5,562,685 A | 10/1996 | Mollenauer et al. |
| 5,562,686 A | 10/1996 | Sauer et al. |
| 5,569,269 A | 10/1996 | Hart et al. |
| 5,569,305 A | 10/1996 | Bonutti |
| 5,570,706 A | 11/1996 | Howell |
| 5,571,090 A | 11/1996 | Sherts |
| 5,571,104 A | 11/1996 | Li |
| 5,571,139 A | 11/1996 | Jenkins, Jr. |
| 5,572,655 A | 11/1996 | Tuljapurkar et al. |
| 5,573,286 A | 11/1996 | Rogozinski |
| 5,573,542 A | 11/1996 | Stevens |
| 5,573,548 A | 11/1996 | Nazre et al. |
| 5,577,299 A | 11/1996 | Thompson et al. |
| 5,578,057 A | 11/1996 | Wenstrom, Jr. |
| 5,584,695 A | 12/1996 | Lal Sachdeva et al. |
| 5,584,835 A | 12/1996 | Greenfield |
| 5,584,836 A | 12/1996 | Ballintyn et al. |
| 5,584,862 A | 12/1996 | Bonutti |
| 5,586,986 A | 12/1996 | Hinchliffe |
| 5,588,575 A | 12/1996 | Davignon |
| 5,591,180 A | 1/1997 | Hinchliffe |
| 5,591,181 A | 1/1997 | Stone et al. |
| 5,591,207 A | 1/1997 | Coleman |
| 5,593,407 A | 1/1997 | Reis et al. |
| 5,593,425 A | 1/1997 | Bonutti et al. |
| 5,601,557 A | 2/1997 | Hayhurst |

(56) References Cited

U.S. PATENT DOCUMENTS

| | | | |
|---|---|---|---|
| 5,601,559 A | 2/1997 | Melker et al. | |
| 5,601,571 A | 2/1997 | Moss | |
| 5,603,716 A | 2/1997 | Morgan et al. | |
| 5,607,429 A | 3/1997 | Hayano et al. | |
| 5,613,971 A | 3/1997 | Lower et al. | |
| 5,618,290 A | 4/1997 | Toy et al. | |
| 5,626,611 A | 5/1997 | Liu et al. | |
| 5,626,614 A | 5/1997 | Hart | |
| 5,628,756 A * | 5/1997 | Barker et al. | 606/139 |
| 5,628,766 A | 5/1997 | Johnson | |
| 5,630,824 A | 5/1997 | Hart | |
| 5,632,748 A | 5/1997 | Beck, Jr. et al. | |
| 5,641,256 A | 6/1997 | Gundy | |
| 5,643,266 A | 7/1997 | Li | |
| 5,643,269 A | 7/1997 | Harle et al. | |
| 5,643,273 A | 7/1997 | Clark | |
| 5,643,295 A | 7/1997 | Yoon | |
| 5,643,319 A | 7/1997 | Green et al. | |
| 5,643,320 A | 7/1997 | Lower et al. | |
| 5,643,321 A | 7/1997 | McDevitt | |
| 5,645,546 A | 7/1997 | Fard | |
| 5,645,547 A | 7/1997 | Coleman | |
| 5,645,568 A | 7/1997 | Chervitz et al. | |
| 5,645,588 A | 7/1997 | Graf et al. | |
| 5,647,874 A | 7/1997 | Hayhurst | |
| 5,649,959 A | 7/1997 | Hannam et al. | |
| 5,649,963 A | 7/1997 | McDevitt | |
| 5,658,289 A | 8/1997 | Boucher et al. | |
| 5,658,299 A | 8/1997 | Hart | |
| 5,658,313 A | 8/1997 | Thal | |
| 5,662,658 A | 9/1997 | Wenstrom, Jr. | |
| 5,662,663 A | 9/1997 | Shallman | |
| 5,662,681 A * | 9/1997 | Nash et al. | 606/213 |
| 5,665,112 A | 9/1997 | Thal | |
| 5,667,513 A | 9/1997 | Torrie et al. | |
| 5,671,695 A | 9/1997 | Schroeder | |
| 5,674,224 A | 10/1997 | Howell et al. | |
| 5,679,723 A | 10/1997 | Cooper et al. | |
| 5,681,334 A | 10/1997 | Evans et al. | |
| 5,681,352 A | 10/1997 | Clancy, III et al. | |
| 5,683,419 A | 11/1997 | Thal | |
| 5,688,284 A | 11/1997 | Chervitz et al. | |
| 5,688,285 A | 11/1997 | Yamada et al. | |
| 5,690,655 A | 11/1997 | Hart et al. | |
| 5,690,676 A | 11/1997 | DiPoto et al. | |
| 5,690,678 A | 11/1997 | Johnson | |
| 5,693,046 A | 12/1997 | Songer et al. | |
| 5,695,497 A | 12/1997 | Stahelin et al. | |
| 5,697,929 A | 12/1997 | Mellinger | |
| 5,699,657 A | 12/1997 | Paulson | |
| 5,702,397 A | 12/1997 | Goble et al. | |
| 5,702,422 A | 12/1997 | Stone | |
| 5,702,462 A | 12/1997 | Oberlander | |
| 5,707,373 A | 1/1998 | Sevrain et al. | |
| 5,709,708 A | 1/1998 | Thal | |
| 5,711,969 A | 1/1998 | Patel et al. | |
| 5,713,005 A | 1/1998 | Proebsting | |
| 5,713,897 A | 2/1998 | Goble et al. | |
| 5,713,904 A | 2/1998 | Errico et al. | |
| 5,713,905 A | 2/1998 | Goble et al. | |
| 5,713,921 A | 2/1998 | Bonutti | |
| 5,716,359 A | 2/1998 | Ojima et al. | |
| 5,716,397 A * | 2/1998 | Myers | 623/2.36 |
| 5,718,717 A | 2/1998 | Bonutti | |
| 5,720,747 A | 2/1998 | Burke | |
| 5,720,765 A | 2/1998 | Thal | |
| 5,720,766 A | 2/1998 | Zang et al. | |
| 5,722,976 A | 3/1998 | Brown | |
| 5,725,529 A | 3/1998 | Nicholson et al. | |
| 5,725,549 A | 3/1998 | Lam | |
| 5,725,556 A | 3/1998 | Moser et al. | |
| 5,725,581 A | 3/1998 | Brånemark | |
| 5,725,582 A | 3/1998 | Bevan et al. | |
| 5,726,722 A | 3/1998 | Uehara et al. | |
| 5,728,107 A | 3/1998 | Zlock et al. | |
| 5,728,109 A | 3/1998 | Schulze et al. | |
| 5,728,136 A | 3/1998 | Thal | |
| 5,733,293 A | 3/1998 | Scirica et al. | |
| 5,733,306 A | 3/1998 | Bonutti | |
| 5,733,307 A | 3/1998 | Dinsdale | |
| 5,735,875 A | 4/1998 | Bonutti et al. | |
| 5,741,259 A | 4/1998 | Chan | |
| 5,741,260 A | 4/1998 | Songer et al. | |
| 5,741,281 A | 4/1998 | Martin et al. | |
| 5,743,912 A | 4/1998 | Lahille et al. | |
| 5,746,751 A | 5/1998 | Sherts | |
| 5,746,752 A | 5/1998 | Burkhart | |
| 5,746,754 A | 5/1998 | Chan | |
| 5,749,898 A | 5/1998 | Schulze et al. | |
| 5,755,729 A | 5/1998 | de la Torre et al. | |
| 5,755,791 A | 5/1998 | Whitson et al. | |
| 5,766,176 A | 6/1998 | Duncan | |
| 5,766,218 A | 6/1998 | Arnott | |
| 5,766,250 A | 6/1998 | Chervitz et al. | |
| 5,769,894 A | 6/1998 | Ferragamo | |
| 5,769,899 A | 6/1998 | Schwartz et al. | |
| 5,772,673 A | 6/1998 | Cuny et al. | |
| 5,776,196 A | 7/1998 | Matsuzaki et al. | |
| 5,782,845 A | 7/1998 | Shewchuk | |
| 5,782,862 A | 7/1998 | Bonutti | |
| 5,782,864 A | 7/1998 | Lizardi | |
| 5,782,866 A | 7/1998 | Wenstrom, Jr. | |
| 5,785,714 A | 7/1998 | Morgan et al. | |
| 5,792,142 A | 8/1998 | Galitzer | |
| 5,792,149 A | 8/1998 | Sherts et al. | |
| 5,796,127 A | 8/1998 | Hayafuji et al. | |
| 5,797,915 A | 8/1998 | Pierson, III et al. | |
| 5,797,916 A | 8/1998 | McDowell | |
| 5,797,928 A | 8/1998 | Kogasaka | |
| 5,800,407 A | 9/1998 | Eldor et al. | |
| 5,810,824 A | 9/1998 | Chan | |
| 5,810,848 A | 9/1998 | Hayhurst | |
| 5,814,056 A | 9/1998 | Prosst et al. | |
| 5,814,069 A | 9/1998 | Schulze et al. | |
| 5,814,070 A | 9/1998 | Borzone et al. | |
| 5,814,072 A | 9/1998 | Bonutti | |
| 5,814,073 A | 9/1998 | Bonutti | |
| 5,823,980 A | 10/1998 | Kopfer | |
| 5,824,011 A | 10/1998 | Stone et al. | |
| 5,824,066 A * | 10/1998 | Gross | 623/2.36 |
| 5,830,234 A | 11/1998 | Wojciechowicz et al. | |
| 5,843,084 A | 12/1998 | Hart et al. | |
| 5,845,645 A | 12/1998 | Bonutti | |
| 5,846,254 A | 12/1998 | Schulze et al. | |
| 5,848,983 A | 12/1998 | Basaj et al. | |
| 5,849,012 A | 12/1998 | Abboudi | |
| 5,860,973 A | 1/1999 | Michelson | |
| 5,860,978 A | 1/1999 | McDevitt et al. | |
| 5,868,740 A | 2/1999 | LeVeen et al. | |
| 5,868,748 A | 2/1999 | Burke | |
| 5,868,789 A | 2/1999 | Huebner | |
| 5,871,484 A | 2/1999 | Spievack et al. | |
| 5,871,486 A | 2/1999 | Huebner et al. | |
| 5,871,490 A | 2/1999 | Schulze et al. | |
| 5,885,294 A | 3/1999 | Pedlick et al. | |
| 5,891,168 A | 4/1999 | Thal | |
| 5,893,592 A | 4/1999 | Schulze et al. | |
| 5,895,395 A | 4/1999 | Yeung | |
| 5,897,564 A | 4/1999 | Schulze et al. | |
| 5,897,574 A | 4/1999 | Bonutti | |
| 5,899,902 A | 5/1999 | Brown et al. | |
| 5,899,938 A | 5/1999 | Sklar et al. | |
| 5,908,421 A | 6/1999 | Beger et al. | |
| 5,908,436 A | 6/1999 | Cuschieri et al. | |
| 5,910,148 A | 6/1999 | Reimels et al. | |
| 5,911,721 A | 6/1999 | Nicholson et al. | |
| 5,918,604 A | 7/1999 | Whelan | |
| 5,921,986 A | 7/1999 | Bonutti | |
| 5,925,008 A | 7/1999 | Douglas | |
| 5,928,231 A | 7/1999 | Klein et al. | |
| 5,928,267 A | 7/1999 | Bonutti et al. | |
| RE36,289 E | 8/1999 | Le et al. | |
| 5,931,838 A | 8/1999 | Vito | |
| 5,931,844 A | 8/1999 | Thompson et al. | |

(56) References Cited

U.S. PATENT DOCUMENTS

| | | |
|---|---|---|
| 5,931,869 A | 8/1999 | Boucher et al. |
| 5,935,119 A | 8/1999 | Guy et al. |
| 5,935,133 A | 8/1999 | Wagner et al. |
| 5,935,149 A | 8/1999 | Ek |
| 5,938,668 A | 8/1999 | Scirica et al. |
| 5,941,439 A | 8/1999 | Kammerer et al. |
| 5,941,900 A | 8/1999 | Bonutti |
| 5,944,739 A | 8/1999 | Zlock et al. |
| 5,946,783 A | 9/1999 | Plociennik et al. |
| 5,947,915 A | 9/1999 | Thibodo, Jr. |
| 5,947,982 A | 9/1999 | Duran |
| 5,947,999 A | 9/1999 | Groiso |
| 5,948,002 A | 9/1999 | Bonutti |
| 5,951,559 A | 9/1999 | Burkhart |
| 5,951,560 A | 9/1999 | Simon et al. |
| 5,954,747 A | 9/1999 | Clark |
| 5,957,953 A | 9/1999 | DiPoto et al. |
| 5,961,520 A | 10/1999 | Beck, Jr. et al. |
| 5,961,521 A | 10/1999 | Roger et al. |
| 5,961,524 A | 10/1999 | Crombie |
| 5,964,764 A | 10/1999 | West, Jr. et al. |
| 5,964,767 A | 10/1999 | Tapia et al. |
| 5,964,769 A | 10/1999 | Wagner et al. |
| 5,964,783 A | 10/1999 | Grafton et al. |
| 5,968,045 A | 10/1999 | Frazier |
| 5,968,047 A | 10/1999 | Reed |
| 5,968,077 A | 10/1999 | Wojciechowicz et al. |
| 5,970,697 A | 10/1999 | Jacobs et al. |
| 5,972,006 A | 10/1999 | Sciaino, Jr. |
| 5,976,125 A | 11/1999 | Graham |
| 5,976,127 A | 11/1999 | Lax |
| 5,980,473 A | 11/1999 | Korakianitis et al. |
| 5,980,524 A | 11/1999 | Justin et al. |
| 5,980,539 A | 11/1999 | Kontos |
| 5,980,558 A | 11/1999 | Wiley |
| 5,980,559 A | 11/1999 | Bonutti |
| 5,989,252 A | 11/1999 | Fumex |
| 5,989,256 A | 11/1999 | Kuslich et al. |
| 5,989,282 A | 11/1999 | Bonutti |
| 5,993,452 A | 11/1999 | Vandewalle |
| 5,993,476 A | 11/1999 | Groiso |
| 5,997,542 A | 12/1999 | Burke |
| 5,997,552 A | 12/1999 | Person et al. |
| 5,997,575 A | 12/1999 | Whitson et al. |
| 6,001,100 A | 12/1999 | Sherman et al. |
| 6,001,106 A | 12/1999 | Ryan et al. |
| 6,007,538 A | 12/1999 | Levin |
| 6,007,567 A | 12/1999 | Bonutti |
| 6,010,525 A | 1/2000 | Bonutti et al. |
| 6,016,727 A | 1/2000 | Morgan |
| 6,019,767 A | 2/2000 | Howell |
| 6,022,352 A | 2/2000 | Vandewalle |
| 6,022,373 A | 2/2000 | Li |
| 6,024,758 A | 2/2000 | Thal |
| 6,027,523 A | 2/2000 | Schmieding |
| 6,030,410 A | 2/2000 | Zurbrugg |
| 6,033,429 A | 3/2000 | Magovern |
| 6,033,430 A | 3/2000 | Bonutti |
| 6,039,753 A | 3/2000 | Meislin |
| 6,041,485 A | 3/2000 | Pedlick et al. |
| 6,042,601 A | 3/2000 | Smith |
| 6,045,551 A | 4/2000 | Bonutti |
| 6,045,571 A | 4/2000 | Hill et al. |
| 6,045,572 A | 4/2000 | Johnson et al. |
| 6,045,573 A | 4/2000 | Wenstrom, Jr. et al. |
| 6,045,574 A | 4/2000 | Thal |
| 6,047,826 A | 4/2000 | Kalinski et al. |
| 6,048,343 A | 4/2000 | Mathis et al. |
| 6,051,006 A | 4/2000 | Shluzas et al. |
| 6,051,007 A | 4/2000 | Hogendijk et al. |
| 6,053,916 A | 4/2000 | Moore |
| 6,053,921 A | 4/2000 | Wagner et al. |
| 6,056,752 A | 5/2000 | Roger |
| 6,056,772 A | 5/2000 | Bonutti |
| 6,056,773 A | 5/2000 | Bonutti |
| 6,059,817 A | 5/2000 | Bonutti et al. |
| 6,059,818 A | 5/2000 | Johnson et al. |
| 6,062,344 A | 5/2000 | Okabe et al. |
| 6,066,173 A | 5/2000 | McKernan et al. |
| 6,068,648 A | 5/2000 | Cole et al. |
| 6,071,305 A | 6/2000 | Brown et al. |
| 6,074,403 A | 6/2000 | Nord |
| 6,077,277 A | 6/2000 | Mollenauer et al. |
| 6,077,292 A | 6/2000 | Bonutti |
| 6,080,185 A | 6/2000 | Johnson et al. |
| 6,086,591 A | 7/2000 | Bojarski |
| 6,086,592 A | 7/2000 | Rosenberg et al. |
| 6,086,608 A | 7/2000 | Ek et al. |
| 6,093,200 A | 7/2000 | Liu et al. |
| 6,096,060 A | 8/2000 | Fitts et al. |
| 6,099,527 A | 8/2000 | Hochschuler et al. |
| 6,099,530 A | 8/2000 | Simonian et al. |
| 6,099,568 A | 8/2000 | Simonian et al. |
| 6,102,934 A | 8/2000 | Li |
| 6,106,545 A | 8/2000 | Egan |
| 6,110,128 A | 8/2000 | Andelin et al. |
| 6,113,604 A | 9/2000 | Whittaker et al. |
| 6,117,160 A | 9/2000 | Bonutti |
| 6,117,162 A | 9/2000 | Schmieding et al. |
| 6,123,710 A | 9/2000 | Pinczewski et al. |
| 6,132,433 A | 10/2000 | Whelan |
| 6,132,437 A | 10/2000 | Omurtag et al. |
| 6,139,565 A | 10/2000 | Stone et al. |
| RE36,974 E | 11/2000 | Bonutti |
| 6,143,017 A | 11/2000 | Thal |
| 6,146,406 A | 11/2000 | Shluzas et al. |
| 6,146,408 A | 11/2000 | Bartlett |
| 6,149,653 A | 11/2000 | Deslauriers |
| 6,149,669 A | 11/2000 | Li |
| 6,152,928 A | 11/2000 | Wenstrom, Jr. |
| 6,152,934 A | 11/2000 | Harper et al. |
| 6,152,936 A | 11/2000 | Christy et al. |
| 6,152,949 A | 11/2000 | Bonutti |
| 6,156,039 A | 12/2000 | Thal |
| 6,156,056 A | 12/2000 | Kearns et al. |
| 6,159,234 A | 12/2000 | Bonutti et al. |
| 6,165,203 A | 12/2000 | Krebs |
| 6,168,598 B1 | 1/2001 | Martello |
| 6,168,628 B1 | 1/2001 | Huebner |
| 6,179,840 B1 | 1/2001 | Bowman |
| 6,183,461 B1 | 2/2001 | Matsuura et al. |
| 6,187,025 B1 | 2/2001 | Machek |
| 6,190,401 B1 | 2/2001 | Green et al. |
| 6,190,411 B1 | 2/2001 | Lo et al. |
| 6,193,754 B1 | 2/2001 | Seedhom |
| 6,200,318 B1 | 3/2001 | Har-Shai et al. |
| 6,200,329 B1 | 3/2001 | Fung et al. |
| 6,200,330 B1 | 3/2001 | Benderev et al. |
| 6,203,556 B1 | 3/2001 | Evans et al. |
| 6,203,565 B1 | 3/2001 | Bonutti et al. |
| 6,203,572 B1 | 3/2001 | Johnson et al. |
| 6,206,883 B1 | 3/2001 | Tunc |
| 6,210,376 B1 | 4/2001 | Grayson |
| 6,214,007 B1 | 4/2001 | Anderson |
| 6,214,012 B1 | 4/2001 | Karpman et al. |
| 6,217,580 B1 | 4/2001 | Levin |
| 6,221,107 B1 | 4/2001 | Steiner et al. |
| 6,228,096 B1 | 5/2001 | Marchand |
| 6,231,592 B1 | 5/2001 | Bonutti et al. |
| 6,235,057 B1 | 5/2001 | Roger et al. |
| 6,238,395 B1 | 5/2001 | Bonutti |
| 6,241,734 B1 | 6/2001 | Scribner et al. |
| 6,241,747 B1 | 6/2001 | Ruff |
| 6,241,771 B1 | 6/2001 | Gresser et al. |
| 6,245,081 B1 | 6/2001 | Bowman et al. |
| 6,254,604 B1 | 7/2001 | Howell |
| 6,258,091 B1 | 7/2001 | Sevrain et al. |
| 6,267,766 B1 | 7/2001 | Burkhart |
| 6,269,716 B1 | 8/2001 | Amis |
| 6,270,518 B1 | 8/2001 | Pedlick et al. |
| 6,273,890 B1 | 8/2001 | Frazier |
| 6,280,474 B1 | 8/2001 | Cassidy et al. |
| 6,283,973 B1 | 9/2001 | Hubbard et al. |
| 6,283,996 B1 | 9/2001 | Chervitz et al. |

(56) References Cited

U.S. PATENT DOCUMENTS

| | | |
|---|---|---|
| 6,287,307 B1 | 9/2001 | Abboudi |
| 6,287,325 B1 | 9/2001 | Bonutti |
| 6,293,961 B2 | 9/2001 | Schwartz et al. |
| 6,296,659 B1 | 10/2001 | Foerster |
| 6,299,615 B1 | 10/2001 | Huebner |
| 6,302,888 B1 | 10/2001 | Mellinger et al. |
| 6,302,899 B1 | 10/2001 | Johnson et al. |
| 6,306,156 B1 | 10/2001 | Clark |
| 6,306,158 B1 | 10/2001 | Bartlett |
| 6,306,159 B1 | 10/2001 | Schwartz et al. |
| 6,309,405 B1 | 10/2001 | Bonutti |
| 6,312,448 B1 | 11/2001 | Bonutti |
| 6,315,788 B1 | 11/2001 | Roby |
| 6,319,271 B1 | 11/2001 | Schwartz et al. |
| 6,328,758 B1 | 12/2001 | Tornier et al. |
| 6,342,060 B1 | 1/2002 | Adams |
| 6,343,531 B2 | 2/2002 | Amis |
| 6,355,066 B1 | 3/2002 | Kim |
| 6,358,270 B1 | 3/2002 | Lemer |
| 6,364,897 B1 | 4/2002 | Bonutti |
| 6,368,322 B1 | 4/2002 | Luks et al. |
| 6,368,326 B1 | 4/2002 | Dakin et al. |
| 6,368,343 B1 | 4/2002 | Bonutti et al. |
| 6,371,124 B1 | 4/2002 | Whelan |
| 6,379,361 B1 | 4/2002 | Beck, Jr. et al. |
| 6,383,190 B1 | 5/2002 | Preissman |
| 6,383,199 B2 | 5/2002 | Carter et al. |
| 6,387,113 B1 | 5/2002 | Hawkins et al. |
| 6,387,129 B2 | 5/2002 | Rieser et al. |
| 6,391,030 B1 | 5/2002 | Wagner et al. |
| 6,398,785 B2 | 6/2002 | Carchidi et al. |
| 6,406,479 B1 | 6/2002 | Justin et al. |
| 6,409,743 B1 | 6/2002 | Fenton, Jr. |
| 6,413,260 B1 | 7/2002 | Berrevoets et al. |
| 6,423,073 B2 | 7/2002 | Bowman |
| 6,423,088 B1 | 7/2002 | Fenton, Jr. |
| 6,428,562 B2 | 8/2002 | Bonutti |
| 6,432,123 B2 | 8/2002 | Schwartz et al. |
| 6,436,123 B1 | 8/2002 | Magovern |
| 6,436,124 B1 | 8/2002 | Anderson et al. |
| 6,440,134 B1 | 8/2002 | Zaccherotti et al. |
| 6,440,136 B1 | 8/2002 | Gambale et al. |
| 6,447,516 B1 | 9/2002 | Bonutti |
| 6,451,030 B2 | 9/2002 | Li et al. |
| 6,454,768 B1 | 9/2002 | Jackson |
| 6,458,134 B1 | 10/2002 | Songer et al. |
| 6,461,373 B2 | 10/2002 | Wyman et al. |
| 6,464,713 B2 | 10/2002 | Bonutti |
| 6,468,293 B2 | 10/2002 | Bonutti et al. |
| 6,471,707 B1 | 10/2002 | Miller et al. |
| 6,475,230 B1 | 11/2002 | Bonutti et al. |
| 6,478,753 B2 | 11/2002 | Reay-Young |
| 6,482,210 B1 | 11/2002 | Skiba et al. |
| 6,485,504 B1 | 11/2002 | Johnson et al. |
| 6,491,714 B1 | 12/2002 | Bennett |
| 6,497,901 B1 | 12/2002 | Royer |
| 6,500,184 B1 | 12/2002 | Chan et al. |
| 6,500,195 B2 | 12/2002 | Bonutti |
| RE37,963 E | 1/2003 | Thal |
| 6,503,267 B2 | 1/2003 | Bonutti et al. |
| 6,506,190 B1 | 1/2003 | Walshe |
| 6,508,820 B2 | 1/2003 | Bales |
| 6,508,821 B1 | 1/2003 | Schwartz et al. |
| 6,508,830 B2 | 1/2003 | Steiner |
| 6,511,498 B1 | 1/2003 | Fumex |
| 6,511,499 B2 | 1/2003 | Schmieding et al. |
| 6,517,542 B1 | 2/2003 | Papay et al. |
| 6,517,552 B1 | 2/2003 | Nord et al. |
| 6,517,564 B1 | 2/2003 | Grafton et al. |
| 6,517,578 B2 | 2/2003 | Hein |
| 6,517,579 B1 | 2/2003 | Paulos et al. |
| 6,520,964 B2 | 2/2003 | Tallarida et al. |
| 6,520,980 B1 | 2/2003 | Foerster |
| 6,524,317 B1 | 2/2003 | Ritchart et al. |
| 6,527,777 B2 | 3/2003 | Justin |
| 6,527,794 B1 | 3/2003 | McDevitt et al. |
| 6,527,795 B1 | 3/2003 | Lizardi |
| 6,533,795 B1 | 3/2003 | Tran et al. |
| 6,533,802 B2 | 3/2003 | Bojarski et al. |
| 6,537,319 B2 | 3/2003 | Whelan |
| 6,540,750 B2 | 4/2003 | Burkhart |
| 6,540,769 B1 | 4/2003 | Miller, III |
| 6,540,770 B1 | 4/2003 | Tornier et al. |
| 6,540,783 B1 | 4/2003 | Whittaker et al. |
| 6,544,281 B2 | 4/2003 | ElAttrache et al. |
| 6,547,564 B1 | 4/2003 | Hansson et al. |
| 6,547,778 B1 | 4/2003 | Sklar et al. |
| 6,547,800 B2 | 4/2003 | Foerster et al. |
| 6,551,330 B1 | 4/2003 | Bain et al. |
| 6,551,343 B1 | 4/2003 | Tormala et al. |
| 6,553,802 B2 | 4/2003 | Jacob et al. |
| 6,554,830 B1 | 4/2003 | Chappius |
| 6,554,852 B1 | 4/2003 | Oberlander |
| 6,554,862 B2 | 4/2003 | Hays et al. |
| 6,558,389 B2 | 5/2003 | Clark et al. |
| 6,562,071 B2 | 5/2003 | Jarvinen et al. |
| 6,565,572 B2 | 5/2003 | Chappius |
| 6,565,573 B1 | 5/2003 | Ferrante et al. |
| 6,569,186 B1 | 5/2003 | Winters et al. |
| 6,569,187 B1 | 5/2003 | Bonutti et al. |
| 6,572,635 B1 | 6/2003 | Bonutti |
| 6,575,925 B1 | 6/2003 | Noble |
| 6,579,295 B1 | 6/2003 | Supinski |
| 6,582,453 B1 | 6/2003 | Tran et al. |
| 6,585,730 B1 | 7/2003 | Foerster |
| 6,585,740 B2 | 7/2003 | Schlapfer et al. |
| 6,585,750 B2 | 7/2003 | Bonutti et al. |
| 6,589,245 B1 | 7/2003 | Weiler et al. |
| 6,589,246 B1 | 7/2003 | Hack et al. |
| 6,592,609 B1 | 7/2003 | Bonutti |
| 6,595,911 B2 | 7/2003 | LoVuolo |
| 6,599,289 B1 | 7/2003 | Bojarski et al. |
| 6,599,319 B2 | 7/2003 | Knudsen et al. |
| 6,605,096 B1 | 8/2003 | Ritchart |
| 6,607,548 B2 | 8/2003 | Pohjonen et al. |
| 6,610,079 B1 | 8/2003 | Li et al. |
| 6,613,018 B2 | 9/2003 | Bagga et al. |
| 6,616,694 B1 | 9/2003 | Hart |
| 6,620,166 B1 | 9/2003 | Wenstrom, Jr. et al. |
| 6,620,185 B1 | 9/2003 | Harvie et al. |
| 6,620,195 B2 | 9/2003 | Goble et al. |
| 6,620,329 B2 | 9/2003 | Rosen et al. |
| 6,620,349 B1 | 9/2003 | Lopez |
| 6,623,492 B1 | 9/2003 | Berube et al. |
| 6,623,524 B2 | 9/2003 | Schmieding |
| 6,626,910 B1 | 9/2003 | Hugues et al. |
| 6,626,919 B1 | 9/2003 | Swanstrom |
| 6,629,977 B1 | 10/2003 | Wolf |
| 6,632,245 B2 | 10/2003 | Kim |
| 6,635,073 B2 | 10/2003 | Bonutti |
| 6,638,279 B2 | 10/2003 | Bonutti |
| 6,638,312 B2 | 10/2003 | Plouhar et al. |
| 6,641,596 B1 | 11/2003 | Lizardi |
| 6,641,597 B2 | 11/2003 | Dreyfuss et al. |
| 6,645,227 B2 | 11/2003 | Fallin et al. |
| 6,648,921 B2 | 11/2003 | Anderson et al. |
| 6,652,450 B2 | 11/2003 | Neisz et al. |
| 6,652,560 B1 | 11/2003 | Gerke et al. |
| 6,652,562 B2 | 11/2003 | Collier et al. |
| 6,652,563 B2 | 11/2003 | Dreyfuss |
| 6,656,182 B1 | 12/2003 | Hayhurst |
| 6,656,183 B2 | 12/2003 | Colleran et al. |
| 6,658,182 B1 | 12/2003 | Gonthier et al. |
| 6,660,008 B1 | 12/2003 | Foerster et al. |
| 6,660,022 B1 | 12/2003 | Li et al. |
| 6,663,634 B2 | 12/2003 | Ahrens et al. |
| 6,663,656 B2 | 12/2003 | Schmieding et al. |
| 6,666,868 B2 | 12/2003 | Fallin |
| 6,666,877 B2 | 12/2003 | Morgan et al. |
| 6,679,889 B1 | 1/2004 | West, Jr. et al. |
| 6,682,533 B1 | 1/2004 | Dinsdale et al. |
| 6,682,549 B2 | 1/2004 | Bartlett |
| 6,685,728 B2 | 2/2004 | Sinnott et al. |
| 6,689,137 B2 | 2/2004 | Reed |

(56) References Cited

U.S. PATENT DOCUMENTS

| | | |
|---|---|---|
| 6,689,153 B1 | 2/2004 | Skiba |
| 6,689,154 B2 | 2/2004 | Bartlett |
| 6,692,499 B2 | 2/2004 | Tormala et al. |
| 6,692,516 B2 | 2/2004 | West, Jr. et al. |
| 6,712,849 B2 | 3/2004 | Re et al. |
| 6,716,224 B2 | 4/2004 | Singhatat |
| 6,716,957 B2 | 4/2004 | Tunc |
| 6,730,092 B2 | 5/2004 | Songer |
| 6,730,124 B2 | 5/2004 | Steiner |
| 6,736,799 B1 | 5/2004 | Erbe et al. |
| 6,737,053 B1 | 5/2004 | Goh et al. |
| 6,746,483 B1 | 6/2004 | Bojarski et al. |
| 6,752,810 B1 | 6/2004 | Gao et al. |
| 6,752,831 B2 | 6/2004 | Sybert et al. |
| 6,755,836 B1 | 6/2004 | Lewis |
| 6,761,722 B2 | 7/2004 | Cole et al. |
| 6,761,739 B2 | 7/2004 | Shepard |
| 6,767,037 B2 | 7/2004 | Wenstrom, Jr. |
| 6,770,076 B2 | 8/2004 | Foerster |
| 6,770,084 B1 | 8/2004 | Bain et al. |
| 6,773,450 B2 | 8/2004 | Leung et al. |
| 6,779,701 B2 | 8/2004 | Bailly et al. |
| 6,780,190 B2 | 8/2004 | Maroney |
| 6,780,198 B1 | 8/2004 | Gregoire et al. |
| 6,802,862 B1 | 10/2004 | Roger et al. |
| 6,808,502 B2 | 10/2004 | Nguyen et al. |
| 6,808,526 B1 | 10/2004 | Magerl et al. |
| 6,814,741 B2 | 11/2004 | Bowman et al. |
| 6,830,572 B2 | 12/2004 | McDevitt et al. |
| 6,833,005 B1 | 12/2004 | Mantas et al. |
| 6,840,953 B2 | 1/2005 | Martinek |
| 6,860,885 B2 | 3/2005 | Bonutti |
| 6,860,895 B1 | 3/2005 | Akerfeldt et al. |
| 6,863,671 B1 | 3/2005 | Strobel et al. |
| 6,872,040 B2 | 3/2005 | Deeg et al. |
| 6,872,210 B2 | 3/2005 | Hearn |
| 6,875,216 B2 | 4/2005 | Wolf |
| 6,884,249 B2 | 4/2005 | May et al. |
| 6,887,259 B2 | 5/2005 | Lizardi |
| 6,887,271 B2 | 5/2005 | Justin et al. |
| 6,890,354 B2 | 5/2005 | Steiner et al. |
| 6,893,448 B2 | 5/2005 | O'Quinn et al. |
| 6,896,686 B2 | 5/2005 | Weber |
| 6,899,722 B2 | 5/2005 | Bonutti |
| 6,902,573 B2 | 6/2005 | Strobel et al. |
| 6,905,513 B1 | 6/2005 | Metzger |
| 6,908,466 B1 | 6/2005 | Bonutti et al. |
| 6,916,292 B2 | 7/2005 | Morawski et al. |
| 6,916,321 B2 | 7/2005 | TenHuisen et al. |
| 6,921,402 B2 | 7/2005 | Contiliano et al. |
| 6,923,823 B1 | 8/2005 | Bartlett et al. |
| 6,923,824 B2 | 8/2005 | Morgan et al. |
| 6,939,379 B2 | 9/2005 | Sklar |
| 6,949,102 B2 | 9/2005 | Andrews |
| 6,951,565 B2 | 10/2005 | Keane et al. |
| 6,966,887 B1 | 11/2005 | Chin |
| 6,966,916 B2 | 11/2005 | Kumar |
| 6,969,391 B1 | 11/2005 | Gazzani |
| 6,969,398 B2 | 11/2005 | Stevens et al. |
| 6,972,027 B2 | 12/2005 | Fallin et al. |
| 6,980,903 B2 | 12/2005 | Daniels et al. |
| 6,986,781 B2 | 1/2006 | Smith |
| 6,989,034 B2 | 1/2006 | Hammer et al. |
| 6,994,725 B1 | 2/2006 | Goble |
| 7,001,429 B2 | 2/2006 | Ferguson |
| 7,004,959 B2 | 2/2006 | Bonutti |
| 7,008,451 B2 | 3/2006 | Justin et al. |
| 7,048,754 B2 * | 5/2006 | Martin et al. ............ 606/232 |
| 7,052,499 B2 | 5/2006 | Steger et al. |
| 7,066,942 B2 | 6/2006 | Treace |
| 7,066,944 B2 | 6/2006 | Laufer et al. |
| 7,081,126 B2 | 7/2006 | McDevitt et al. |
| 7,087,064 B1 | 8/2006 | Hyde |
| 7,097,654 B1 | 8/2006 | Freedland |
| 7,105,010 B2 | 9/2006 | Hart et al. |
| 7,112,221 B2 | 9/2006 | Harris et al. |
| 7,118,578 B2 | 10/2006 | West, Jr. et al. |
| 7,118,583 B2 | 10/2006 | O'Quinn et al. |
| 7,125,421 B2 * | 10/2006 | Tremulis et al. ............ 623/2.37 |
| 7,131,467 B2 | 11/2006 | Gao et al. |
| 7,137,996 B2 | 11/2006 | Steiner et al. |
| 7,141,066 B2 | 11/2006 | Steiner et al. |
| 7,144,414 B2 | 12/2006 | Harvie et al. |
| 7,153,127 B2 | 12/2006 | Struble et al. |
| 7,153,307 B2 | 12/2006 | Scribner et al. |
| 7,153,312 B1 | 12/2006 | Torrie et al. |
| 7,153,327 B1 | 12/2006 | Metzger |
| 7,160,285 B2 | 1/2007 | Sklar et al. |
| 7,160,333 B2 | 1/2007 | Plouhar et al. |
| 7,172,626 B1 | 2/2007 | Andrews |
| 7,201,722 B2 | 4/2007 | Krueger |
| 7,255,675 B2 | 8/2007 | Gertner et al. |
| 7,255,700 B2 | 8/2007 | Kaiser et al. |
| 7,255,715 B2 | 8/2007 | Metzger |
| 7,261,716 B2 | 8/2007 | Strobel et al. |
| 7,264,634 B2 | 9/2007 | Schmieding |
| 7,285,124 B2 | 10/2007 | Foerster |
| 7,303,577 B1 | 12/2007 | Dean |
| 7,306,417 B2 | 12/2007 | Dorstewitz |
| 7,309,355 B2 | 12/2007 | Donnelly et al. |
| 7,326,222 B2 | 2/2008 | Dreyfuss et al. |
| 7,329,272 B2 | 2/2008 | Burkhart et al. |
| 7,361,179 B2 | 4/2008 | Rousseau et al. |
| 7,377,845 B2 | 5/2008 | Stewart et al. |
| 7,390,329 B2 | 6/2008 | Westra et al. |
| 7,390,332 B2 | 6/2008 | Selvitelli et al. |
| 7,399,018 B1 | 7/2008 | Khachaturian |
| 7,442,210 B2 | 10/2008 | Segal et al. |
| 7,465,308 B2 | 12/2008 | Sikora et al. |
| 7,468,074 B2 | 12/2008 | Caborn et al. |
| 7,494,506 B2 | 2/2009 | Brulez et al. |
| D587,807 S | 3/2009 | Wolf et al. |
| 7,513,910 B2 | 4/2009 | Buskirk et al. |
| 7,572,298 B2 | 8/2009 | Roller et al. |
| 7,578,825 B2 | 8/2009 | Huebner |
| 7,585,311 B2 | 9/2009 | Green et al. |
| 7,597,705 B2 | 10/2009 | Forsberg et al. |
| 7,601,165 B2 | 10/2009 | Stone |
| 7,604,636 B1 | 10/2009 | Walters et al. |
| 7,608,092 B1 | 10/2009 | Schaffhausen |
| 7,608,098 B1 | 10/2009 | Stone et al. |
| 7,615,076 B2 | 11/2009 | Cauthen, III et al. |
| 7,621,937 B2 | 11/2009 | Pipenhagen et al. |
| 7,632,287 B2 | 12/2009 | Baker et al. |
| 7,651,509 B2 | 1/2010 | Bojarski et al. |
| 7,658,750 B2 | 2/2010 | Li |
| 7,658,751 B2 | 2/2010 | Stone et al. |
| 7,670,279 B2 | 3/2010 | Gertner |
| 7,678,123 B2 | 3/2010 | Chanduszko |
| 7,695,493 B2 | 4/2010 | Saadat et al. |
| 7,731,732 B2 * | 6/2010 | Ken ............ 606/213 |
| 7,736,379 B2 | 6/2010 | Ewers et al. |
| 7,749,250 B2 * | 7/2010 | Stone et al. ............ 606/232 |
| 7,758,594 B2 | 7/2010 | Lamson et al. |
| 7,758,611 B2 * | 7/2010 | Kato ............ 606/213 |
| 7,776,041 B1 | 8/2010 | Walters |
| 7,803,173 B2 | 9/2010 | Burkhart et al. |
| 7,819,895 B2 | 10/2010 | Ginn et al. |
| 7,828,850 B2 | 11/2010 | Cauthen, III et al. |
| 7,857,830 B2 | 12/2010 | Stone et al. |
| 7,867,264 B2 | 1/2011 | McDevitt et al. |
| 7,875,058 B2 | 1/2011 | Holmes, Jr. |
| 7,887,586 B2 | 2/2011 | Linares |
| 7,905,903 B2 | 3/2011 | Stone et al. |
| 7,905,904 B2 | 3/2011 | Stone et al. |
| 7,909,851 B2 | 3/2011 | Stone et al. |
| 7,938,847 B2 | 5/2011 | Fanton et al. |
| 7,959,650 B2 | 6/2011 | Kaiser et al. |
| 7,981,140 B2 | 7/2011 | Burkhart |
| 7,998,203 B2 | 8/2011 | Blum |
| 8,062,334 B2 | 11/2011 | Green et al. |
| 8,075,574 B2 | 12/2011 | May et al. |
| 8,088,130 B2 | 1/2012 | Kaiser et al. |
| 8,114,127 B2 | 2/2012 | West, Jr. |

(56) References Cited

U.S. PATENT DOCUMENTS

| | | |
|---|---|---|
| 8,114,128 B2 | 2/2012 | Cauldwell et al. |
| 8,118,835 B2 | 2/2012 | Weisel et al. |
| 8,118,836 B2 | 2/2012 | Denham et al. |
| 8,128,658 B2 | 3/2012 | Kaiser et al. |
| 8,137,382 B2 | 3/2012 | Denham et al. |
| 8,162,997 B2 | 4/2012 | Struhl |
| 8,167,906 B2 | 5/2012 | Cauldwell et al. |
| 8,221,454 B2 | 7/2012 | Schaffhausen |
| 8,231,654 B2 | 7/2012 | Kaiser et al. |
| 8,251,998 B2 | 8/2012 | Hoeppner et al. |
| 8,252,022 B2 * | 8/2012 | Holman et al. ............... 606/213 |
| 8,273,106 B2 | 9/2012 | Stone et al. |
| 8,292,921 B2 | 10/2012 | Stone et al. |
| 8,298,262 B2 | 10/2012 | Stone et al. |
| 8,303,604 B2 | 11/2012 | Stone et al. |
| 8,317,825 B2 | 11/2012 | Stone |
| 8,337,525 B2 | 12/2012 | Stone et al. |
| 8,361,113 B2 | 1/2013 | Stone et al. |
| 8,409,253 B2 | 4/2013 | Stone et al. |
| 2001/0010005 A1 | 7/2001 | Kammerer et al. |
| 2001/0014825 A1 | 8/2001 | Burke et al. |
| 2001/0019649 A1 | 9/2001 | Field et al. |
| 2001/0029387 A1 | 10/2001 | Wolf et al. |
| 2001/0037131 A1 | 11/2001 | Schmieding et al. |
| 2001/0037153 A1 | 11/2001 | Rockwood, Jr. et al. |
| 2001/0041916 A1 | 11/2001 | Bonutti |
| 2001/0041937 A1 | 11/2001 | Rieser et al. |
| 2001/0041938 A1 * | 11/2001 | Hein ........................ 623/13.13 |
| 2001/0044639 A1 | 11/2001 | Levinson |
| 2001/0047206 A1 | 11/2001 | Sklar et al. |
| 2001/0051816 A1 | 12/2001 | Enzerink et al. |
| 2001/0053934 A1 | 12/2001 | Schmieding |
| 2002/0001964 A1 | 1/2002 | Choi |
| 2002/0004669 A1 | 1/2002 | Bartlett |
| 2002/0007182 A1 | 1/2002 | Kim |
| 2002/0010513 A1 | 1/2002 | Schmieding |
| 2002/0013607 A1 | 1/2002 | Lemer |
| 2002/0013608 A1 | 1/2002 | ElAttrache et al. |
| 2002/0019649 A1 | 2/2002 | Sikora et al. |
| 2002/0029066 A1 | 3/2002 | Foerster |
| 2002/0032465 A1 | 3/2002 | Lemer |
| 2002/0055780 A1 | 5/2002 | Sklar |
| 2002/0058966 A1 | 5/2002 | Tormala et al. |
| 2002/0077659 A1 | 6/2002 | Johnson et al. |
| 2002/0099411 A1 | 7/2002 | Bartlett |
| 2002/0111653 A1 | 8/2002 | Foerster |
| 2002/0120270 A1 | 8/2002 | Trieu et al. |
| 2002/0120292 A1 | 8/2002 | Morgan |
| 2002/0123752 A1 | 9/2002 | Schultheiss et al. |
| 2002/0128654 A1 | 9/2002 | Steger et al. |
| 2002/0128684 A1 | 9/2002 | Foerster |
| 2002/0129820 A1 | 9/2002 | Ryan et al. |
| 2002/0143336 A1 | 10/2002 | Hearn |
| 2002/0147463 A1 | 10/2002 | Martinek |
| 2002/0161401 A1 | 10/2002 | Steiner |
| 2002/0161439 A1 | 10/2002 | Strobel et al. |
| 2002/0165548 A1 | 11/2002 | Jutley |
| 2002/0165611 A1 | 11/2002 | Enzerink et al. |
| 2002/0169452 A1 | 11/2002 | Tormala et al. |
| 2002/0169477 A1 | 11/2002 | Demopulos et al. |
| 2002/0169478 A1 | 11/2002 | Schwartz et al. |
| 2002/0173788 A1 | 11/2002 | Bojarski et al. |
| 2002/0188298 A1 | 12/2002 | Chan |
| 2002/0193830 A1 | 12/2002 | Bonutti |
| 2003/0004545 A1 | 1/2003 | Burkhart et al. |
| 2003/0023268 A1 | 1/2003 | Lizardi |
| 2003/0032961 A1 | 2/2003 | Pelo et al. |
| 2003/0033021 A1 | 2/2003 | Plouhar et al. |
| 2003/0033022 A1 | 2/2003 | Plouhar et al. |
| 2003/0036797 A1 | 2/2003 | Malaviya et al. |
| 2003/0036801 A1 | 2/2003 | Schwartz et al. |
| 2003/0065391 A1 | 4/2003 | Re et al. |
| 2003/0078585 A1 | 4/2003 | Johnson et al. |
| 2003/0078603 A1 | 4/2003 | Schaller et al. |
| 2003/0078617 A1 | 4/2003 | Schwartz et al. |
| 2003/0083662 A1 | 5/2003 | Middleton |
| 2003/0083694 A1 | 5/2003 | Miller |
| 2003/0088251 A1 | 5/2003 | Braun et al. |
| 2003/0088272 A1 | 5/2003 | Smith |
| 2003/0105477 A1 | 6/2003 | Schwartz et al. |
| 2003/0105489 A1 | 6/2003 | Eichhorn et al. |
| 2003/0120309 A1 | 6/2003 | Colleran et al. |
| 2003/0130694 A1 | 7/2003 | Bojarski et al. |
| 2003/0130695 A1 | 7/2003 | McDevitt et al. |
| 2003/0135214 A1 | 7/2003 | Fetto et al. |
| 2003/0135239 A1 | 7/2003 | Gabriel et al. |
| 2003/0135963 A1 | 7/2003 | Holbrook et al. |
| 2003/0152522 A1 | 8/2003 | Miller et al. |
| 2003/0153947 A1 | 8/2003 | Koseki |
| 2003/0167072 A1 | 9/2003 | Oberlander |
| 2003/0167090 A1 | 9/2003 | Chervitz et al. |
| 2003/0171811 A1 | 9/2003 | Steiner et al. |
| 2003/0176865 A1 | 9/2003 | Supinski |
| 2003/0176919 A1 | 9/2003 | Schmieding |
| 2003/0176920 A1 | 9/2003 | Sklar et al. |
| 2003/0181925 A1 | 9/2003 | Bain et al. |
| 2003/0195528 A1 | 10/2003 | Ritchart |
| 2003/0195564 A1 | 10/2003 | Tran et al. |
| 2003/0208210 A1 | 11/2003 | Dreyfuss et al. |
| 2003/0212456 A1 | 11/2003 | Lipchitz et al. |
| 2003/0220660 A1 | 11/2003 | Kortenbach et al. |
| 2003/0225459 A1 | 12/2003 | Hammer et al. |
| 2003/0229396 A1 | 12/2003 | Andrews |
| 2004/0002734 A1 | 1/2004 | Fallin et al. |
| 2004/0006345 A1 | 1/2004 | Vlahos et al. |
| 2004/0006346 A1 | 1/2004 | Holmen et al. |
| 2004/0015171 A1 | 1/2004 | Bojarski et al. |
| 2004/0015172 A1 | 1/2004 | Biedermann et al. |
| 2004/0024456 A1 | 2/2004 | Brown et al. |
| 2004/0024457 A1 | 2/2004 | Boyce et al. |
| 2004/0039389 A1 | 2/2004 | West et al. |
| 2004/0044391 A1 | 3/2004 | Porter |
| 2004/0059357 A1 | 3/2004 | Koseki |
| 2004/0087981 A1 | 5/2004 | Berube et al. |
| 2004/0092936 A1 | 5/2004 | Miller et al. |
| 2004/0093031 A1 | 5/2004 | Burkhart et al. |
| 2004/0093032 A1 | 5/2004 | Sinnott et al. |
| 2004/0098051 A1 | 5/2004 | Fallin et al. |
| 2004/0098053 A1 | 5/2004 | Tran |
| 2004/0111117 A1 | 6/2004 | Colleran et al. |
| 2004/0122431 A1 | 6/2004 | Biedermann et al. |
| 2004/0133206 A1 | 7/2004 | Stevens et al. |
| 2004/0133211 A1 | 7/2004 | Raskin et al. |
| 2004/0138664 A1 | 7/2004 | Bowman |
| 2004/0138683 A1 | 7/2004 | Shelton et al. |
| 2004/0138704 A1 | 7/2004 | Gambale et al. |
| 2004/0138706 A1 | 7/2004 | Abrams et al. |
| 2004/0138747 A1 | 7/2004 | Kaladelfos |
| 2004/0143344 A1 | 7/2004 | Malaviya et al. |
| 2004/0147932 A1 | 7/2004 | Burkinshaw et al. |
| 2004/0147958 A1 | 7/2004 | Lam et al. |
| 2004/0153103 A1 | 8/2004 | Schwartz et al. |
| 2004/0153153 A1 | 8/2004 | Elson et al. |
| 2004/0162579 A1 | 8/2004 | Foerster |
| 2004/0166169 A1 | 8/2004 | Malaviya et al. |
| 2004/0181234 A1 | 9/2004 | McDevitt et al. |
| 2004/0182968 A1 | 9/2004 | Gentry |
| 2004/0187314 A1 | 9/2004 | Johnson |
| 2004/0193185 A1 | 9/2004 | McBrayer |
| 2004/0199169 A1 | 10/2004 | Koons et al. |
| 2004/0204722 A1 * | 10/2004 | Sikora et al. ................. 606/151 |
| 2004/0220577 A1 | 11/2004 | Pelo et al. |
| 2004/0225292 A1 | 11/2004 | Sasso et al. |
| 2004/0225305 A1 | 11/2004 | Ewers et al. |
| 2004/0236353 A1 | 11/2004 | Bain et al. |
| 2004/0236373 A1 | 11/2004 | Anspach |
| 2004/0243139 A1 | 12/2004 | Lewis et al. |
| 2004/0243178 A1 | 12/2004 | Haut et al. |
| 2004/0243180 A1 | 12/2004 | Donnelly et al. |
| 2004/0243235 A1 | 12/2004 | Goh et al. |
| 2004/0249394 A1 | 12/2004 | Morris et al. |
| 2004/0260296 A1 | 12/2004 | Kaiser et al. |
| 2004/0260298 A1 | 12/2004 | Kaiser et al. |
| 2004/0267164 A1 | 12/2004 | Rhodes et al. |

(56) References Cited

U.S. PATENT DOCUMENTS

| | | |
|---|---|---|
| 2004/0267265 A1 | 12/2004 | Kyle |
| 2004/0267270 A1 | 12/2004 | Jacobs et al. |
| 2004/0267276 A1 | 12/2004 | Camino et al. |
| 2004/0267277 A1 | 12/2004 | Zannis et al. |
| 2004/0267286 A1 | 12/2004 | Gao et al. |
| 2004/0267304 A1 | 12/2004 | Zannis et al. |
| 2004/0267309 A1 | 12/2004 | Garvin |
| 2004/0267361 A1 | 12/2004 | Donnelly et al. |
| 2004/0267362 A1 | 12/2004 | Hwang et al. |
| 2005/0021087 A1 | 1/2005 | Koseki |
| 2005/0027307 A1 | 2/2005 | Schwartz et al. |
| 2005/0033363 A1* | 2/2005 | Bojarski et al. ............ 606/228 |
| 2005/0038426 A1 | 2/2005 | Chan |
| 2005/0055027 A1 | 3/2005 | Yeung et al. |
| 2005/0055037 A1 | 3/2005 | Fathauer |
| 2005/0064042 A1 | 3/2005 | Vunjak-Novakovic et al. |
| 2005/0065521 A1 | 3/2005 | Steger et al. |
| 2005/0065526 A1 | 3/2005 | Drew et al. |
| 2005/0070906 A1 | 3/2005 | Clark et al. |
| 2005/0070928 A1 | 3/2005 | Heino et al. |
| 2005/0074495 A1 | 4/2005 | Schwartz et al. |
| 2005/0085819 A1 | 4/2005 | Ellis et al. |
| 2005/0090828 A1 | 4/2005 | Alford |
| 2005/0090862 A1 | 4/2005 | McDevitt et al. |
| 2005/0096696 A1 | 5/2005 | Forsberg |
| 2005/0096697 A1 | 5/2005 | Forsberg et al. |
| 2005/0096743 A1 | 5/2005 | Schmieding et al. |
| 2005/0101957 A1 | 5/2005 | Buskirk et al. |
| 2005/0107795 A1 | 5/2005 | Morris et al. |
| 2005/0107828 A1 | 5/2005 | Reese |
| 2005/0119531 A1 | 6/2005 | Sharratt |
| 2005/0119696 A1 | 6/2005 | Walters et al. |
| 2005/0124996 A1 | 6/2005 | Hearn |
| 2005/0125031 A1* | 6/2005 | Pipenhagen et al. ........ 606/213 |
| 2005/0125036 A1 | 6/2005 | Roby |
| 2005/0125073 A1 | 6/2005 | Orban et al. |
| 2005/0131413 A1 | 6/2005 | O'Driscoll et al. |
| 2005/0137600 A1 | 6/2005 | Jacobs et al. |
| 2005/0137624 A1 | 6/2005 | Fallman |
| 2005/0149033 A1 | 7/2005 | McGuire et al. |
| 2005/0149122 A1 | 7/2005 | McDevitt et al. |
| 2005/0149187 A1 | 7/2005 | Clark et al. |
| 2005/0159812 A1 | 7/2005 | Dinger et al. |
| 2005/0165416 A1 | 7/2005 | Bojarski et al. |
| 2005/0165482 A1 | 7/2005 | Goldhahn et al. |
| 2005/0171603 A1 | 8/2005 | Justin et al. |
| 2005/0187565 A1 | 8/2005 | Baker et al. |
| 2005/0187577 A1 | 8/2005 | Selvitelli et al. |
| 2005/0187635 A1 | 8/2005 | Metzger |
| 2005/0203620 A1 | 9/2005 | Steiner et al. |
| 2005/0222618 A1 | 10/2005 | Dreyfuss et al. |
| 2005/0222619 A1 | 10/2005 | Dreyfuss et al. |
| 2005/0228448 A1 | 10/2005 | Li |
| 2005/0240198 A1 | 10/2005 | Albertson et al. |
| 2005/0251159 A1* | 11/2005 | Ewers et al. ................ 606/153 |
| 2005/0251177 A1 | 11/2005 | Saadat et al. |
| 2005/0251208 A1 | 11/2005 | Elmer et al. |
| 2005/0251210 A1 | 11/2005 | Westra et al. |
| 2005/0267479 A1 | 12/2005 | Morgan et al. |
| 2005/0267533 A1 | 12/2005 | Gertner |
| 2005/0277939 A1 | 12/2005 | Miller |
| 2005/0277961 A1 | 12/2005 | Stone et al. |
| 2005/0283040 A1 | 12/2005 | Greenhalgh |
| 2005/0283156 A1 | 12/2005 | Schmieding et al. |
| 2005/0283158 A1 | 12/2005 | West |
| 2005/0283192 A1 | 12/2005 | Torrie et al. |
| 2006/0004410 A1 | 1/2006 | Nobis et al. |
| 2006/0015103 A1 | 1/2006 | Burke |
| 2006/0015106 A1 | 1/2006 | Lerch et al. |
| 2006/0015107 A1 | 1/2006 | Sklar |
| 2006/0030884 A1 | 2/2006 | Yeung et al. |
| 2006/0030948 A1 | 2/2006 | Manrique et al. |
| 2006/0036265 A1 | 2/2006 | Dant |
| 2006/0052787 A1 | 3/2006 | Re et al. |
| 2006/0052818 A1 | 3/2006 | Drake et al. |
| 2006/0064125 A1 | 3/2006 | Henderson et al. |
| 2006/0064126 A1 | 3/2006 | Fallin et al. |
| 2006/0069334 A1 | 3/2006 | Moskowitz |
| 2006/0079904 A1 | 4/2006 | Thal |
| 2006/0084943 A1 | 4/2006 | Rosenman et al. |
| 2006/0085000 A1 | 4/2006 | Mohr et al. |
| 2006/0089672 A1 | 4/2006 | Martinek |
| 2006/0095130 A1 | 5/2006 | Caborn et al. |
| 2006/0095131 A1 | 5/2006 | Justin et al. |
| 2006/0100627 A1 | 5/2006 | Stone et al. |
| 2006/0100637 A1 | 5/2006 | Rathbun et al. |
| 2006/0106423 A1 | 5/2006 | Weisel et al. |
| 2006/0111721 A1 | 5/2006 | Puricelli et al. |
| 2006/0116685 A1 | 6/2006 | Urbanski et al. |
| 2006/0121084 A1 | 6/2006 | Borden et al. |
| 2006/0122608 A1 | 6/2006 | Fallin et al. |
| 2006/0122611 A1 | 6/2006 | Morales et al. |
| 2006/0135958 A1 | 6/2006 | Marissen et al. |
| 2006/0149258 A1 | 7/2006 | Sousa |
| 2006/0149266 A1 | 7/2006 | Cordasco |
| 2006/0155287 A1 | 7/2006 | Montgomery et al. |
| 2006/0161161 A1 | 7/2006 | Shifrin et al. |
| 2006/0167458 A1 | 7/2006 | Gabele |
| 2006/0167481 A1 | 7/2006 | Baker et al. |
| 2006/0167482 A1 | 7/2006 | Swain et al. |
| 2006/0173492 A1 | 8/2006 | Akerfeldt et al. |
| 2006/0178680 A1 | 8/2006 | Nelson et al. |
| 2006/0189993 A1 | 8/2006 | Stone |
| 2006/0190042 A1 | 8/2006 | Stone et al. |
| 2006/0195101 A1 | 8/2006 | Stevens |
| 2006/0200235 A1 | 9/2006 | Bianchi et al. |
| 2006/0212055 A1* | 9/2006 | Karabey et al. ............ 606/158 |
| 2006/0229671 A1 | 10/2006 | Steiner et al. |
| 2006/0235407 A1 | 10/2006 | Wang et al. |
| 2006/0235413 A1 | 10/2006 | Denham et al. |
| 2006/0241624 A1 | 10/2006 | Kizuka et al. |
| 2006/0247642 A1 | 11/2006 | Stone et al. |
| 2006/0253130 A1 | 11/2006 | Wolniewicz |
| 2006/0259048 A1 | 11/2006 | Koseki |
| 2006/0271192 A1 | 11/2006 | Olsen et al. |
| 2006/0276793 A1 | 12/2006 | Berry |
| 2006/0276809 A1 | 12/2006 | Oliveira |
| 2006/0276841 A1 | 12/2006 | Barbieri et al. |
| 2006/0280768 A1 | 12/2006 | Hwang et al. |
| 2006/0282082 A1 | 12/2006 | Fanton et al. |
| 2006/0282083 A1 | 12/2006 | Fanton et al. |
| 2006/0282085 A1 | 12/2006 | Stone et al. |
| 2006/0293709 A1 | 12/2006 | Bojarski et al. |
| 2007/0005080 A1 | 1/2007 | Wolniewicz et al. |
| 2007/0010857 A1* | 1/2007 | Sugimoto et al. ............ 606/232 |
| 2007/0016305 A1 | 1/2007 | Chudik |
| 2007/0021779 A1 | 1/2007 | Garvin et al. |
| 2007/0032800 A1* | 2/2007 | Ortiz et al. .................. 606/148 |
| 2007/0038218 A1 | 2/2007 | Grevious |
| 2007/0043371 A1 | 2/2007 | Teague et al. |
| 2007/0055249 A1 | 3/2007 | Jensen et al. |
| 2007/0055251 A1 | 3/2007 | Huebner et al. |
| 2007/0055255 A1 | 3/2007 | Siegel |
| 2007/0060922 A1 | 3/2007 | Dreyfuss |
| 2007/0067025 A1 | 3/2007 | Schwartz |
| 2007/0073307 A1 | 3/2007 | Scribner et al. |
| 2007/0078435 A1 | 4/2007 | Stone et al. |
| 2007/0083236 A1 | 4/2007 | Sikora et al. |
| 2007/0093847 A1 | 4/2007 | Scribner et al. |
| 2007/0100350 A1 | 5/2007 | Deffenbaugh et al. |
| 2007/0118217 A1 | 5/2007 | Brulez et al. |
| 2007/0123883 A1 | 5/2007 | Ellis et al. |
| 2007/0142838 A1 | 6/2007 | Jordan |
| 2007/0156174 A1 | 7/2007 | Kaiser et al. |
| 2007/0162018 A1 | 7/2007 | Jensen et al. |
| 2007/0185488 A1 | 8/2007 | Pohjonen et al. |
| 2007/0185532 A1 | 8/2007 | Stone et al. |
| 2007/0185568 A1 | 8/2007 | Schwartz |
| 2007/0191849 A1 | 8/2007 | ElAttrache et al. |
| 2007/0191853 A1 | 8/2007 | Stone |
| 2007/0198036 A1 | 8/2007 | Sklar et al. |
| 2007/0219558 A1 | 9/2007 | Deutsch |
| 2007/0225719 A1 | 9/2007 | Stone et al. |
| 2007/0225805 A1 | 9/2007 | Schmieding |

(56) References Cited

U.S. PATENT DOCUMENTS

| | | |
|---|---|---|
| 2007/0233241 A1 | 10/2007 | Graf et al. |
| 2007/0239209 A1 | 10/2007 | Fallman |
| 2007/0239275 A1 | 10/2007 | Willobee |
| 2007/0250163 A1 | 10/2007 | Cassani |
| 2007/0260251 A1 | 11/2007 | Weier et al. |
| 2007/0260279 A1 | 11/2007 | Hotter et al. |
| 2007/0270856 A1 | 11/2007 | Morales et al. |
| 2007/0276387 A1 | 11/2007 | Morales et al. |
| 2008/0027430 A1 | 1/2008 | Montgomery et al. |
| 2008/0027446 A1 | 1/2008 | Stone et al. |
| 2008/0033549 A1 | 2/2008 | Marshall et al. |
| 2008/0046009 A1 | 2/2008 | Albertorio et al. |
| 2008/0051836 A1 | 2/2008 | Foerster et al. |
| 2008/0065114 A1 | 3/2008 | Stone et al. |
| 2008/0071299 A1 | 3/2008 | Allinniemi et al. |
| 2008/0082101 A1 | 4/2008 | Reisberg |
| 2008/0082127 A1* | 4/2008 | Stone et al. .................... 606/232 |
| 2008/0082128 A1* | 4/2008 | Stone ............................. 606/232 |
| 2008/0097430 A1 | 4/2008 | Bernstein et al. |
| 2008/0119892 A1 | 5/2008 | Brailovski et al. |
| 2008/0132753 A1 | 6/2008 | Goddard |
| 2008/0132932 A1 | 6/2008 | Hoeppner et al. |
| 2008/0132948 A1 | 6/2008 | Surti et al. |
| 2008/0133007 A1 | 6/2008 | Donnelly et al. |
| 2008/0140092 A1 | 6/2008 | Stone et al. |
| 2008/0140093 A1 | 6/2008 | Stone et al. |
| 2008/0140128 A1 | 6/2008 | Smisson et al. |
| 2008/0154260 A1 | 6/2008 | Hoof |
| 2008/0154314 A1 | 6/2008 | McDevitt |
| 2008/0161806 A1 | 7/2008 | Donnelly et al. |
| 2008/0161852 A1 | 7/2008 | Kaiser et al. |
| 2008/0161861 A1 | 7/2008 | Huebner |
| 2008/0161864 A1 | 7/2008 | Beck et al. |
| 2008/0172097 A1 | 7/2008 | Lerch et al. |
| 2008/0183290 A1 | 7/2008 | Baird et al. |
| 2008/0188933 A1 | 8/2008 | Koob et al. |
| 2008/0188936 A1 | 8/2008 | Ball et al. |
| 2008/0221527 A1 | 9/2008 | Bradley et al. |
| 2008/0221578 A1 | 9/2008 | Zeitani |
| 2008/0228186 A1 | 9/2008 | Gall et al. |
| 2008/0234730 A1 | 9/2008 | Cotton et al. |
| 2008/0255613 A1 | 10/2008 | Kaiser et al. |
| 2008/0262544 A1 | 10/2008 | Burkhart |
| 2008/0268064 A1 | 10/2008 | Woodell-May |
| 2008/0269674 A1 | 10/2008 | Stone |
| 2008/0275477 A1 | 11/2008 | Sterrett et al. |
| 2008/0300611 A1 | 12/2008 | Houser et al. |
| 2008/0312689 A1 | 12/2008 | Denham et al. |
| 2009/0018589 A1 | 1/2009 | Smisson, III et al. |
| 2009/0018655 A1* | 1/2009 | Brunelle et al. ............ 623/13.19 |
| 2009/0043342 A1 | 2/2009 | Freedland |
| 2009/0054928 A1 | 2/2009 | Denham et al. |
| 2009/0062854 A1 | 3/2009 | Kaiser et al. |
| 2009/0082790 A1 | 3/2009 | Shad et al. |
| 2009/0082805 A1 | 3/2009 | Kaiser et al. |
| 2009/0099598 A1 | 4/2009 | McDevitt et al. |
| 2009/0105754 A1 | 4/2009 | Sethi |
| 2009/0118774 A1 | 5/2009 | Miller, III |
| 2009/0118775 A1 | 5/2009 | Burke |
| 2009/0125073 A1 | 5/2009 | Rehm |
| 2009/0138002 A1 | 5/2009 | Fenton |
| 2009/0138054 A1 | 5/2009 | Teague et al. |
| 2009/0156997 A1 | 6/2009 | Trenhaile |
| 2009/0163949 A1 | 6/2009 | Rolnick et al. |
| 2009/0177233 A1 | 7/2009 | Malek |
| 2009/0192468 A1 | 7/2009 | Stone |
| 2009/0198277 A1 | 8/2009 | Gordon et al. |
| 2009/0204146 A1 | 8/2009 | Kaiser et al. |
| 2009/0228042 A1 | 9/2009 | Koogle, Jr. et al. |
| 2009/0234357 A1 | 9/2009 | Morales et al. |
| 2009/0234358 A1 | 9/2009 | Morales et al. |
| 2009/0240251 A1 | 9/2009 | Gabele |
| 2009/0240335 A1* | 9/2009 | Arcenio et al. ............ 623/17.16 |
| 2009/0248091 A1 | 10/2009 | Teague et al. |
| 2009/0265014 A1 | 10/2009 | May et al. |
| 2009/0299409 A1 | 12/2009 | Coe et al. |
| 2009/0306711 A1 | 12/2009 | Stone et al. |
| 2009/0312776 A1 | 12/2009 | Kaiser et al. |
| 2009/0318960 A1 | 12/2009 | Burkhart |
| 2009/0318961 A1 | 12/2009 | Stone et al. |
| 2010/0042114 A1 | 2/2010 | Schaffhausen |
| 2010/0087857 A1 | 4/2010 | Stone et al. |
| 2010/0145384 A1 | 6/2010 | Stone et al. |
| 2010/0191342 A1 | 7/2010 | Byrd et al. |
| 2010/0211075 A1 | 8/2010 | Stone |
| 2010/0256677 A1 | 10/2010 | Albertorio et al. |
| 2010/0268273 A1 | 10/2010 | Albertorio et al. |
| 2010/0268275 A1 | 10/2010 | Stone et al. |
| 2010/0270306 A1 | 10/2010 | Shiffer |
| 2010/0292792 A1 | 11/2010 | Stone et al. |
| 2010/0305698 A1 | 12/2010 | Metzger et al. |
| 2010/0305709 A1 | 12/2010 | Metzger et al. |
| 2010/0312341 A1 | 12/2010 | Kaiser et al. |
| 2011/0009885 A1 | 1/2011 | Graf et al. |
| 2011/0046733 A1 | 2/2011 | Eggli |
| 2011/0087284 A1 | 4/2011 | Stone et al. |
| 2011/0098727 A1 | 4/2011 | Kaiser et al. |
| 2011/0106153 A1 | 5/2011 | Stone et al. |
| 2011/0160767 A1 | 6/2011 | Stone et al. |
| 2011/0160768 A1 | 6/2011 | Stone et al. |
| 2011/0208239 A1 | 8/2011 | Stone et al. |
| 2011/0208240 A1 | 8/2011 | Stone et al. |
| 2011/0213416 A1 | 9/2011 | Kaiser |
| 2011/0218625 A1 | 9/2011 | Berelsman et al. |
| 2011/0224799 A1 | 9/2011 | Stone |
| 2011/0264141 A1 | 10/2011 | Denham et al. |
| 2011/0270278 A1 | 11/2011 | Overes et al. |
| 2011/0270306 A1 | 11/2011 | Denham et al. |
| 2012/0041485 A1 | 2/2012 | Kaiser et al. |
| 2012/0041486 A1 | 2/2012 | Stone et al. |
| 2012/0046693 A1 | 2/2012 | Denham et al. |
| 2012/0053630 A1 | 3/2012 | Denham et al. |
| 2012/0059417 A1 | 3/2012 | Norton et al. |
| 2012/0059418 A1 | 3/2012 | Denham et al. |
| 2012/0089193 A1 | 4/2012 | Stone et al. |
| 2012/0095470 A1 | 4/2012 | Kaiser et al. |
| 2012/0123447 A1 | 5/2012 | Corrao et al. |
| 2012/0123474 A1 | 5/2012 | Zajac et al. |
| 2012/0123541 A1 | 5/2012 | Albertorio et al. |
| 2012/0150297 A1 | 6/2012 | Denham et al. |
| 2012/0165866 A1 | 6/2012 | Kaiser et al. |
| 2012/0165867 A1 | 6/2012 | Denham et al. |
| 2012/0165938 A1 | 6/2012 | Denham et al. |
| 2012/0197271 A1 | 8/2012 | Astorino et al. |
| 2012/0245585 A1 | 9/2012 | Kaiser et al. |
| 2012/0296427 A1 | 11/2012 | Conner et al. |
| 2012/0310245 A1 | 12/2012 | Hoeppner et al. |
| 2013/0023930 A1 | 1/2013 | Stone et al. |
| 2013/0035698 A1 | 2/2013 | Stone et al. |
| 2013/0046341 A1 | 2/2013 | Stone et al. |
| 2013/0103082 A1 | 4/2013 | Kaiser et al. |
| 2013/0110251 A1 | 5/2013 | Metzger et al. |
| 2013/0116730 A1 | 5/2013 | Denham et al. |
| 2013/0123813 A1 | 5/2013 | Stone et al. |

FOREIGN PATENT DOCUMENTS

| | | |
|---|---|---|
| AU | 5850469 | 1/1971 |
| AU | 5963869 | 2/1971 |
| AU | 1505470 | 11/1971 |
| AU | 2223767 | 5/1973 |
| AU | 3615171 | 5/1973 |
| AU | 5028569 | 9/1973 |
| AU | 7110887 | 10/1987 |
| AU | 639410 | 11/1989 |
| AU | 651929 | 8/1994 |
| DE | 2529669 | 3/1976 |
| DE | 2747312 | 4/1979 |
| DE | 2818254 | 10/1979 |
| DE | 2919009 | 11/1979 |
| DE | 3027138 | 12/1981 |
| DE | 3225620 | 2/1983 |
| DE | 3136083 | 3/1983 |
| DE | 233303 | 2/1986 |

(56) References Cited

FOREIGN PATENT DOCUMENTS

| | | |
|---|---|---|
| DE | 4127550 | 2/1993 |
| DE | 4302397 | 7/1993 |
| DE | 29621340 | 5/1998 |
| DE | 19841252 | 3/2000 |
| DE | 20207781 U1 | 8/2002 |
| EP | 0108912 | 5/1984 |
| EP | 0129442 | 12/1984 |
| EP | 0172130 | 2/1986 |
| EP | 0241240 | 10/1987 |
| EP | 0241792 | 10/1987 |
| EP | 0260970 | 3/1988 |
| EP | 0270704 | 6/1988 |
| EP | 0282789 | 9/1988 |
| EP | 0315371 | 5/1989 |
| EP | 0317406 | 5/1989 |
| EP | 0340159 | 11/1989 |
| EP | 0346183 | 12/1989 |
| EP | 0349173 | 1/1990 |
| EP | 0374088 | 6/1990 |
| EP | 0409364 | 1/1991 |
| EP | 0415915 | 3/1991 |
| EP | 0440991 | 8/1991 |
| EP | 0441065 | 8/1991 |
| EP | 0451932 | 10/1991 |
| EP | 0464480 | 1/1992 |
| EP | 0497079 | 8/1992 |
| EP | 0502509 | 9/1992 |
| EP | 0502698 | 9/1992 |
| EP | 520177 | 12/1992 |
| EP | 0546726 | 6/1993 |
| EP | 0574707 | 12/1993 |
| EP | 0582514 | 2/1994 |
| EP | 0591991 | 4/1994 |
| EP | 0598219 | 5/1994 |
| EP | 0611551 A1 | 8/1994 |
| EP | 0627203 | 12/1994 |
| EP | 0651979 | 5/1995 |
| EP | 0669110 | 8/1995 |
| EP | 0686373 | 12/1995 |
| EP | 0702933 | 3/1996 |
| EP | 0775473 | 5/1997 |
| EP | 0913123 | 5/1999 |
| EP | 0913131 | 5/1999 |
| EP | 99121106 | 10/1999 |
| EP | 991210527 | 10/1999 |
| EP | 0995409 | 4/2000 |
| EP | 1013229 | 6/2000 |
| EP | 1093773 | 4/2001 |
| EP | 1093774 | 4/2001 |
| EP | 1555945 | 7/2005 |
| EP | 2238944 A2 | 10/2010 |
| EP | 2544607 A1 | 1/2013 |
| FR | 2622790 | 5/1989 |
| FR | 2655840 | 6/1991 |
| FR | 2682867 | 4/1993 |
| FR | 2687911 | 9/1993 |
| FR | 2688689 | 9/1993 |
| FR | 2704140 | 10/1994 |
| FR | 2717070 | 9/1995 |
| FR | 2723528 | 2/1996 |
| FR | 2744010 | 8/1997 |
| FR | 2745999 | 9/1997 |
| FR | 2770764 | 5/1999 |
| GB | 401677 | 11/1933 |
| GB | 1413477 | 11/1975 |
| GB | 1485681 | 9/1977 |
| GB | 2083751 | 3/1982 |
| GB | 2118474 | 11/1983 |
| GB | 2227175 | 7/1990 |
| GB | 2253147 A | 9/1992 |
| GB | 2312376 | 10/1997 |
| GB | 2403416 A | 1/2005 |
| JP | 5362911 | 5/1978 |
| JP | 5362912 | 5/1978 |
| JP | 5374942 | 6/1978 |
| JP | 5378230 | 6/1978 |
| JP | 62159647 | 7/1987 |
| JP | 62295657 | 12/1987 |
| JP | 5269160 | 10/1993 |
| JP | 5300917 | 11/1993 |
| JP | 751292 | 2/1995 |
| JP | 10211213 | 8/1998 |
| WO | WO-8300615 | 3/1983 |
| WO | WO-8603666 | 7/1986 |
| WO | WO-8701270 | 3/1987 |
| WO | WO-8901767 | 3/1989 |
| WO | WO-8909030 | 10/1989 |
| WO | WO-8910096 | 11/1989 |
| WO | WO-9008510 | 8/1990 |
| WO | WO-9203980 | 3/1992 |
| WO | WO-9314705 | 8/1993 |
| WO | WO-9315694 | 8/1993 |
| WO | WO-9502373 | 1/1995 |
| WO | WO-9503003 | 2/1995 |
| WO | WO-9529637 | 11/1995 |
| WO | WO-9532670 | 12/1995 |
| WO | WO-9609797 A1 | 4/1996 |
| WO | WO-9629029 | 9/1996 |
| WO | WO-9737603 | 10/1997 |
| WO | WO-9812991 | 4/1998 |
| WO | WO-9812992 | 4/1998 |
| WO | WO-9822047 | 5/1998 |
| WO | WO-9822048 | 5/1998 |
| WO | WO-9901084 | 1/1999 |
| WO | WO-9912480 | 3/1999 |
| WO | WO-9937219 A1 | 7/1999 |
| WO | WO-9944544 | 9/1999 |
| WO | WO-9952472 A1 | 10/1999 |
| WO | WO-0040159 | 7/2000 |
| WO | WO-0139671 | 6/2001 |
| WO | WO-0236020 | 5/2002 |
| WO | WO-03005914 A1 | 1/2003 |
| WO | WO-03071962 | 9/2003 |
| WO | WO-03077772 | 9/2003 |
| WO | WO-03092551 A1 | 11/2003 |
| WO | WO-2004091412 A1 | 10/2004 |
| WO | WO-2005104992 A1 | 11/2005 |
| WO | WO-2006023661 A2 | 3/2006 |
| WO | WO-2006055823 A2 | 5/2006 |
| WO | WO-2007045460 A2 | 4/2007 |
| WO | WO-2007109280 A2 | 9/2007 |
| WO | WO-2008002550 A2 | 1/2008 |
| WO | WO-2008015171 A1 | 2/2008 |
| WO | WO-2008073588 A2 | 6/2008 |
| WO | WO-2009012021 A1 | 1/2009 |
| WO | WO-2011112371 A1 | 9/2011 |
| WO | WO-2011150238 A1 | 12/2011 |
| WO | WO-2012134999 A1 | 10/2012 |
| WO | WO-2012158583 A1 | 11/2012 |

OTHER PUBLICATIONS

Pioneer® Sternal Cable System (2010).
Rapid Sternal Closure (2006) KLS Martin L.P. http://www.rapidsternalclosure.com/medical/demo.php Web accessed Sep. 8, 2008.
Saxena, Pankaj, MCh, DNB et al., "Use of Double Wires in Sternal Closure, A Useful Technique," Texas Heart® Institute. Journal List>Tex Heart Inst J > v.33(4); (2006).
Zeitani, Jacob, M.D., "A New Sternal Reinforcement Device to Prevent and Treat Sternal Dehiscence," CTSNet.org (Jun. 30, 2008).
"AperFix® System Surgical Technique Guide. Single Tunnel Double Bundle.™" Cayenne Medical brochure. (Aug. 2008) 8 sheets.
"Bio-Intrafix (TCP/PLA & Intrafix, Tibial Soft Tissue Fasteners," by DePuy Mitek, 6 sheets, (date unknown).
"Bio-Intrafix Tibial Soft Tissue Fasteners, Building on the Legacy of IntraFix," brochure. DePuy Mitek, (Feb. 2007) 6 sheets.
"Biomechanical Evaluation of the Biomet Sports Medicine JurggerKnot™ Soft Anchor in Porcine Bone," Study completed Jan. 2010. Biomet Sports Medicine Research and Development, Warsaw, Indiana. 2 pages.
"Do your next distal tendon repair with . . . The Lubbers Technique", Teno Fix® brochure, 2003 (2 pages) Ortheon® Medical.

(56) References Cited

OTHER PUBLICATIONS

"EZ Loc Femoral Fixation Device," copyright 2005 Arthrotek, Inc. (8 sheets).
"JuggerKnot™ Soft Anchor Midfoot Repair," brochure. Biomet Sports Medicine (Jul. 2011) 12 sheets.
"JuggerKnot™ Soft Anchor. It's Small. It's strong. And it's all suture . . . " Ordering Information brochure. Biomet Sports Medicine (Jun. 2011) 2 sheets.
"JuggerKnot™ Soft Anchor. Labral Repair," brochure. Biomet Sports Medicine (Apr. 2011) 12 sheets.
"Make your next tendon repair an open-and-shut case. The Teno Fix® Tendon Repair System", Teno Fix® brochure, 2003 (2 pages) Ortheon® Medical.
"PANALOK Anchor with PDS II and ETHIBOND Suture", Mitek Products ETHICON, 1997.
"SE Graft Tensioning System Surgical Technique," Linvatec Corporation copyright 2003, 2004.
"Technique for ACL Reconstruction with Acufex Director Drill Guide and Endobutton CL," by Thomas D. Roseberg, copyright 1999 Smith & Nephew.
A. Weiler, et al; Biodegradierbare Interferenzschrauben in der Kreuzbandchirurgie; OP-Journal 14 pp. 278-284; 1998.
Arthrotek, A Biomet Company; Knees; Sure fire Hybrid Meniscal Device. (2005).
Arthrotek, A Biomet Company; Sure fire Hybrid Meniscal Device; Launch Date: Fall AANA 2004.
F. Alan Barber, M.D., "Uses and Abuses of Sutures and Anchors," Shoulder Scope, San Diego Shoulder Arthroscopy Library.
F. Alan Barber, M.D., "Using Sutures and Anchors," San Diego Shoulder Arthroscopy Course, 17th Annual Meeting.
Flavia Namie Azato, et al. "Traction endurance biomechanical study of metallic suture anchors at different insertion angles," Acta ortop. bras., vol. 11, No. 1, Sao Paulo, Jan./Mar. 2003.
Hecker AT, et al., "Pull-out strength of suture anchors for rotator cuff and Bankart lesion repairs," Am J Sports Med. 1993.
International Search Report and Written Opinion mailed Jul. 28, 2011 for PCT/US2011/026349 claiming benefit of U.S. Appl. No. 12/938,902, filed Nov. 3, 2010; and U.S. Appl. No. 12/719,337, filed Mar. 8, 2010.
International Search Report and Written Opinion mailed Oct. 14, 2011 for PCT/US2011/038188 filed May 26, 2011 claiming benefit of U.S. Appl. No. 12/788,973, filed May 27, 2010 and U.S. Appl. No. 12/788,966, filed May 27, 2010.
Invitation to Pay Additional Fees mailed Aug. 5, 2011 for PCT/US2011/038188 claiming benefit of U.S. Appl. No. 12/788,973, filed May 27, 2010 and U.S. Appl. No. 12/788,966, filed May 27, 2010.
Invitation to Pay Additional Fees mailed Jun. 9, 2011 for PCT/US2011/026349 claiming benefit of U.S. Appl. No. 12/938,902, filed Nov. 3, 2010; and U.S. Appl. No. 12/719,337, filed Mar. 8, 2010.
Lawhorn, M.D., Keith, MaxFire™ Meniscal Repair Device with Zip Loop™ Technology, Biomet Sports Medicine, Feb. 29, 2008.
Mark D. Miller et al.; "Pitfalls Associated with FasT-Fix Meniscal Repair," Arthroscopy: The Journal of Arthroscopic and Related Surgery, vol. 18, No. 8 Oct. 2002: pp. 939-943.
Opus Medical; The AutoCuff System; www.opusmedical.com; 2003.
Patrick Hunt, et al.; Development of a Perforated Biodegradable Interference Screw; Arthroscopy: The Journal of Arthroscopic and Related Surgery, vol. 21, No. 3; pp. 258-265; Mar. 2005.
Roy Alan Majors, M.D.; "Meniscal repairs: proven techniques and current trends," Lippincott Williams & Wilkins, Inc.; 2002.
Shoulder Arthroscopy; pp. H-2-H-22.
Smith & Nephew Endoscopy, "Endoscopic Meniscal Repair Using the T-Fix;" 1996.
Smith & Nephew, "Fast-Fix," Meniscal Repair System; 2001.
Stuart E. Fromm, M.D., RapidLoc, Meniscal Repair System, Mitek Products, Ethicon, 2001.
ToggleLoc™ Femoral Fixation Device, Arthrotek, Mar. 31, 2006.
Invitation to Pay Additional Fees mailed Jul. 19, 2012, for PCT/US2012/037703 claiming benefit of U.S. Appl. No. 13/109,667, filed May 7, 2011.
"Suture Tensioner w/Tensiometer," Arthrex® , Inc. catalog "Next Generation in Knee Ligament Reconstruction & Repair Technology," 2009.
"TriTis™ Tibial Fixation System and Implant" brochure. Scandius Biomedical (2006).
International Search Report and Written Opinion mailed Sep. 21, 2012 for PCT/US2012/037703 filed May 14, 2012 claiming benefit of U.S. Appl. No. 13/109,667, filed May 17, 2011 and U.S. Appl. No. 13/109,672, filed May 17, 2011.
International Preliminary Report on Patentability mailed Sep. 20, 2012 for PCT/US2011/026349 which claims benefit of U.S. Appl. No. 12/719,337, filed Mar. 8, 2010.
International Preliminary Report on Patentability mailed Dec. 6, 2012 for PCT/US2011/038188 claiming benefit of U.S. Appl. No. 12/788,966, filed May 27, 2010.
International Preliminary Report on Patentability and Written Opinion mailed Nov. 28, 2013 for PCT/US2012/037703, which claims benefit of U.S. Appl. No. 13/109,672, filed May 17, 2011, and U.S. Appl. No. 13/109,667, filed May 17, 2011.
US 6,238,418, 05/2001, Schwartz et al. (withdrawn)

\* cited by examiner

FLEXIBLE ANCHORS FOR TISSUE FIXATION

CROSS-REFERENCE TO RELATED APPLICATIONS

This application is a continuation-in-part of U.S. patent application Ser. No. 13/111,564 filed on May 19, 2011.

This application is a continuation-in-part of U.S. patent application Ser. No. 13/098,927 filed on May 2, 2011, which is a continuation in part of U.S. patent application Ser. No. 12/196,398 filed Aug. 22, 2008 and now U.S. Pat. No. 7,959,650.

This application is a continuation-in-part of U.S. patent application Ser. No. 13/098,897 filed on May 2, 2011.

This application is a continuation-in-part of U.S. patent application Ser. No. 12/976,328 filed on Dec. 22, 2010, which is a continuation of U.S. patent application Ser. No. 11/869,440 filed on Oct. 9, 2007 and now U.S. Pat. No. 7,857,830, which is a continuation-in-part of U.S. patent application Ser. No. 11/347,661 filed on Feb. 3, 2006 and now U.S. Pat. No. 7,749,250.

This application is a continuation-in-part of U.S. patent application Ser. No. 12/938,902 filed on Nov. 3, 2010.

This application is a continuation-in-part of U.S. patent application Ser. No. 12/915,962 filed on Oct. 29, 2010.

This application is a continuation-in-part of U.S. patent application Ser. No. 12/570,854 filed on Sep. 30, 2009, which is a continuation-in-part of U.S. patent application Ser. No. 12/014,399 filed on Jan. 15, 2008 and now U.S. Pat. No. 7,909,851.

This application is a continuation-in-part of U.S. patent application Ser. No. 12/489,168 filed on Jun. 22, 2009, which is a continuation-in-part of U.S. patent application Ser. No. 12/474,802 filed on May 29, 2009, which is a continuation-in-part of U.S. patent application Ser. No. 12/196,410 filed on Aug. 22, 2008.

This application is a continuation-in-part of U.S. patent application Ser. No. 12/489,181 filed on Jun. 22, 2009, which is a continuation-in-part of (a) U.S. patent application Ser. No. 12/014,399 filed on Jan. 15, 2008 and now U.S. Pat. No. 7,909,851; (b) U.S. patent application Ser. No. 12/014,340 filed on Jan. 15, 2008 and now U.S. Pat. No. 7,905,904; and (c) U.S. patent application Ser. No. 11/935,681 filed on Nov. 6, 2007 and now U.S. Pat. No. 7,905,903.

This application is a continuation-in-part of U.S. patent application Ser. No. 11/504,882 filed on Aug. 16, 2006, which is a continuation-in-part of U.S. patent application Ser. No. 11/408,282 filed on Apr. 20, 2006, which is now abandoned.

The entire disclosures of each of the above applications are incorporated herein by reference.

FIELD

The present disclosure relates to surgical methods and apparatuses, and generally for attaching tissue to bone.

BACKGROUND

This section provides background information related to the present disclosure which is not necessarily prior art.

Tears caused by trauma or disease in soft tissue, such as cartilage, ligament, or muscle, can be repaired by suturing. Various repair techniques and devices have been developed for facilitating suturing that include the use of rigid, non-flexible anchors and that are effective for their intended purposes. Nevertheless, there is still a need in the relevant art for tissue repair techniques and associated devices for facilitating suturing without requiring the use of rigid anchors.

SUMMARY

This section provides a general summary of the disclosure, and is not a comprehensive disclosure of its full scope or all of its features.

In one form, the present disclosure provides an anchor for securing tissue to bone that can include a flexible first tubular member, a flexible second tubular member, and a first suture member. The first tubular member can include a first wall defining a first passage between first and second ends. The second tubular member can include a second wall defining a second passage between first and second ends. The first suture member can couple the first tubular member and the second tubular member. The first suture member can pass through the first wall and the first passage and the second wall and the second passage. The first tubular member and the second tubular member can engage each other and deform to form an anchoring mass upon tensioning the first suture member.

In various aspects, the present disclosure also provides an anchor for securing tissue to bone that can include a flexible first tubular member and a first suture member. The first tubular member can include a wall defining a passage extending along an axis between first and second ends. The first suture member can pass through the wall and the passage a plurality of times to create a plurality of intersecting sections and at least one loop section coupling the plurality of intersecting sections. The intersecting sections can extend between a first aperture in the wall through which the first suture member enters the passage and a second aperture in the wall through which the first suture member exits the passage. At least two of the plurality of intersecting sections can move towards each other and deform a section extending between them upon tensioning the first suture member.

In other aspects, the present disclosure also provides an anchor for securing tissue to bone that can include a flexible first elongate member having first and second ends, a flexible second elongate member having first and second ends, and a suture member. The suture member can couple the first elongate member and the second elongate member. The suture member can pass through both the first elongate member and the second elongate member a plurality of times. The first elongate member and the second elongate member can engage each other and can deform to form an anchoring mass upon tensioning the suture member.

In another form, the present disclosure provides a method of preparing an anchor for securing soft tissue to bone. The method can include: (i) providing a flexible first tubular member including a first wall defining a first passage between first and second ends, (ii) providing a flexible second tubular member including a second wall defining a second passage between first and second ends, and (iii) passing a suture member through the first wall and the first passage and the second wall and the second passage to couple the first tubular member and the second tubular member.

In various aspects, the present disclosure also provides a method of securing a tissue to a bone that can include determining an area of the bone to couple an anchor. The anchor can include: (i) a flexible first tubular member including a first wall defining a first passage between first and second ends, (ii) a flexible second tubular member including a second wall defining a second passage between first and second ends, and (iii) a first suture member passing through the first wall and the first passage and the second wall and the second passage. The method can further include positioning the anchor at a position relative to the area, and tensioning the first suture member until the first tubular member engages the second tubular member, and the first flexible tubular member and the second tubular member deform to form an anchoring mass.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

DETAILED DESCRIPTION

Figure 1:
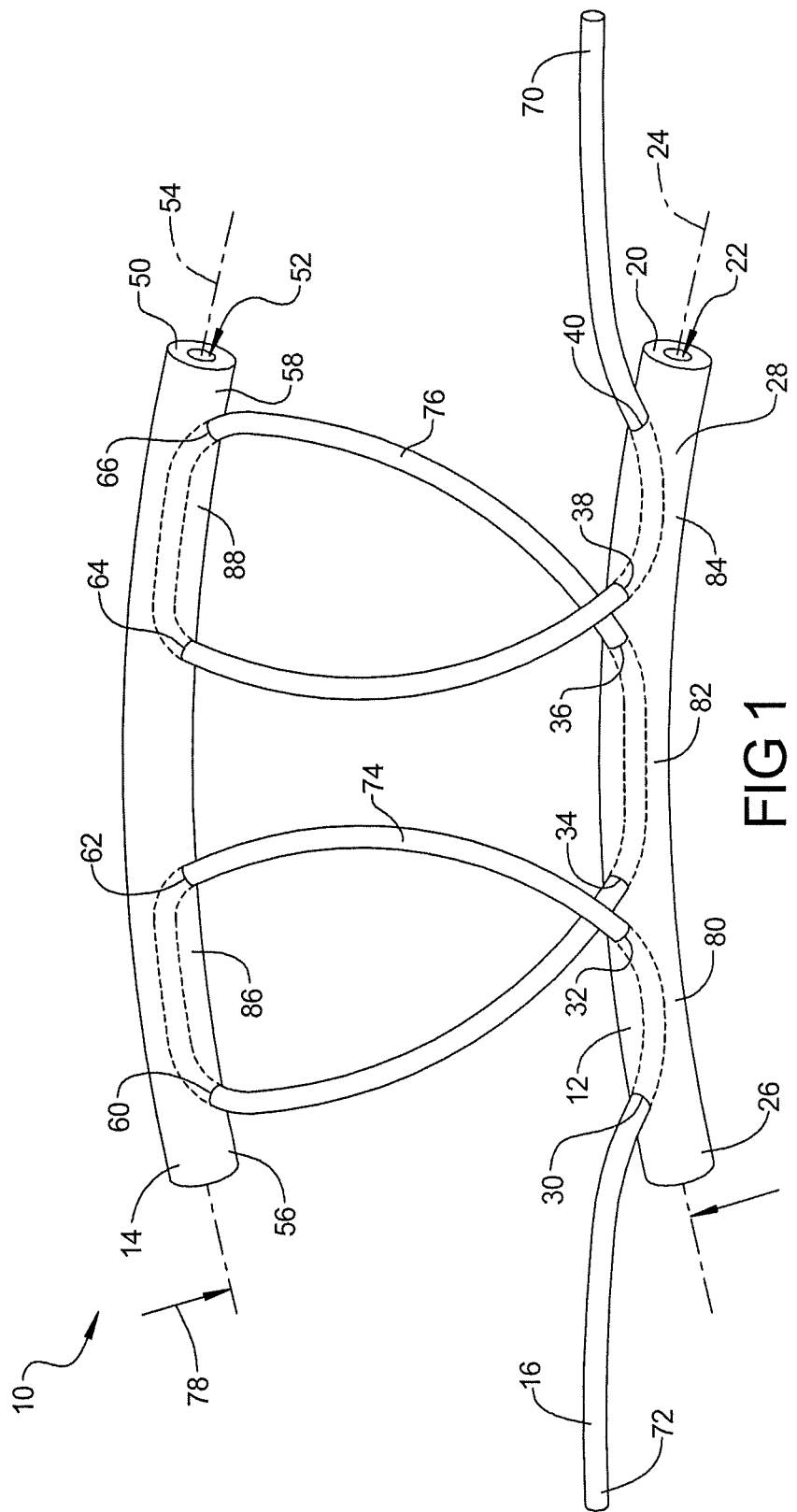
FIG. 1 is a perspective view illustrating an exemplary anchor for securing tissue to bone according to the present disclosure.

The following description is merely exemplary in nature and is not intended to limit the present disclosure, its application, or uses. It should be understood that throughout the drawings, corresponding reference numerals indicate corresponding parts throughout the several views of the drawings.

The present disclosure provides various anchors for securing a tissue to a bone, as well as methods of assembling the anchors, and methods of securing a tissue to a bone using the anchors. It will be appreciated that the anchors and methods can be used for various therapeutic purposes including, but not limited to, suturing repairs of tears caused by trauma or disease in soft tissue, such as cartilage, ligament, or muscle. For example, the anchors and methods can be used to attach soft tissue to bone. It will be further appreciated that the anchors and methods are not limited to attaching soft tissue to bone and can also be used to attach bone to bone. Moreover, while the anchors are illustrated as being positioned within a bone in various examples, the anchors can be embedded within or engage an outer surface of the bone or an adjoining tissue as illustrated in other examples.

With particular reference to FIG. 1, a perspective view illustrates an exemplary anchor 10 that can be used for securing a tissue to a bone according to the present disclosure. In various aspects, the tissue can be a soft tissue or bone. The anchor 10 can be made from various resorbable and non-resorbable bio-compatible materials including, but not limited to, polymeric materials such as polyester, polyethylene, and polypropylene, and natural materials such as cotton and silk. In various aspects, one or more components of the anchor 10 can include biological or biocompatible coatings, and also can be soaked in platelets and other biologics.

The anchor 10 can include flexible tubular members 12, 14 and a flexible suture member 16. The tubular members 12, 14 can have properties that allow the tubular members 12, 14 to change shape. For example, the tubular members 12, 14 can have properties that make them flexible, foldable, compressible, stretchable, elastic, deformable, flaccid, limp, soft, spongy or otherwise capable of changing shape. The tubular members 12, 14 can be hollow elongated structures having a sleeve or tubular configuration. In alternate constructions, the anchor 10 can include substantially solid flexible elongate members in place of the tubular members 12, 14. In various aspects, the elongate members can have a substantially flat, planar, or ribbon-like shape formed, for example, from a flat sponge-like material or a piece of woven fabric which can be pierced to allow the suture member 16 to pass through. In various other aspects, the elongate members can also have various cross-sectional shapes. For example, the shapes can be circular, polygonal, square, rectangular, etc.

The tubular member 12 can include a wall 20 defining an elongated passage 22 extending along an axis 24 between ends 26, 28. The passage 22 can have a diameter or size configured to allow the suture member 16 to pass through the tubular member 12 and to provide a locking feature through frictional and/or mechanical engagement with the suture member 16 when the suture member 16 is tensioned. The tubular member 12 can further include one or more apertures disposed between the ends 26, 28 for passing the suture member 16 through the wall 20. For example, the tubular member 12 can have six apertures 30, 32, 34, 36, 38, 40 as illustrated by the present example. The apertures 30, 32, 34, 36, 38, 40 can be spaced apart in a line as shown, and in various aspects, circumferentially spaced apart.

The tubular member 14 can include a wall 50 defining a passage 52 extending along an axis 54 between ends 56, 58. The passage 52 can have a diameter or size configured to allow the suture member 16 to pass through the tubular member 14 and to provide a locking feature through frictional and/or mechanical engagement with the suture member 16 when the suture member 16 is tensioned. The tubular member 14 can further include one or more apertures disposed between the ends 56, 58 for passing the suture member 16 through the wall 50. For example, the tubular member 14 can have four apertures 60, 62, 64, 66.

The suture member 16 can be a suture thread of a suitable length between ends 70, 72 for coupling the tubular members 12, 14 in a desired manner and for coupling the anchor 10 to the tissue by, for example, a suture stitch or other suitable coupling member.

With continued reference to FIG. 1, an exemplary method of assembling or forming the anchor 10 will now be described. The method includes coupling the tubular member 12 and the tubular member 14 using the suture member 16. The anchor 10 can be assembled or formed and the tubular members 12, 14 coupled by passing the suture member 16 through the walls 20, 50 and the passages 22, 52 in a predetermined manner. According to the present example, the suture member 16 can be passed through the walls 20, 50 to create two compression loops 74, 76 that couple the tubular members 12, 14 in a substantially parallel arrangement. The loop 74 can couple the tubular members 12, 14 near the ends 26, 56 and the loop 76 can couple the tubular members 12, 14 near the ends 28, 58.

To create the loops 74, 76, the end 70 of the suture member 16 can be passed through the aperture 30, guided through the passage 22, and passed out through the aperture 32. Next, the end 70 can be passed through the aperture 62, guided through the passage 52, and passed through the aperture 60. Next, the end 70 can be passed through the aperture 34, guided through the passage 22, and passed through the aperture 36, creating the loop 74. Next, the suture member 16 can be passed through the aperture 66, guided through the passage 52, and passed through the aperture 64. Next, the suture member 16 can be passed through the aperture 38, guided through the passage 22, and passed through the aperture 40, creating the loop 76.

Once the loops 74, 76 are created, the ends 70, 72 can be pulled to adjust a diameter or size of the loops 74, 76 and thereby bring the tubular members 12, 14 into a desired relationship in an untensioned state suitable for positioning the anchor 10 relative to the bone. In various aspects, the ends 70, 72 can be pulled such that a predetermined spacing 78 between the tubular members 12, 14 is achieved and the tubular members 12, 14 extend generally parallel to each other. In various aspects, the spacing 78 and an angle between the tubular members 12, 14 can vary so that a predetermined relationship is achieved and the anchor 10 has a desired first shape in an untensioned state when initially positioned relative to the bone. For example, the spacing 78 can be such that one or both of the tubular members 12, 14 can be deformed or folded in half without engaging each other in the untensioned state. In this way, a width of the anchor 10 in an untensioned state and a corresponding hole size can be minimized. The spacing 78 can be minimized to minimize insertion depth.

The suture member 16 can be passed through the walls 20, 50 and the passages 22, 52 in the foregoing manner to create a series of intersecting sections 80, 82, 84 and sections 86, 88 in the tubular member 12 and the tubular member 14, respectively. The intersecting sections 80, 82, 84 are sections where the suture member 16 intersects the tubular member 12, and the intersecting sections 86, 88 are sections where the suture member 16 intersects the tubular member 14. The intersecting sections 80, 82, 84, 86, 88 can be defined between the respective apertures 30, 32, 34, 36, 38, 60, 62, 64, 66. As one example, the intersecting section 80 can be defined between the aperture 30 where the suture member 16 enters the passage 22 through the wall 20 and the aperture 32 where the suture member 16 exits the passage 22 through the wall 20.

The intersecting sections 80, 82, 84, 86, 88 can be drawn towards each other and into engagement by pulling on the ends 70, 72 of the suture member 16 to create tension within the suture member 16. Tension in the suture member 16 can compress and/or deform the intersecting sections 80, 82, 84, 86, 88 individually, and together. Tension in the suture member 16 can further compress and/or deform sections of the tubular members 12, 14 extending between the intersecting sections 80, 82, 84 and sections between the intersecting sections 86, 88. In various aspects, a number and location of the intersecting sections 80, 82, 84, 86, 88 can vary and the intersecting sections 80, 82, 84, 86, 88 can have a predetermined relationship so the anchor 10 deforms between the first shape and a second shape when positioned relative to the bone and tensioned. The sections extending between the intersecting sections 80, 82, 84 and the sections extending between the intersecting sections 86, 88 can define portions of the anchoring mass that provide additional frictional and/or mechanical resistance for securing the anchor 10 relative to the bone.

In an exemplary construction, the tubular members 12, 14 can be made from a No. 5 size braided suture and the suture member 16 can be made from a No. 1 size suture. It will be appreciated that the present disclosure is not limited to such a construction, and that constructions made from other suture sizes are contemplated. The apertures 30, 32, 34, 36, 38, 40 and the apertures 60, 62, 64, 66 can be defined by voids between two or more fibers of the woven fabric of the braided suture forming the tubular members 12, 14. In this way, the apertures 30, 32, 34, 36, 38, 40, 60, 62, 64, 66 can be present without breaking the weave. When coupled by the suture member 16 in an untensioned state, the spacing 78 between the tubular members 12, 14 can be around 0.4 inches. According to the foregoing construction, the anchor 10 can provide pull out forces of between around twenty-five pounds (25 lbs) and thirty-one pounds (31 lbs) and, more particularly, around twenty-eight pounds (28 lbs). Thus, it will be appreciated that the anchor 10 according to the present disclosure can provide pull out forces that are greater than other conventional flexible anchors.

An overall length of the tubular member 12 can be around 0.74 inches. The apertures 30, 32, 34, 36, 38, 40 are disposed along the length of the tubular member 12 in a symmetrical arrangement about a line of symmetry located midway along the length located at around 0.37 inches from the ends 26, 28. Centers of the apertures 30, 32, 34 are spaced apart from the end 26 by around 0.06 inches, 0.21 inches, and 0.31 inches, respectively. Centers of the apertures 36, 38, 40 are spaced apart from the end 28 by around 0.31 inches, 0.21 inches, and 0.06 inches, respectively. According to the foregoing spacing, the intersecting sections 80, 82, 84 have lengths of around 0.15 inches, 0.12 inches, and 0.15 inches, respectively.

An overall length of the tubular member 14 can be around 1.10 inches. The apertures 60, 62, 64, 66 are disposed along the length of the tubular member 14 in a symmetrical arrangement about a line of symmetry located midway along the length located at around 0.55 inches from the ends 56, 58. Centers of the apertures 60, 62 are spaced apart from the end 56 by around 0.06 inches and 0.25 inches, respectively. Centers of the apertures 64, 66 are spaced apart from the end 58 by around 0.25 inches and 0.06 inches, respectively. Accordingly, the intersecting sections 86, 88 each have a length of around 0.19 inches. It will be appreciated that the present disclosure is not limited to the foregoing dimensions, and that other dimensional features and relationships are contemplated.

With additional reference to FIGS. 1-3, an exemplary method of securing the anchor 10 with a bone 100 according to the present disclosure will now be described. The method can include securing the anchor 10 within a region of cancellous bone tissue 102 adjacent a region of cortical bone tissue 104. The method can be used during a surgical procedure for coupling adjoining anatomy such as a soft tissue 106 to the bone 100, or other bone. For example, the method can be used during a surgical procedure for repairing a tear in the soft tissue 106 to be attached to the bone 100. More specifically, the method can be used in labral repairs, rotator cuff repairs, and anterior cruciate ligament (ACL) reconstructions.

Figures 2A, 2B:
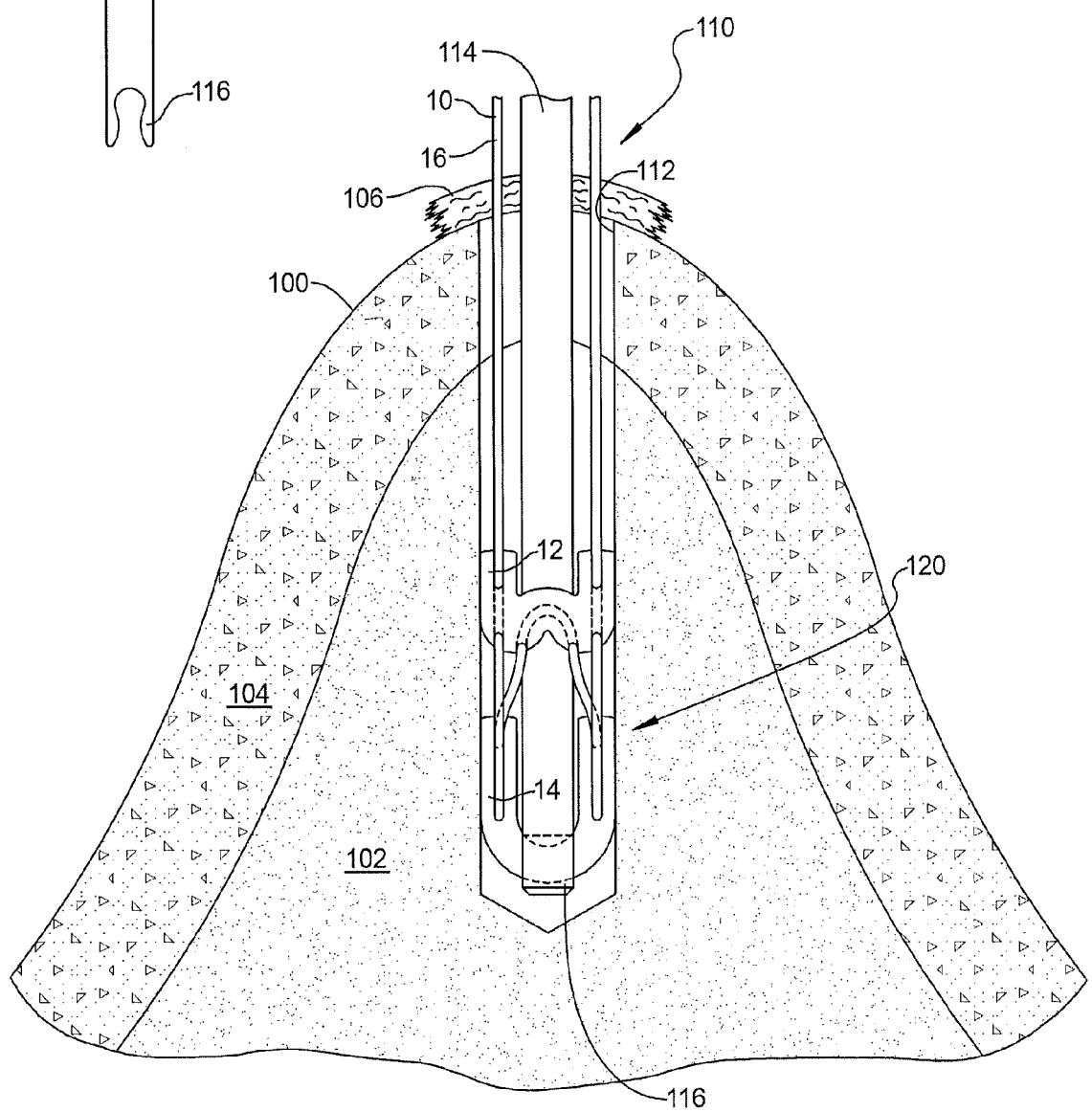
FIG. 2A is a fragmentary cross-sectional view illustrating an exemplary method of positioning an anchor within a bone according to the present disclosure.
FIG. 2B is a fragmentary side elevation view illustrating an exemplary insertion instrument according to the present disclosure.

First, an area 110 of the bone 100 for securing the anchor 10 is selected and an aperture 112 is formed in the area 110. The aperture 112 can be formed by boring into the bone 100 through the cortical bone tissue 104 into the cancellous bone tissue 102. Next, the anchor 10 can be loaded onto an insertion instrument 114 configured to insert and position the anchor 10 at a predetermined position relative to the aperture 112. As best seen in FIG. 2B, an exemplary insertion instrument 114 can include a fork 116 configured to pass between the tubular members 12, 14 and engage the tubular member 14. The anchor 10 can be loaded onto the insertion instrument 114 by coupling the tubular member 14 to the fork 116. The insertion instrument 114 can optionally include a fork 117 as shown that is configured to engage the tubular member 12 and to hold the tubular members 12, 14 in a desired relationship when positioned within the aperture 112.

With the anchor 10 loaded on to the insertion instrument 114, the loaded insertion instrument 114 can be coupled to a guide (not shown) and advanced within the aperture 112. For example, the insertion instrument 114 carrying the anchor 10 can be inserted into a cannulated guide typically used for arthroscopic surgery. The insertion instrument 114 can be advanced until the anchor 10 is positioned in a region of the cancellous bone tissue 102 a predetermined distance below the cortical bone tissue 104 as shown in FIG. 2A. With the anchor 10 thus positioned, the insertion instrument 114, and more particularly the fork 116, can be uncoupled from the anchor 10 by moving and/or withdrawing the insertion instrument 114 in an axial direction relative to the aperture 112. In an untensioned state, the anchor 10 can have a first configuration 120 or shape as shown in FIG. 2A and can frictionally and/or mechanically engage the cancellous bone tissue 102.

Figure 3:
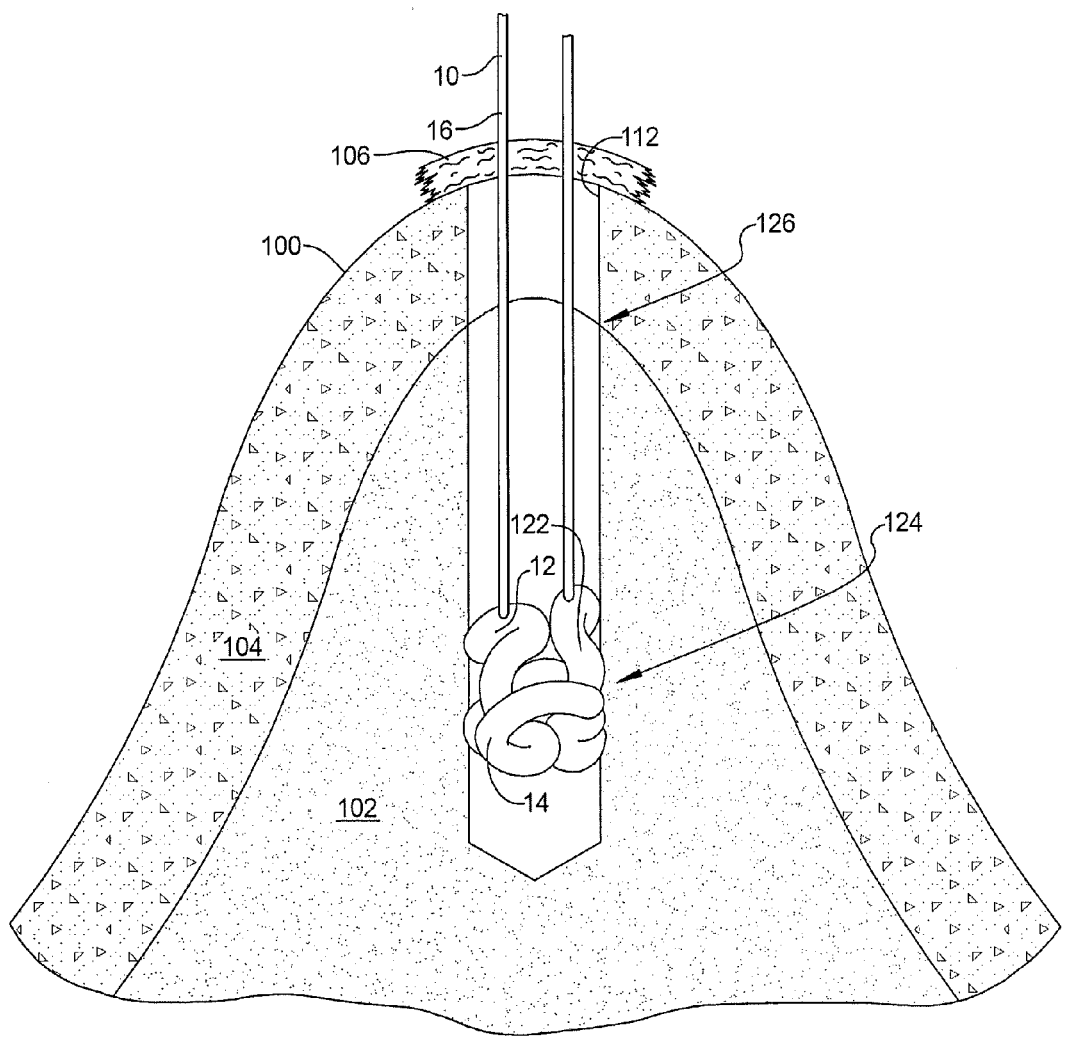
FIG. 3 is a fragmentary cross-sectional view illustrating an exemplary method of engaging an anchor with a cancellous bone tissue according to the present disclosure.

With the insertion instrument 114 uncoupled, the tubular members 12, 14 can be drawn into engagement to create an anchoring mass 122 that can secure the anchor 10 relative to the bone 100 substantially at the predetermined position as shown in FIG. 3. The anchoring mass 122 can have a second configuration 124 or shape that is different than the first configuration 120. The tubular members 12, 14 can be drawn towards each other and into engagement by pulling on the ends 70, 72 of the suture member 16 in a direction that is generally coaxial with and away from the aperture 112. In various aspects, the ends 56, 58 of the tubular member 14 can frictionally and/or mechanically engage a wall of the aperture 112. The engagement of the ends 56, 58 can retain the tubular member 14 in place relative to the aperture 112 as the tubular member 12 is drawn towards the tubular member 14 and into engagement. In this way, the tubular member 14 can retain the anchor 10 substantially at the same predetermined position as the anchor 10 is initially positioned as the suture member 16 is tensioned. In various aspects, the ends 26, 28 of the tubular member 12 do not catch on the wall of the aperture 112 as the tubular member 12 is drawn towards the tubular member 14 deeper in the aperture 112. In other aspects, as the tubular members 12, 14 are drawn into engagement with one another, the intersecting sections 80, 82, 84 of the tubular member 12 can be drawn towards and into engagement with the intersecting sections 86, 88. In still other aspects, the suture member 16 is passed through the tubular members 12, 14 so that sections of the tubular members 12, 14, including one or more of the intersecting sections 80, 82, 84, 86, 88 are forced in a direction of the wall of the aperture 112.

During the engagement, sections of the tubular members 12, 14 can compress, collapse, buckle, fold, bunch, expand, or otherwise deform to form the anchoring mass 122. In various aspects, the second configuration 124 can include an overall width that is greater than that of the first configuration 120 and a diameter or width of the aperture 112. By having a greater width, the second configuration 124 can expand into the cancellous bone tissue 102, beyond the width of the aperture 112. In this way, the second configuration 124 can provide a mechanical locking feature that secures the anchor 10 relative to the cancellous bone tissue 102. In various other aspects, the anchoring mass 122 can engage and lock against a ledge 126 defined by the cortical bone tissue.

With the anchor 10 thus set, remaining portions of the suture member 16 can be coupled to the soft tissue 106 and/or other surrounding anatomy. The suture member 16 can be coupled to the soft tissue 106 using a desired suturing technique for performing the repair. The suturing technique can include attaching the suture member 16 to another anchor and engaging the anchor with the soft tissue 106. The suturing technique can include knotting, and other suture coupling techniques. In various aspects, the suture member 16 can form various parts of a self-locking, adjustable loop construction such as those described in commonly assigned U.S. Pat. Nos. 7,658,751 and 7,601,165, the entire disclosures of which are incorporated by reference herein. For example, one or both the ends 70, 72 of the suture member 16 can form one or more loops of the construct. Alternately or additionally, one or both the ends 70, 72 can provide a tubular construct through which one or more loops of another suture pass.

Figure 4:
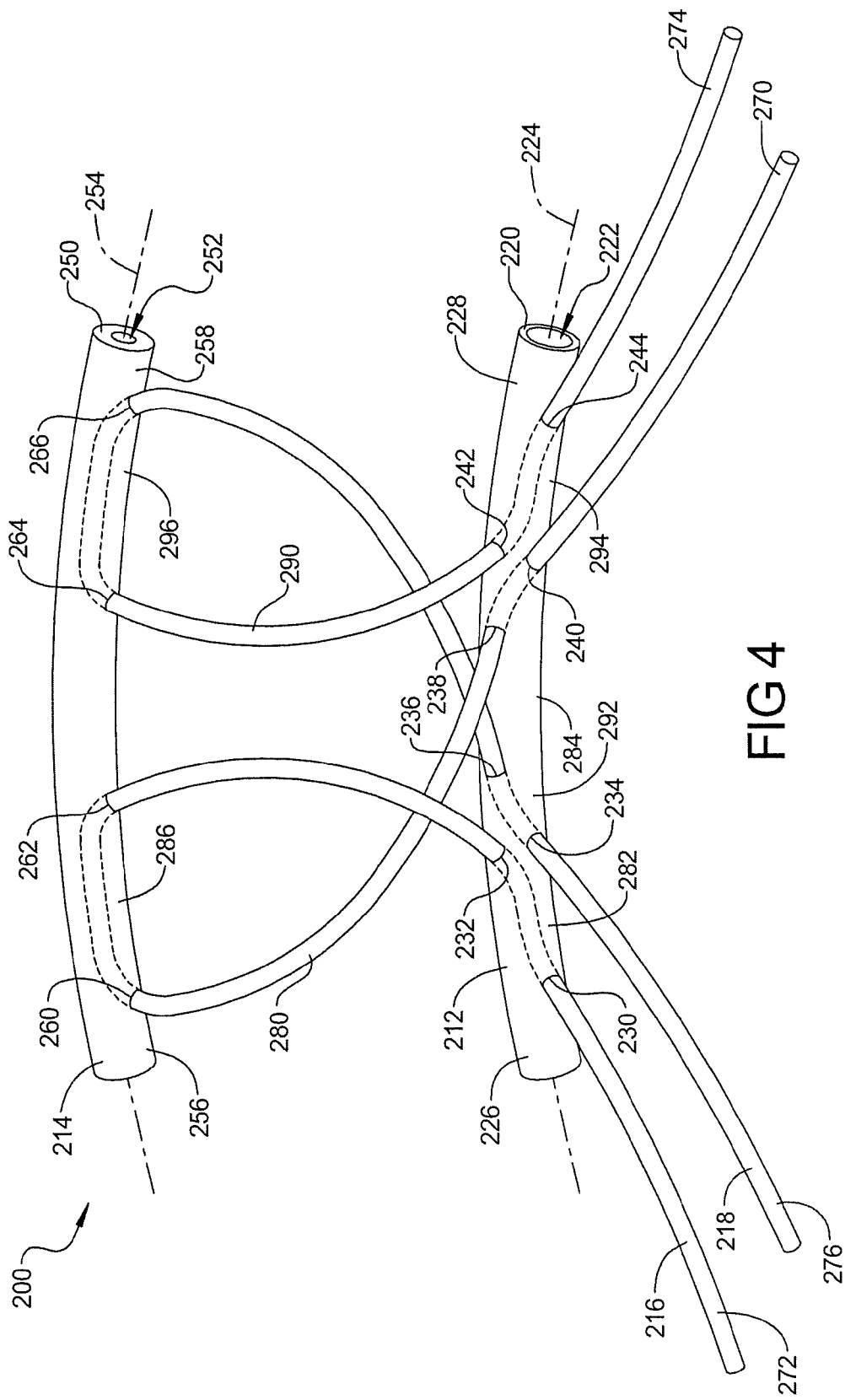
FIG. 4 is a perspective view illustrating another anchor for securing tissue to bone according to the present disclosure.

With particular reference to FIG. 4 a perspective view illustrates another anchor 200 for securing soft tissue to bone according to the present disclosure. The anchor 200 can include flexible tubular members 212, 214 and suture members 216, 218. The anchor 200 illustrates an alternate configuration according to the present disclosure. The anchor 200 is similar to the anchor 10, except that the two suture members are used to couple and deform two soft anchoring members.

The tubular member 212 can include a wall 220 defining a passage 222 extending along an axis 224 between ends 226, 228. The passage 222 can have a diameter or size configured to allow the suture members 216, 218 to pass through the tubular member 212 and to provide a locking feature through frictional and/or mechanical engagement with the suture members 216, 218 when one or both of the suture members 216, 218 are tensioned. The tubular member 212 can have eight apertures 230, 232, 234, 236, 238, 240, 242, 244. The apertures 230, 234, 240, 244 can be spaced apart along a first line as shown, and the apertures 232, 236, 238, 242 can be spaced apart along a second line circumferentially spaced apart from the first line.

The tubular member 214 can include a wall 250 defining a passage 252 extending along an axis 254 between ends 256, 258. The passage 252 can have a diameter or size configured to allow the suture members 216, 218 to pass through the tubular member 214 and to provide a locking feature through frictional and/or mechanical engagement with the suture members 216, 218 when one or both of the suture members 216, 218 are tensioned. The tubular member 214 can further include four apertures 260, 262, 264, 266.

The suture members 216, 218 can be suture threads of suitable lengths between ends 270, 272 and ends 274, 276 for coupling the tubular members 212, 214 in a desired manner and for coupling the anchor 200 to the soft tissue by, for example, a suture stitch or other suitable coupling member.

The suture member 216 can be passed through the walls 220, 250 and the passages 222, 252 to create a first loop 280 coupling the ends 226, 256 of the tubular members 212, 214, respectively. The suture member 216 can further create a series of intersecting sections 282, 284 and an intersecting section 286 in the tubular member 212 and the tubular member 214, respectively. The suture member 218 can be passed through the walls 220, 250 and the passages 222, 252 to create a second loop 290 coupling the ends 228, 258 of the tubular members 212, 214, respectively. The suture member 216 can further create a series of intersecting sections 292, 294 and an intersecting section 296 in the tubular member 212 and the tubular member 214, respectively.

Figure 5:
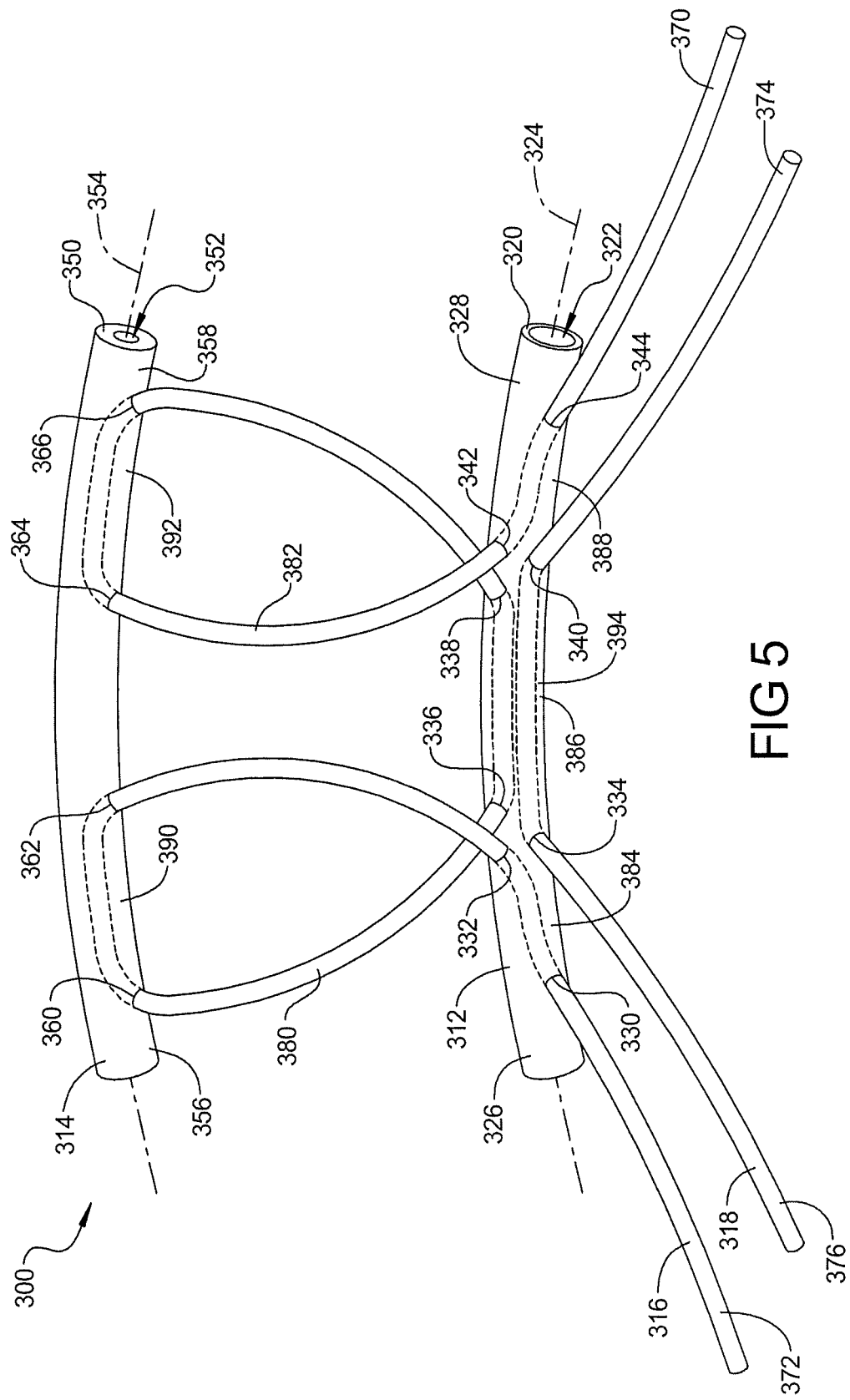
FIG. 5 is a perspective view illustrating another anchor for securing tissue to bone according to the present disclosure.

With particular reference to FIG. 5, a perspective view illustrates another anchor 300 for securing soft tissue to bone according to the present disclosure. The anchor 300 can include flexible tubular members 312, 314 and suture members 316, 318. The anchor 300 illustrates an alternate configuration according to the present disclosure. The anchor 300 is similar to the anchor 200, except that only one of the two suture members is used to couple and deform two soft anchoring members, while the second suture member is used to deform one of the two soft anchoring members. Additionally, the two suture members overlap in at least one intersecting section. The anchor 300 can provide an additional feature that multiple suture members can be separately employed to couple the two soft anchoring members and to individually deform the two soft anchoring members.

The tubular member 312 can include a wall 320 defining a passage 322 extending along an axis 324 between ends 326, 328. The passage 322 can have a diameter or size configured to allow the suture members 316, 318 to pass together through a section of the tubular member 312 and to provide a locking feature through frictional and/or mechanical engagement with the suture members 316, 318 when one or both of the suture members 316, 318 are tensioned. The tubular member 312 can have eight apertures 330, 332, 334, 336, 338, 340, 342, 344. The apertures 330, 334, 340, 344 can be spaced apart along a first line as shown, and the apertures 332, 336, 338, 342 can be spaced apart along a second line circumferentially spaced apart from the first line.

The tubular member 314 can include a wall 350 defining a passage 352 extending along an axis 354 between ends 356, 358. The passage 352 can have a diameter or size configured to allow the suture member 316 alone to pass through the tubular member 314 and to provide a locking feature through frictional and/or mechanical engagement with the suture member 316 when the suture member 316 is tensioned. The tubular member 314 can further include four apertures 360, 362, 364, 366.

The suture members 316, 318 can be suture threads of suitable lengths between ends 370, 372 and ends 374, 376 for coupling the tubular members 312, 314 in a desired manner and for coupling the anchor 300 to the soft tissue by, for example, a suture stitch or other suitable coupling member.

The suture member 316 can be passed through the walls 320, 350 and the passages 322, 352 to create two loops 380, 382 that can couple the ends 326, 356 and the ends 328, 358 of the tubular members 312, 314, respectively. The suture member 316 can be passed through the walls 320, 350 and the passages 322, 352 to create a series of intersecting sections 384, 386, 388 and sections 390, 392 in the tubular member 312 and the tubular member 314, respectively. The suture member 318 can be passed through the wall 320 and the passage 222 to create an intersecting section 394 that overlaps with the intersecting section 386. In various aspects, the suture 318 can provide a second strand of suture to secure the anchor 300 to soft tissue. The anchor 300 can be implanted or secured within a bone in a manner similar to that of the anchor 10.

Figure 6:
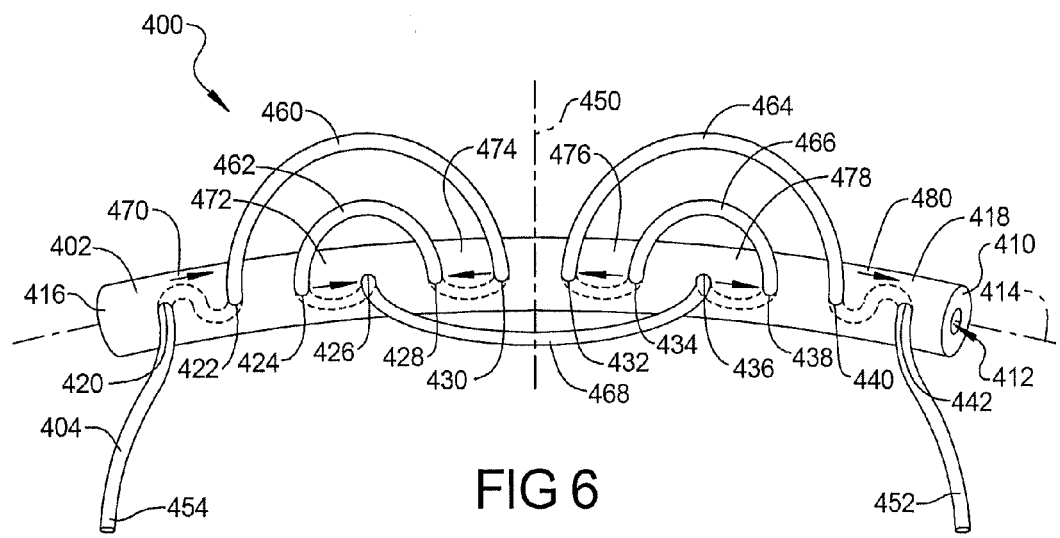
FIG. 6 is a perspective view illustrating another anchor for securing tissue to bone according to the present disclosure.

With particular reference to FIG. 6, a perspective view illustrates another anchor 400 for securing soft tissue to bone according to the present disclosure. The anchor 400 is an example of a flexible anchor configuration for creating an anchoring mass that can be constructed by coupling a single flexible tubular member and a single suture. The anchor 400 can have a configuration similar to the configuration 124 of the second anchoring mass 122 created by the anchor 10. It will be appreciated that the anchor 400 can be coupled with a second flexible tubular member incorporating features of, for example, the anchor 10, the anchor 200, and the anchor 300. The anchor 400 can include a flexible tubular member 402 and a suture member 404.

The tubular member 402 can include a wall 410 defining a passage 412 extending along an axis 414 between ends 416, 418. The passage 412 can have a diameter or size configured to allow the suture member 404 to pass through the tubular member 402 and to provide a locking feature through frictional and/or mechanical engagement with the suture member 404 when the suture member 404 is tensioned. The tubular member 402 can further include one or more apertures disposed between the ends 416, 418 for passing the suture member 404 through the wall 410. For example, the tubular member 402 can have twelve apertures 420, 422, 424, 426, 428, 430, 432, 434, 436, 438, 440, 442 as illustrated by the present example.

The apertures 420, 422, 424, 426, 428, 430, 432, 434, 436, 438, 440, 442 can be spaced apart in a line as shown, and in various aspects, circumferentially spaced apart. The apertures 420, 422, 424, 426, 428, 430, 432, 434, 436, 438, 440, 442 can have a symmetrical spacing about a line of symmetry 450, which can be located at around a midpoint between the ends 416, 418 as shown. Accordingly, the apertures 420, 422, 424, 426, 428, 430 can have a spacing relative to the line of symmetry 450 that is the same as that of the apertures 442, 440, 438, 436, 434, 432, respectively.

The suture member 404 can be a suture thread of a suitable length between ends 452, 454 for passing through the tubular member 402 in a desired manner and for coupling the anchor 400 to the soft tissue by, for example, a suture stitch or other suitable coupling member. The suture member 404 can be passed through the wall 410 and the passage 412 to create a series of nested loop sections 460, 462, nested loop sections 464, 466, a loop section 468, and intersecting sections 470, 472, 474, 476, 478, 480. For example, the end 452 of the suture member 404 can be passed through the apertures 420, 422, 430, 428, 424, 426, 436, 438, 434, 432, 440, 442 in that order. When passed in the foregoing order, the suture member 404 passes through the passage 412 between the apertures 420, 422, the apertures 424, 426, the apertures 436, 438, and the apertures 440, 442 in a first direction relative to the axis 414 indicated by arrows pointing to the right in FIG. 6. The suture member 404 passes through the passage 412 between the apertures 430, 428 and the apertures 434, 432 in a second direction relative to the axis 414 opposite the first direction indicated by the arrows pointing to the left in FIG. 6.

In an untensioned state, the anchor 400 can have a first shape as shown generally in FIG. 6. While still in the untensioned state, the anchor 400 can be deformed or folded about the line of symmetry 450 into an intermediate V-shape. The anchor 400 can be inserted within an aperture of a bone while in the intermediate V-shape. The anchor 400 can deform from the intermediate V-shape (or the first shape) to a second shape forming an anchoring mass by tensioning the suture member 404. Tension in the suture member 404 can be created by pulling on the ends 416, 418. Tension in the suture member 404 draws various intersecting sections towards each other and other intersecting sections away from each other, which deforms the tubular member 402. In various aspects, the anchoring mass can be secured within an aperture of a bone in a manner similar to that illustrated by the anchor 10 in FIG. 3, or engage a surface of a soft tissue or bone in a similar manner to that illustrated by another exemplary anchor in FIG. 9. The anchor 400 can be secured using an insertion instrument similar to the insertion instrument 114 and having a single fork (e.g., fork 116). The insertion instrument can be coupled to the anchor 400 at a location where the anchor 400 is folded.

Figure 7:
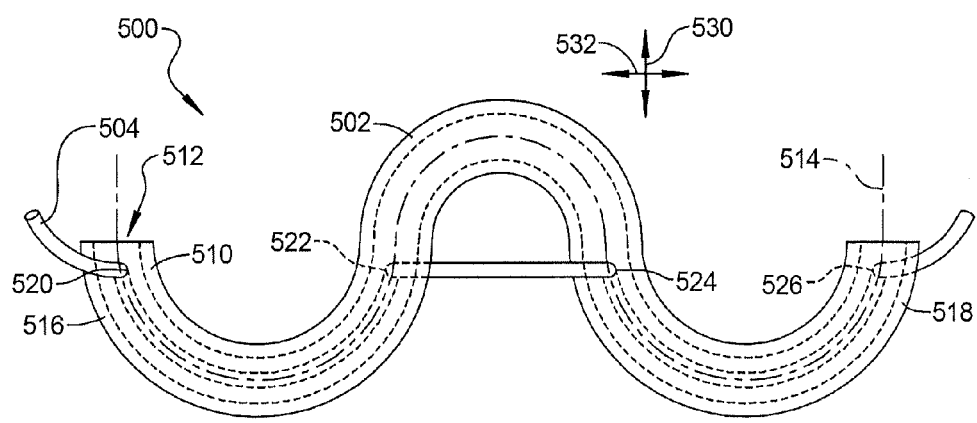
FIG. 7 is a side elevation view illustrating another anchor for securing tissue to bone according to the present disclosure.

With particular reference to FIG. 7, a side elevation view illustrates another anchor 500 for securing soft tissue to bone according to the present disclosure. The anchor 500 is another example of a flexible anchor configuration for creating an anchoring mass that can be constructed by coupling a single flexible tubular member and a single suture. The anchor 500 illustrates a feature in which the suture can deform the tubular member by twisting sections along a longitudinal axis. The anchor 500 can include a flexible tubular member 502 and a suture member 504.

The tubular member 502 can include a wall 510 defining a passage 512 extending along an axis 514 between ends 516, 518. The passage 512 can have a diameter or size configured to allow the suture member 504 to pass through the tubular member 502 and to provide a locking feature through frictional and/or mechanical engagement with the suture member 504 when the suture member 504 is tensioned. The tubular member 502 can further include two or more apertures disposed on opposite sides between the ends 516, 518 for passing the suture member 504 through the wall 510. For example, the tubular member 502 can have four apertures 520, 522, 524, 526 as illustrated by the present example.

The apertures 520, 524 can be disposed on a first side of the tubular member 502, for example, a near side in FIG. 7. The apertures 522, 526 can be disposed on a second side of the tubular member 502 opposite the first side, for example, a far side in FIG. 7. In various aspects, the apertures 520, 524 and the apertures 522, 526 can be diametrically opposed (i.e., disposed at 180 degrees relative to each other) when viewed along the axis 514.

In an untensioned state, the anchor 500 can have an accordion first shape as shown generally in FIG. 7. While still in the untensioned state, the anchor 500 can be deformed or folded into an intermediate V-shape. The intermediate V-shape can have a height in a first direction indicated by arrow 530 that is proportional to the length of the tubular member 502. The intermediate V-shape can have a width in a second direction transverse to the first direction indicated by arrow 532 that is proportional to the diameter of the diameter of the tubular member 502. The anchor 500 can be inserted within an aperture of a bone while in the intermediate V-shape. The anchor 500 can deform from the intermediate V-shape (or the first shape) to an accordion second shape forming an anchoring mass by tensioning the suture member 504. The second shape can be wider than the intermediate V-shape in the first direction indicated by arrow 532, and can be narrower than the intermediate V-shape in the second direction indicated by arrow 530. Tension in the suture member 504 can be created by pulling on the ends 516, 518. Tension in the suture member 504 can draw the aperture 522 towards the aperture 524 and twist and ball up a section of the tubular member 502 between them.

In various aspects, the anchoring mass can be secured within an aperture of a bone in a manner similar to that illustrated by the anchor 10 in FIG. 3. For example, the anchor 500 can be positioned within a preformed bore so that the suture member 504 extends generally parallel to an axis of the bore and the tubular member 502 expands in a direction transverse to the axis when the suture member 504 is tensioned. Alternately, the anchoring mass can engage a surface of a soft tissue or a bone in a similar manner to that illustrated by the exemplary anchor shown in FIG. 9.

Figure 8:
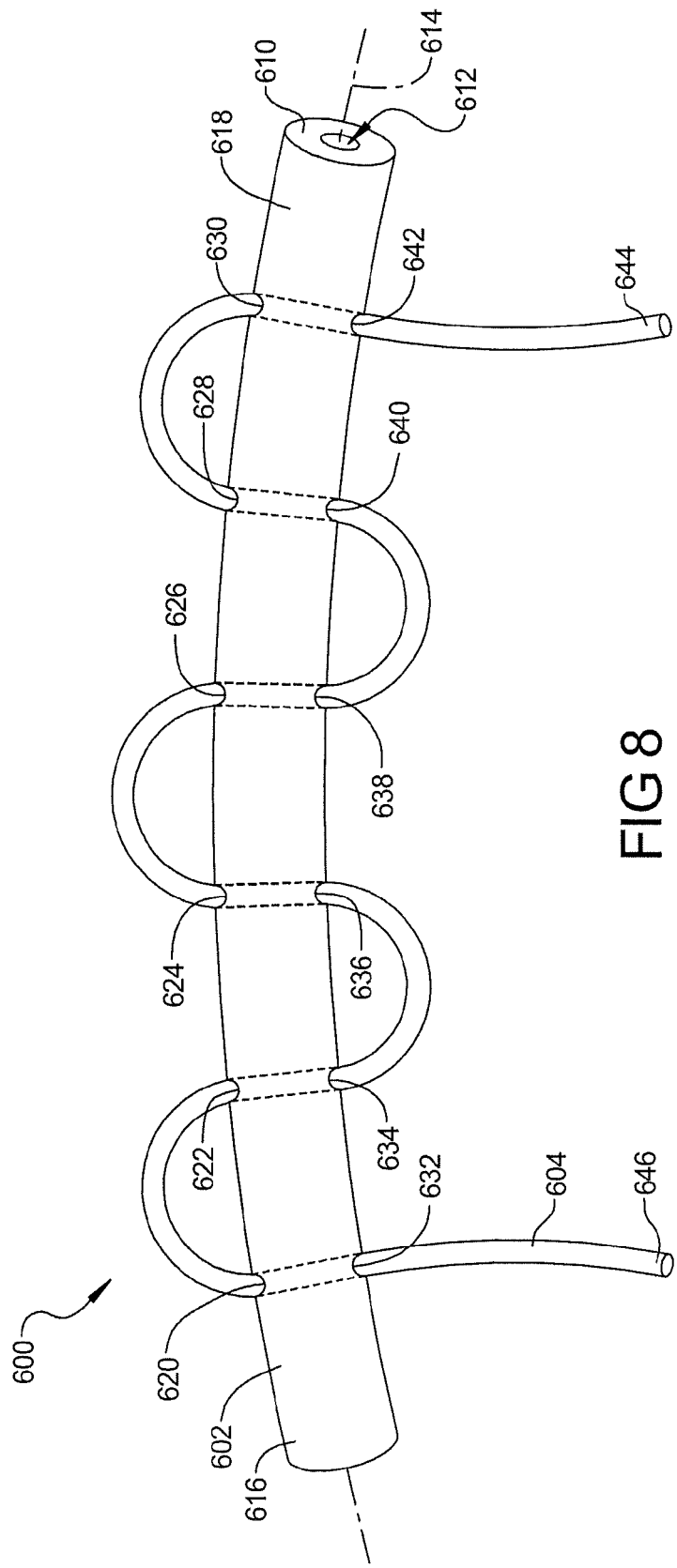
FIG. 8 is a perspective view illustrating another anchor for securing tissue to bone according to the present disclosure.

With particular reference to FIG. 8, a perspective view illustrates another anchor 600 for securing soft tissue to bone according to the present disclosure. The anchor 600 is another example of a flexible anchor configuration for creating an anchoring mass that can be constructed by coupling a single flexible tubular member and a single suture. The anchor 600 illustrates a feature in which the suture can deform the tubular member by bending or folding sections in an alternate manner.

The anchor 600 can include a flexible tubular member 602 and a suture member 604. The tubular member 602 can include a wall 610 defining a passage 612 extending along an axis 614 between ends 616, 618. The passage 612 can have a diameter or size configured to allow the suture member 604 to pass through the tubular member 602 and to provide a locking feature through frictional and/or mechanical engagement with the suture member 604 when the suture member 604 is tensioned. The tubular member 602 can further include, for example, six or more apertures disposed on opposite sides between the ends 616, 618 for passing the suture member 604 through the wall 610. For example, the tubular member 602 can have twelve apertures 620, 622, 624, 626, 628, 630, 632, 634, 636, 638, 640, 642 as illustrated by the present example.

The apertures 620, 622, 624, 626, 628, 630 can be disposed in a first line on a first side of the tubular member 602, for example, a top side in FIG. 8. The apertures 632, 634, 636, 638, 640, 642 can be disposed in a second line on a second side of the tubular member 602 opposite the first side, for example, a bottom side in FIG. 8. In various aspects, the apertures 620, 622, 624, 626, 628, 630 and the apertures 632, 634, 636, 638, 640, 642 can be diametrically opposed. A longitudinal spacing of the apertures 620, 622, 624, 626, 628, 630 can be equal to that of the apertures 632, 634, 636, 638, 640, 642. As one example, the aperture 620 and the aperture 632 can be equally spaced from the first end 616 as shown.

Figure 9:
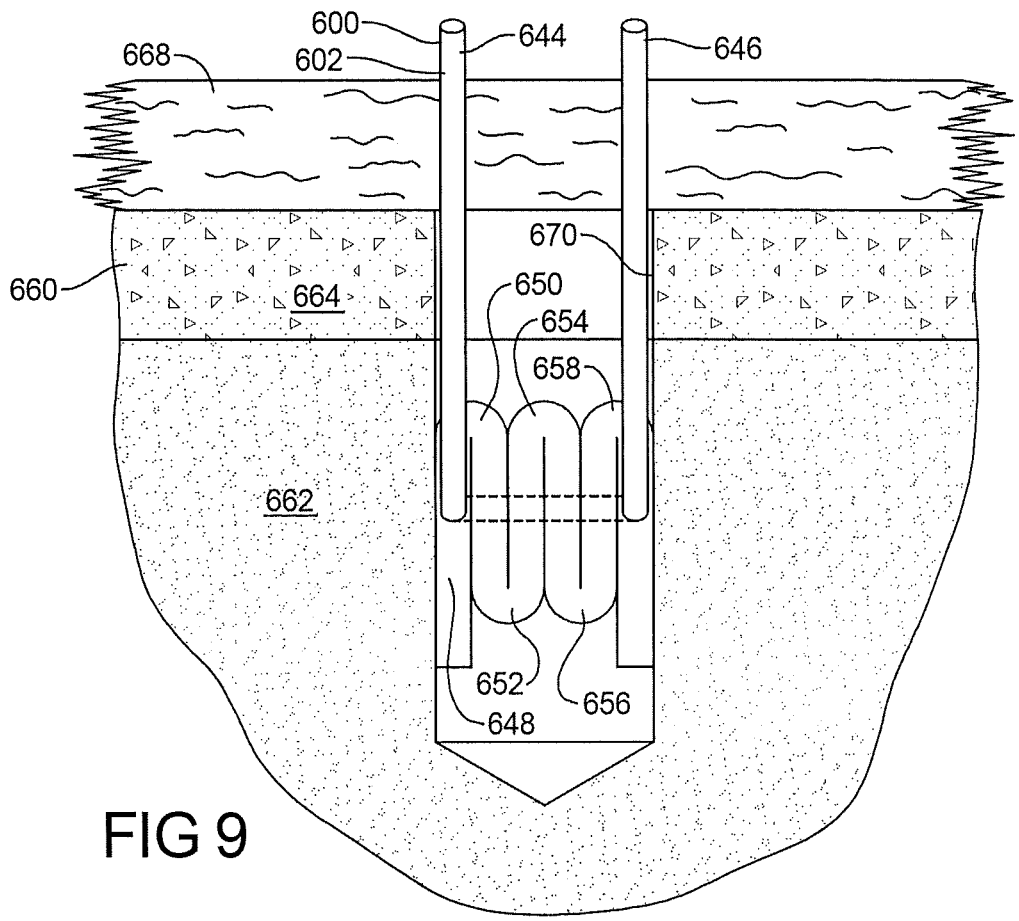
FIG. 9 is a fragmentary cross-sectional view illustrating an exemplary method of engaging the anchor shown in FIG. 8 with a tissue according to the present disclosure.
Figure 10:
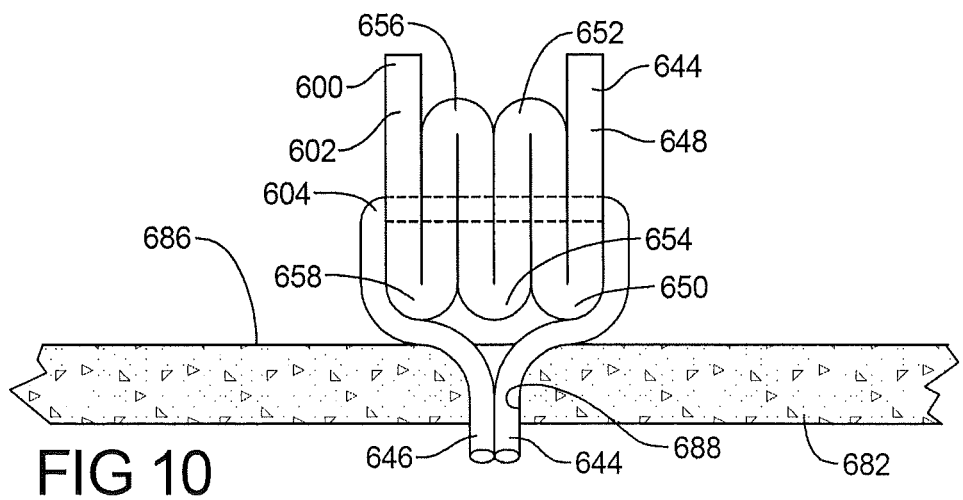
FIG. 10 is a fragmentary cross-sectional view illustrating an exemplary method of engaging the anchor shown in FIG. 8 with a cortical bone tissue according to the present disclosure.

The suture member 604 can be a suture thread of a suitable length between ends 644, 646 for passing through the tubular member 602 in a desired manner and for coupling the anchor 600 to the soft tissue by, for example, a suture stitch or other suitable coupling member. In an untensioned state, the anchor 600 can have a first shape as shown generally in FIG. 8. The anchor 600 can deform from the first shape to an accordion second shape as shown in FIGS. 9-10 forming an anchoring mass 648 by tensioning the suture member 604. Tension in the suture member 604 can be created by pulling on the ends 644, 646. Tension in the suture member 604 can draw the apertures 620, 622, the apertures 634, 636, the apertures 624, 626, 638, 640, and the apertures 628, 630 towards each other in an alternating fashion and create a series of folded sections 650, 652, 654, 656, 658 as shown in FIGS. 9-10.

With additional reference to FIGS. 8-9, an exemplary method of securing the anchor 600 with a bone 660 according to the present disclosure will now be described. The method can include securing the anchor 600 within a region of cancellous bone tissue 662 adjacent a region of cortical bone tissue 664. The method can be used during a surgical procedure for coupling adjoining anatomy such as a soft tissue 668 to the bone 660.

The method can include positioning the anchor 600 in a bore 670 prepared in a selected area of the bone 660 and tensioning the suture member 602 to set the anchoring mass 648 within the cancellous bone tissue 662 as shown in FIG. 9. With the anchoring mass 648 set, the ends 644, 646 can be passed through the soft tissue 668 and can be coupled to the soft tissue 668 by, for example, a suturing technique. When coupled, tension in the suture member 602 can compress the soft tissue 668 against the bone 660.

With additional reference to FIGS. 8 and 10, an exemplary method of engaging the anchor 600 with a bone 682 will now be described. It will be appreciated that the following method is not limited to the anchor 600, and can be used with other anchors according to the present disclosure. Generally, the method includes coupling the anchor 600 with a bone engaging surface 686. The method can include tensioning the suture member 602 to create the anchoring mass 648 and passing the ends 644, 646 through an aperture 688 formed in the bone 682 and coupling the ends 644, 646 to an anchor (not shown) positioned within the aperture 688. When coupled, tension in the suture member 602 can compress the anchor 600 against the bone engaging surface 686 of the bone 682. The anchoring mass 648 resists pull through. The foregoing method of coupling the anchor 600 to the bone 682 can be used, for example, during an ACL reconstruction surgery.

Figure 11:
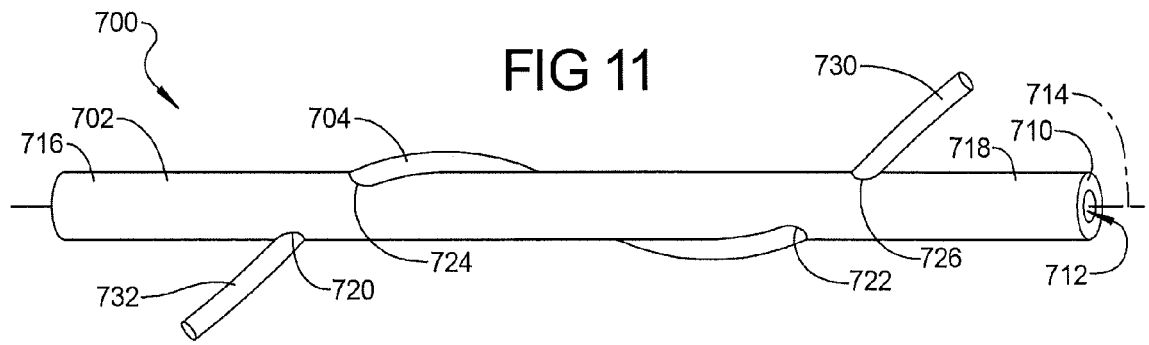
FIG. 11 is a side elevation view illustrating another anchor for securing tissue to bone according to the present disclosure.

With particular reference to FIG. 11, a side elevation view illustrates another anchor 700 for securing soft tissue to bone according to the present disclosure. The anchor 700 is another example of a flexible anchor configuration for creating an anchoring mass that can be constructed by coupling a single flexible tubular member and a single suture member. The anchor 700 illustrates a feature in which the suture member can be wrapped around the flexible tubular member and can deform the tubular member by twisting sections of the tubular member about its longitudinal axis.

The anchor 700 can include a flexible tubular member 702 and a suture member 704. The tubular member 702 can include a wall 710 defining a passage 712 extending along an axis 714 between ends 716, 718. The passage 712 can have a diameter or size configured to allow the suture member 704 to pass through the tubular member 702 and to provide a locking feature through frictional and/or mechanical engagement with the suture member 704 when the suture member 704 is tensioned. The tubular member 702 can further include, for example, two or more apertures disposed on opposite sides between the ends 716, 718 for passing the suture member 704 through the wall 710. For example, the tubular member 702 can have four apertures 720, 722, 724, 726 as illustrated by the present example.

The apertures 720, 722 can be disposed in a first line on a first side of the tubular member 702, for example, a bottom side in FIG. 11. The apertures 724, 726 can be disposed in a second line on a second side of the tubular member 702 opposite the first side, for example, a top side in FIG. 11. In various aspects, the apertures 720, 722 and the apertures 724, 726 can be diametrically opposed when viewed along the axis 714. A longitudinal spacing of the apertures 720, 722 can be different than that of the apertures 724, 726. As one example, the apertures 724, 726 can be spaced further from the first end 716 than the apertures 720, 722, respectively, as shown.

The suture member 704 can be a suture thread of a suitable length between ends 730, 732 for passing through the tubular member 702 in a desired manner and for coupling the anchor 700 to the soft tissue. The anchor 700 can be assembled or formed by passing the suture member 704 through the wall 710 and the passage 712 in the following manner. The end 730 can be passed in the first side through the aperture 720, guided through the passage 712, and out the second side through the aperture 724. Next, the end 730 can be wrapped around the circumference of the tubular member 702 to the first side. The end 730 can then be passed in the first side again through the aperture 722, guided through the passage 712, and out the second side again through the aperture 726.

In an untensioned state, the anchor 700 can have a first shape as shown generally in FIG. 11. The anchor 700 can deform from the first shape to second shape forming an anchoring mass by tensioning the suture member 704. Tension in the suture member 704 can be created by pulling on the ends 730, 732. Tension in the suture member 704 can draw the aperture 722 towards the aperture 724 and twist a section of the tubular member 702 between them.

Figure 12:
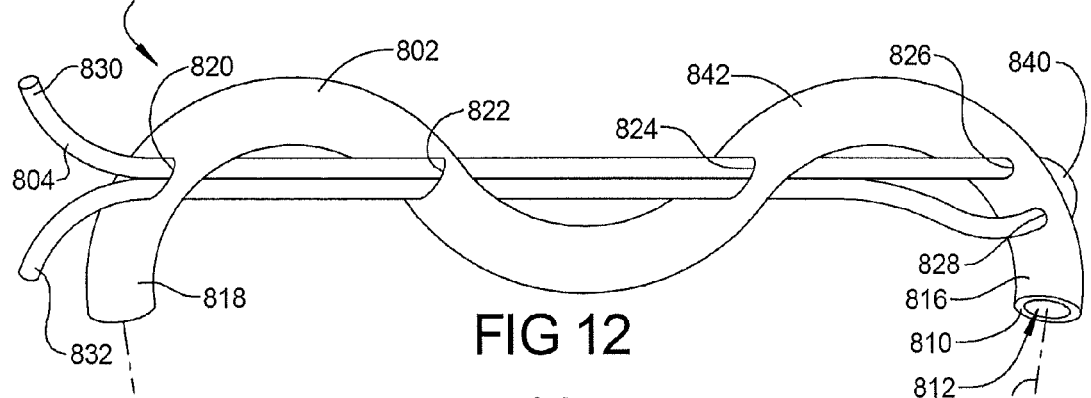
FIG. 12 is a perspective view illustrating another anchor for securing tissue to bone according to the present disclosure.

With particular reference to FIG. 12, a perspective view illustrates another anchor 800 for securing soft tissue to bone according to the present disclosure. The anchor 800 can include a flexible tubular member 802 and a suture member 804. The tubular member 802 can include a wall 810 defining a passage 812 extending along an axis 814 between ends 816, 818. The passage 812 can have a diameter or size configured to allow the suture member 804 to pass through the tubular member 802 when doubled up and to provide a locking feature through frictional and/or mechanical engagement with the suture member 804 when the suture member 804 is tensioned. The tubular member 802 can further include three or more apertures disposed between the ends 816, 818 for passing the suture member 804 through the wall 810. For example, the tubular member 802 can have five apertures 820, 822, 824, 826, 828 as illustrated by the present example.

The apertures 820, 822, 824, 826, 828 can extend transverse to the axis 814 through the wall 810 from a first side, for example, a side facing to the left in FIG. 12, through to a second side opposite the first side, for example, a side facing to the right in FIG. 12. The apertures 820, 822, 824 have a size configured to allow the suture member 804 to pass through the wall 810 when doubled up as shown. The apertures 826, 828 can be smaller than the apertures 820, 822, 824 and can have a size configured to allow the suture member 804 to pass through the wall 810.

The suture member 804 can be a suture thread of a suitable length between ends 830, 832 for passing through the tubular member 802 in a desired manner and for coupling the anchor 800 to the soft tissue by, for example, a suture stitch or other suitable coupling member.

The anchor 800 can be assembled or formed by passing the suture member 804 through the wall 810 and the passage 812 in the following manner. The ends 830, 832 can be individually passed in the second side through the apertures 826, 828, respectively, guided through the passage 812, and passed out the first side through the apertures 826, 828, respectively. Passing the ends 830, 832 in the foregoing manner can create a loop section 840 that can engage an outer surface 842 of the wall 810. In various aspects, the loop section 840 can provide a stop that fixes a section of the tubular member 802 at the end 816 relative to the loop section 840. Next, the ends 830, 832 can be passed together in the second side through aperture 824, guided through the passage 812, and passed out the first side together through the aperture 824. The ends 830, 832 can be passed together through the apertures 822, and 820, in that order, in a similar manner as just described relative to the aperture 824.

Figure 13:
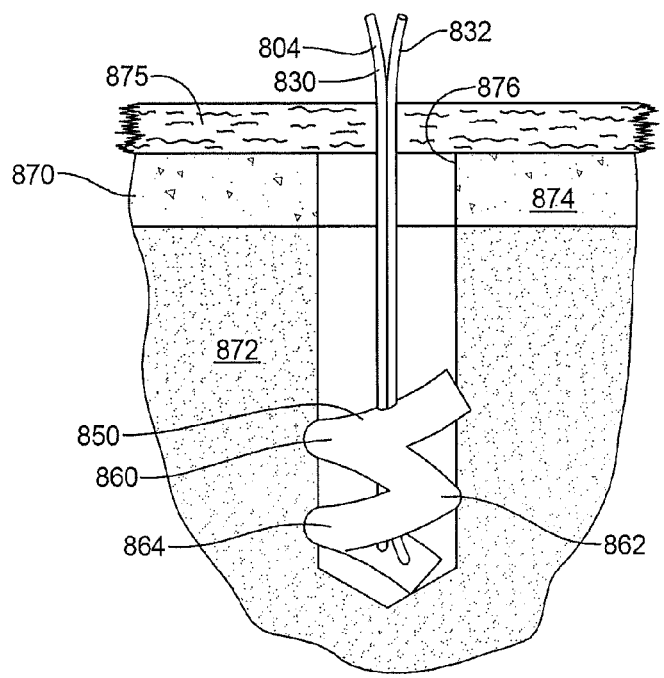
FIG. 13 is a fragmentary side elevation view illustrating an exemplary method of engaging the anchor of FIG. 12 with a cancellous bone tissue according to the present disclosure.

In an untensioned state, the anchor 800 can have an accordion first shape as shown generally in FIG. 12. The anchor 800 can deform from the first shape to an accordion second shape as shown in FIG. 13 forming an anchoring mass 850 by tensioning the suture member 804. Tension in the suture member 804 can be created by pulling on the ends 830, 832. Tension in the suture member 804 can draw the apertures 820, 822, 824 towards the apertures 826, 828, and can compress the tubular member 802 to create a series of folded sections 860, 862, 864 as shown in FIG. 13.

With additional reference to FIG. 13, an exemplary method of securing the anchor 800 with a bone 870 according to the present disclosure will now be described. The method can include securing the anchor 800 within a region of cancellous bone tissue 872 adjacent a region of cortical bone tissue 874. The method can be used during a surgical procedure for coupling adjoining anatomy such as a soft tissue 875 to the bone 870.

The method can include positioning the anchor 800 in a bore 876 prepared in a selected area of the bone 870 and tensioning the suture member 802 to set the anchoring mass 850 within the cancellous bone tissue 872 as shown in FIG. 13. During setting, the folded sections 860, 862, 864 and sections at the ends 816, 818 can frictionally engage and/or expand beyond the bore 876 and can become embedded in the cancellous bone tissue 872. With the anchoring mass 850 set, the ends 830, 832 can be passed through the soft tissue 875 and can be coupled to the soft tissue 875 by, for example, a suturing technique. When coupled, tension in the suture member 802 can compress the soft tissue 875 against the bone 870.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. An anchor for securing tissue to bone, comprising:
   a flexible first tubular member including a first wall defining a first passage between first and second ends;
   a flexible second tubular member including a second wall defining a second passage between first and second ends, the flexible second tubular member extends in a plane laterally spaced apart from the flexible first tubular member; and
   a first suture member coupling the first tubular member and the second tubular member together, the first suture member passing through the first wall and the first passage and the second wall and the second passage, the first suture member extends from the flexible first tubular member to the flexible second tubular member and back to the flexible first tubular member, and then back to the flexible second tubular member;
   wherein the first tubular member and the second tubular member engage each other and deform to form an anchoring mass upon tensioning the first suture member.

2. The anchor according to claim 1, wherein:
   the first suture member passes through the first wall and first passage and the second wall and the second passage a plurality of times to form a first loop and a second loop, the first loop couples the first end of the first tubular member and the first end of the second tubular member, and the second loop couples the second end of the first tubular member and the second end of the second tubular member.

3. The anchor according to claim 1, wherein the first tubular member and the second tubular member have a braided construction.

4. The anchor according to claim 1, wherein the anchoring mass has a locking configuration.

5. The anchor according to claim 1, wherein the first tubular member and the second tubular member each deform from a first shape to a second shape upon tensioning the first suture member and directly engaging the first tubular member to the second tubular member.

6. The anchor according to claim 1, wherein:
   the first suture member intersects first sections of the first tubular member and second sections of the second tubular member, and
   the first sections engage the second sections upon tensioning the first suture member.

7. The anchor according to claim 1, wherein the first tubular member extends substantially parallel to the second tubular member.

8. The anchor according to claim 1, wherein the first suture member forms a loop extending between the flexible first tubular member and the flexible second tubular member.

9. An anchor for securing tissue to bone, comprising:
   a flexible first tubular member including a wall defining a passage extending along a longitudinal axis between first and second ends; and
   a first suture member passing through the wall and the passage a plurality of times to create a plurality of intersecting sections and at least one loop section coupling the plurality of intersecting sections;
   wherein each of the intersecting sections extends along at least a portion of the longitudinal axis of the flexible first tubular member between a first aperture in the wall through which the first suture member enters the passage and a second aperture in the wall through which the first suture member exits the passage, and wherein at least two of the plurality of intersecting sections move towards each other and deform a section extending between them upon tensioning the first suture member;
   wherein the first suture member forms a loop extending between the first tubular member and a second tubular member spaced apart therefrom to couple the flexible first tubular member and the flexible second tubular member together, the first suture member extending from the first tubular member to the second tubular member and back to the first tubular member, and then back to the second tubular member.

10. The anchor according to claim 9, wherein:
    the first suture member passes through the wall a plurality of times to create a first pair of nested loop sections, a second pair of nested loop sections disposed adjacent the first pair of nested loop sections, and a third loop section coupling the first pair of nested loop sections and the second pair of nested loop sections, and
    the first pair of nested loop sections, the second pair of nested loop sections, and the third loop section move the at least two of the intersecting sections towards each other.

11. The anchor according to claim 9, wherein the first suture member passes through the wall between a first side and a second side a plurality of times.

12. The anchor according to claim 9, wherein the loop is a compression loop.

13. An anchor for securing tissue to bone, comprising:
    a flexible first elongate member having a first end and a second end, a first longitudinal axis extending along a length of the flexible first elongate member between the first and the second ends thereof;

a flexible second elongate member having a first end and a second end, a second longitudinal axis extending along a length of the flexible second elongate member between the first and the second ends thereof; and a suture member coupling the first elongate member and the second elongate member, the suture member extending from the first elongate member to the second elongate member, back to the first elongate member, and then back to the second elongate member, the suture member passing through both the first elongate member and the second elongate member a plurality of times, such that the flexible first elongate member and the flexible second elongate member are spaced apart and extend generally parallel to one another relative to their respective lengths such that the first longitudinal axis extends generally parallel to the second longitudinal axis;

wherein the first elongate member and the second elongate member engage each other and deform to form an anchoring mass upon tensioning the suture member.

14. The anchor according to claim 13, wherein:

at least one of the first elongate member and the second elongate member includes a tubular construction having a wall defining a passage between the first and second ends, and the suture member passes through the wall at a plurality of different locations and extends through a length of the passage.

15. The anchor according to claim 13, wherein at least one of the first elongate member and the second elongate member has a braided construction.

16. The anchor according to claim 13, wherein at least one of the first elongate member and the second elongate member has a substantially solid construction.

17. The anchor according to claim 13, wherein:

the suture member passes through the first elongate member and the second elongate member to form a first loop and a second loop, the first loop couples the first end of the first elongate member and the first end of the second elongate member, and the second loop couples the second end of the first elongate member and the second end of the second elongate member.

18. The anchor according to claim 13, wherein the first elongate member extends substantially parallel to the second elongate member.

19. An anchor for securing tissue to bone, comprising:

a first flexible tubular member having a first wall defining a first passage extending between first and second ends of the first flexible tubular member along a first axis, the first axis extending between the first and the second ends along a length of the first flexible tubular member;

a second flexible tubular member having a second wall defining a second passage extending between first and second ends of the second flexible tubular member along a second axis, the second axis extending between the first and the second ends along a length of the second flexible tubular member, the second flexible tubular member is separate from the first flexible tubular member, the first and the second flexible tubular members configured to be arranged such that the first axis and the second axis extend generally parallel to one another; and a suture member coupling the first tubular member and the second tubular member together, the suture member passing through the first wall and the first passage and the second wall and the second passage a plurality of times to form a first adjustable loop and a second adjustable loop, the suture member extending along at least a portion of the length of the first flexible tubular member along the first axis, the suture also extending along at least a portion of the length of the flexible second tubular member along the second axis, the suture member extending from the first flexible tubular member to the second flexible tubular member and back to the first flexible tubular member, and then back to the second flexible tubular member.

20. The anchor according to claim 19, wherein the first loop couples the first end of the first tubular member and the first end of the second tubular member and the second loop couples the second end of the first tubular member and the second end of the second tubular member.

21. The anchor according to claim 19, wherein the first flexible tubular member and the second flexible tubular member are configured to directly engage each other and deform to form an anchoring mass upon tensioning the suture member.

22. The anchor according to claim 19, wherein the first flexible tubular member extends substantially parallel to the second flexible tubular member in an untensioned state.

23. The anchor according to claim 19, wherein the first flexible tubular member and the second flexible tubular member are each formed of a braided suture construct.

24. The anchor according to claim 19, wherein the suture member passes through a first aperture in the first wall of the first flexible tubular member along a first portion of the first passage and exits out a second aperture in the first wall of the first flexible tubular member, passes through a first aperture in the second wall of the second flexible tubular member, extends along a first portion of the second passage, and exits out a second aperture in the second wall of the second flexible tubular member, and enters a third aperture in the first wall of the first flexible tubular member to form the first loop.

25. The anchor according to claim 24, wherein the suture member passes through a second portion of the first passage and exits out a fourth aperture in the first wall of the first flexible tubular member, passes through a third aperture in the second wall of the second flexible tubular member, passes along a second portion of the second passage, and exits out a fourth aperture in the second wall of the second flexible tubular member, passes through a fifth aperture in the first wall of the first flexible tubular member, and extends along a third portion of the first passage, and exits out a sixth aperture through the first wall of the first flexible tubular member to form the second loop.

26. The anchor according to claim 19, wherein the suture member passes through the first and second flexible tubular members a plurality of times to form a plurality of intersecting sections in the first flexible tubular member and the second flexible tubular member that are configured to be drawn toward each other upon pulling on ends of the suture member.

27. The anchor according to claim 26, wherein the first flexible tubular member includes three intersecting sections and the second flexible tubular member includes two intersecting sections formed by the first and second loops.

* * * * *